US006153194A

United States Patent [19]
Skare et al.

[11] Patent Number: 6,153,194
[45] Date of Patent: Nov. 28, 2000

[54] *BORRELIA BURGDORFERI* OUTER MEMBRANE PROTEINS

[75] Inventors: Jonathan T. Skare, College Station, Tex.; Ellen S. Shang, Calabasas, Calif.; Cheryl I. Champion, Los Angeles, Calif.; David R. Blanco, Calabassas, Calif.; James N. Miller, Northridge, Calif.; Michael A. Lovett, Los Angeles, Calif.; Tajib A. Mirzabekov, Newton, Mass.; Bruce L. Kagan, Pacific Palisades, Calif.; Paul Tempst, New York, N.Y.; Denise M. Foley, Orange, Calif.

[73] Assignee: The Regents of the University of California, Oakland, Calif.

[21] Appl. No.: 09/183,217

[22] Filed: Oct. 29, 1998

Related U.S. Application Data

[63] Continuation of application No. 08/787,367, Jan. 21, 1997, abandoned
[60] Provisional application No. 60/010,321, Jan. 22, 1996.
[51] Int. Cl.$^7$ .......................... A61K 39/00; A61K 39/02; G01N 33/554; C07K 1/00
[52] U.S. Cl. .................................. 424/184.1; 424/234.1; 435/7.32; 530/350
[58] Field of Search ............................ 424/184.1, 234.1; 530/350; 435/7.32

[56] References Cited

U.S. PATENT DOCUMENTS 5,470,712  11/1995  Simpson et al. .................... 435/7.32

OTHER PUBLICATIONS

Skare et al. Abstract of the 96th General Meeting of the American Society for Microbiology, May 19–23, 1996. p. 248.

Skare et al. Journal of Clinical Investigation 96:2380–2392, 1995.

Skare et al. Journal of Bacteriology 178(16):4909–4918, 1996.

Norris et al. Injection and Immunity 60(11):4662–4672, 1992.

*Primary Examiner*—James C. Housel
*Assistant Examiner*—V. Ryan
*Attorney, Agent, or Firm*—Fulbright & Jaworski L.L.P.

[57] ABSTRACT

The present invention presents three *B. burgdorferi* membrane proteins: Oms28, Oms45, and Oms66, each of about 28, 45, and 66 kDa respectively; and with average single channel conductances of about 0.6, 0.22, and 9.7 nS, respectively. Also disclosed are the methods for purifying these proteins from *B. burgdorferi*, methods for producing antibodies to these proteins, and the resulting antibodies. These proteins and their immunogenic fragments, and antibodies capable of binding to them are useful for inducing an immune response to pathogenic *B. burgdorferi* as well as providing a diagnostic target for Lyme disease. Further disclosed are the nucleotide and amino acid sequences, the cloning of the genes encoding the proteins and their recombinant proteins, and methods for obtaining the foregoing. Other *B. burgdorferi* outer membrane spanning proteins (Oms) obtainable by the isolation and purification methods of the present invention.

5 Claims, 24 Drawing Sheets

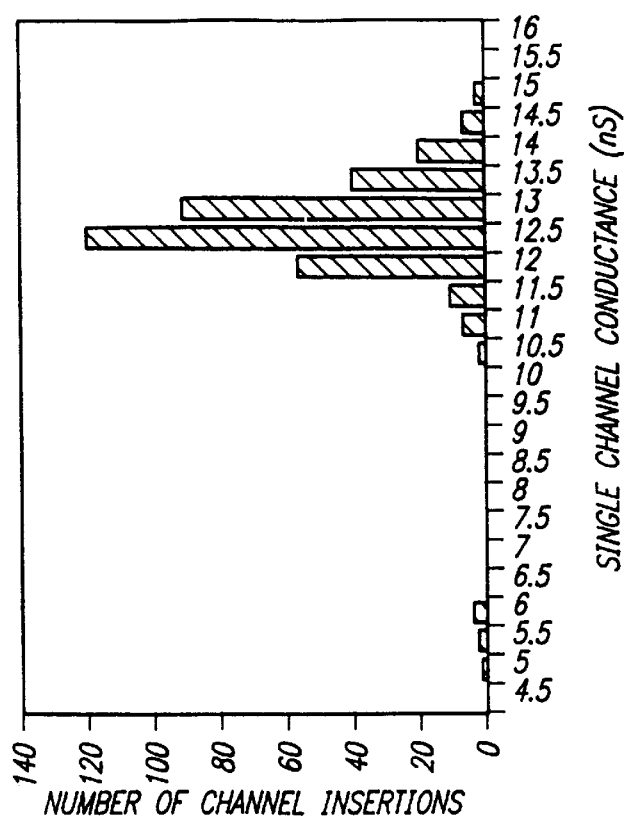
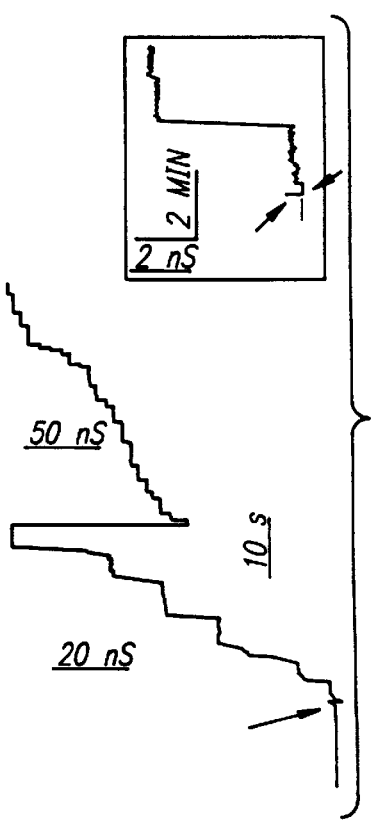
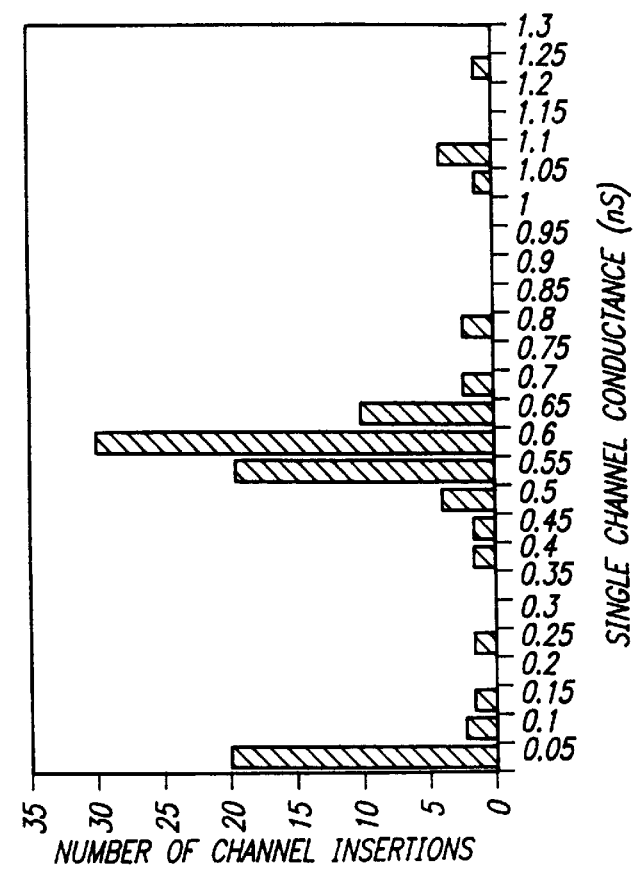
FIG. 7A
FIG. 7B
FIG. 7C

FIG. 10-1

```
                                                    TTTAAATTAAAAA
      -100
      AAGTTAAATTATTAATTAATTTTTATTAAATATGTATTGGTTCTAATTTA
      -50    (-10)                  (-35)
      GTTATGTTTAAAATAATAAAAATAAATGTTTAAATAAGGAGAATTAACA
       1                                          RBS           60
      ATG ACT AAA ATA TTT AGT AAT TTA ATA ATT AAT GGA TTA TTG TTT GGA TTT GTA AGT TTA
       M   T   K   I   F   S   N   L   I   I   N   G   L   L   F   G   F   V   S   L
       61                                                                          120
      AAT GTG TTT GCA GAT TCT AAC AAT GCA AAT ATT CTC AAG CCT CAA TCC AAT GTT TTA GAA
       N   V   F   A   D   S   N   N   A   N   I   L   K   P   Q   S   N   V   L   E
      121                                                                          180
      CAC TCA GAT CAA CAA AAC AAA AAA TTA GAT CAA AAA GAT CAG GTT AAT CAA GCT TTA
       H   S   D   Q   Q   N   K   K   L   D   Q   K   D   Q   V   N   Q   A   L
      181                                                                          240
      GAT ACT ATT AAC AAG GTA ASS GAA GAT GTT TCT AGT AAA TTA GAG GGA GTT AGA GAA TCA
       D   T   I   N   K   V   T   E   D   V   S   S   K   L   E   G   V   R   E   S
      241                                                                          300
      TCT CTT GAA TTG GTA GAA TCA AAT GAT GCA GGA ACT GTT GTT GCA TCA CAA GAA GCA ATG
       S   L   E   L   V   E   S   N   D   A   G   T   V   V   A   S   Q   E   A   M
      301                                                                          360
      TCT TTA ATG TCA GAT GTT GCT AAA GGG ACT GTT GTT GCT GAG GGT GCA AAC AAG GTT GTG
       S   L   M   S   D   V   A   K   G   T   V   V   A   E   G   A   N   K   V   V
      361                                                                          420
      GCA AAG TGC TCA GGA ATG GTT GCT GAG GGT GCA AAC AAG GTT GTT GAA ATG TCT AAA AAG
       A   K   C   S   G   M   V   A   E   G   A   N   K   V   V   E   M   S   K   K
```

FIG. 10-2

```
421                                                                          480
GCT GTT CAA GAA ASS CAA AAA GCT GTT TCT GTT GCT GGT GAA ACA TTT TTA ATA GAG
 A   V   Q   E   T   Q   K   A   V   S   V   A   G   E   T   F   L   I   E
481                                                                          540
AAG CAA ATA ATG TTA AAT AAA TCC CCA AAT AAT AAG GAA TTG GAA TTA ACA AAA GAA GAA
 K   Q   I   M   L   N   K   S   P   N   N   K   E   L   E   L   T   K   E   E
541                                                                          600
TTT GCT AAA GTG GAC GAA GTT AAA GAA ACT TTA ATG GCT TCT GAA AGG GCT TTG GAT GAA
 F   A   K   V   D   E   V   K   E   T   L   M   A   S   E   R   A   L   D   E
601                                                                          660
ACA GTT CAA GAG GCT CAA AAA AAA GAT GTT CTC AAT ATG GTT AAT GGT TTG AAT CCG TCA AAT AAG
 T   V   Q   E   A   Q   K   K   D   V   L   N   M   V   N   G   L   N   P   S   N   K
661                                                                          720
GAT CAA GTA TTA GCA AAA AAA GAT CGA AAG GCT ATT TCT AAT GTT GTT AAG GTA GCT
 D   Q   V   L   A   K   K   D   R   K   A   I   S   N   V   V   K   V   A
721                                                                          780
CAA GGC GCA AGA GAT CTT ACA AAA GTA ATG GCT ATT TCT TTA TAC ATG AGA TAG TTA GAT
 Q   G   A   R   D   L   T   K   V   M   A   I   S   L   Y   M   R  stop ATATAAATTTATAAATAATTAGAGGTTAAAGCAAAAGGTGGAAGCTAATT
GTATTAGTTCCTGCCCTTTTTATTTAATAATATAAGATCAATATTGACCCTCCCTATT
AAGGCTGTCCTTATGATATAATATATTCCGTTATGAATATTTACATTTCCA
ATATTTACTTGTTGCATATTTATCTTAACTAATAAAATTGCCTTAAGGA
                           1000
AGGAGAATTAATTTTTGAATAAAGAATA
```

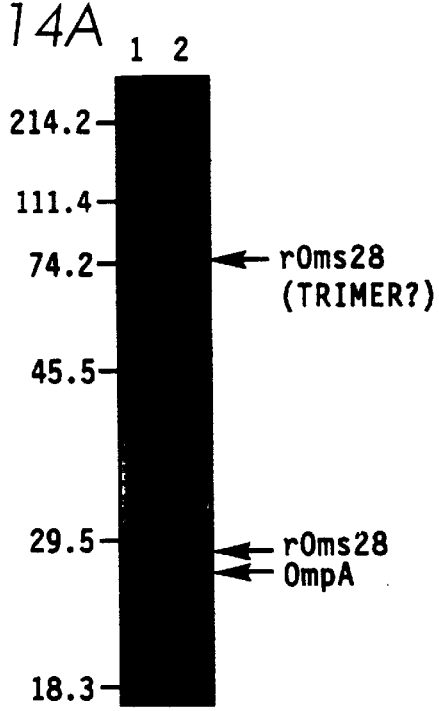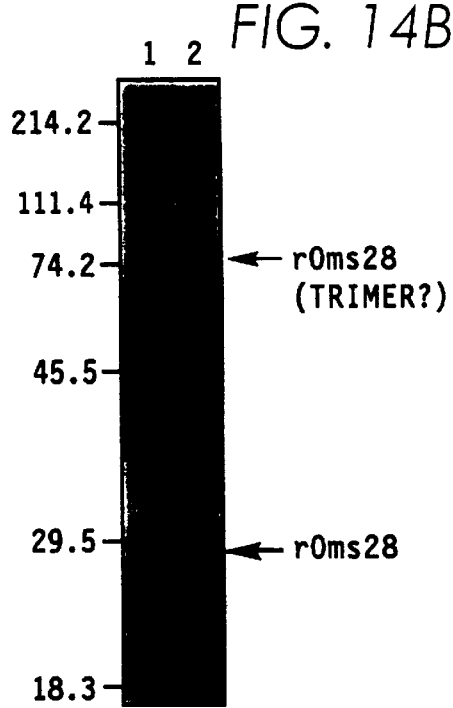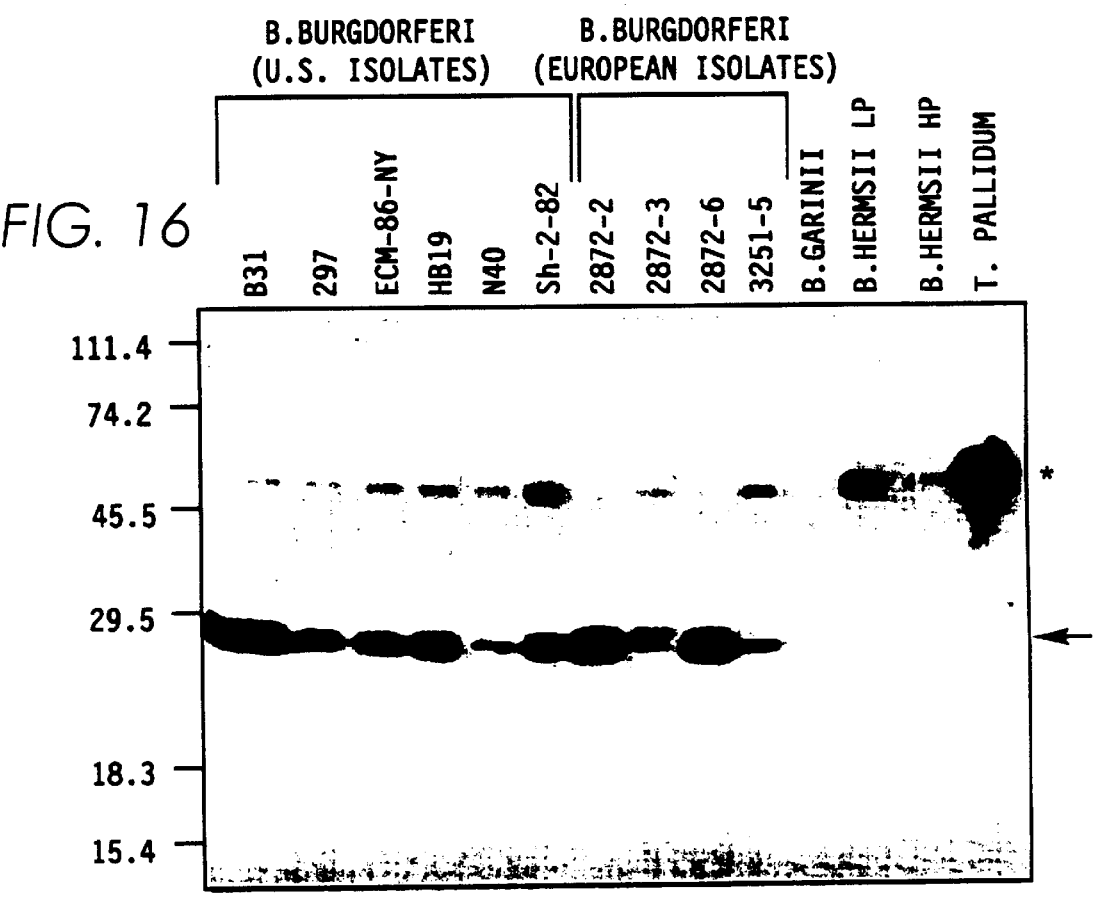

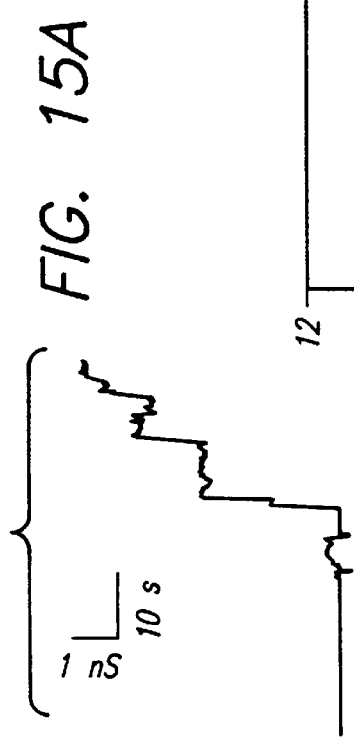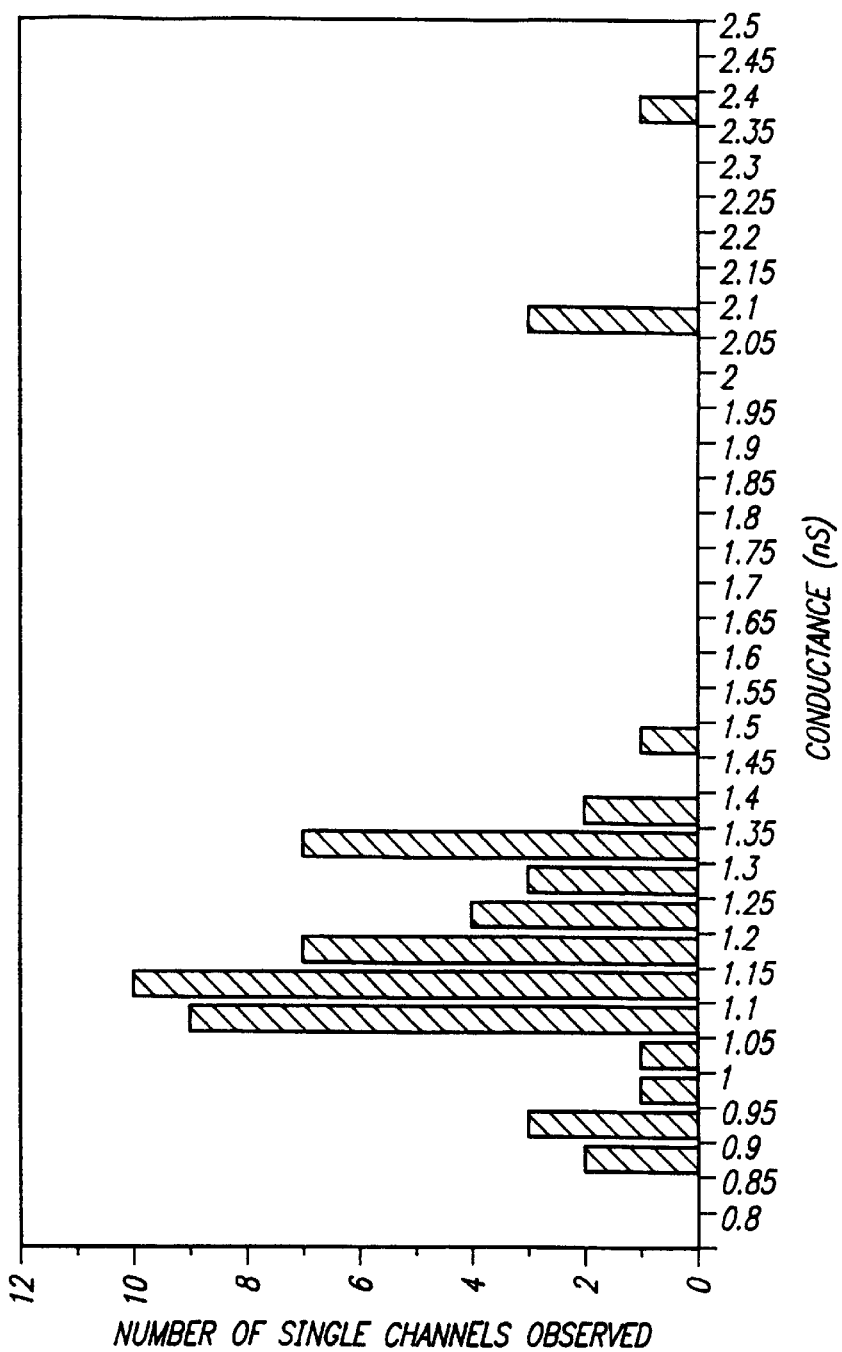
FIG. 15A
FIG. 15B

SEQUENCE LISTING

<160> NUMBER OF SEQ ID NOS: 9

<210> SEQ ID NO 1
<211> LENGTH: 1129
<212> TYPE: DNA
<213> ORGANISM: Borrelia burgdorferi

<400> SEQUENCE: 1

```
tttaaattaa aaaaagttaa attattaatt aattttatt taaatatgta ttggttctaa      60
tttagttatg ttttaaaata ataaaaataa atgtttaaat aaggagaatt aacaatgact    120
aaaatattta gtaatttaat aattaatgga ttattgtttg gatttgtaag tttaaatgtg    180
tttgcagatt ctaacaatgc aaatattctc aagcctcaat ccaatgtttt agaacactca    240
gatcaaaaag ataacaaaaa attagatcaa aaagatcagg ttaatcaagc tttagatact    300
attaacaagg taaccgaaga tgtttctagt aaattagagg gagttagaga atcatctctt    360
gaattggtag aatcaaatga tgcaggagta gttaaaaagt ttgtaggctc aatgtcttta    420
atgtcagatg ttgctaaagg gactgttgtt gcatcacaag aagcaactat tgtggcaaag    480
tgctcaggaa tggttgctga gggtgcaaac aaggttgttg aaatgtctaa aaaggctgtt    540
caagaaaccc aaaaagctgt ttctgttgct ggtgaagcaa cattttaat agagaagcaa    600
ataatgttaa ataaatcccc aaataataag gaattggaat taacaaaaga agaatttgct    660
aaagtggacg aagttaaaga aactttaatg gcttctgaaa gggctttgga tgaaacagtt    720
caagaggctc aaaaagttct caatatggtt aatggtttga atccgtcaaa taaggatcaa    780
gtattagcaa aaaaagatgt tcgaaaggct atttctaatg ttgttaaggt agctcaaggc    840
gcaagagatc ttacaaaagt aatggctatt tctttataca tgagatagtt agatatataa    900
atttataaat aattagaggt taaagcaaaa aggtggaagc taattgtatt agttcctgcc    960
tttttattt aataagatca atattgacct ccctattaag gctgtcctta tgatataata   1020
tatttccgtt atgaatattt acatttccaa tatttacttg ttgcatattt atatcttaac   1080
taataaaatt tgccttaagg aaggagaatt aattttgaa taaagaata                1129
```

<210> SEQ ID NO 2
<211> LENGTH: 257
<212> TYPE: PRT
<213> ORGANISM: Borrelia burgdorferi

<400> SEQUENCE: 2

```
Met Thr Lys Ile Phe Ser Asn Leu Ile Ile Asn Gly Leu Leu Phe Gly
  1               5                  10                  15

Phe Val Ser Leu Asn Val Phe Ala Asp Ser Asn Asn Ala Asn Ile Leu
             20                  25                  30

Lys Pro Gln Ser Asn Val Leu Glu His Ser Asp Gln Lys Asp Asn Lys
         35                  40                  45

Lys Leu Asp Gln Lys Asp Gln Val Asn Gln Ala Leu Asp Thr Ile Asn
     50                  55                  60

Lys Val Thr Glu Asp Val Ser Ser Lys Leu Glu Gly Val Arg Glu Ser
 65                  70                  75                  80

Ser Leu Glu Leu Val Glu Ser Asn Asp Ala Gly Val Val Lys Lys Phe
                 85                  90                  95

Val Gly Ser Met Ser Leu Met Ser Asp Val Ala Lys Gly Thr Val Val
            100                 105                 110

Ala Ser Gln Glu Ala Thr Ile Val Ala Lys Cys Ser Gly Met Val Ala
        115                 120                 125

Glu Gly Ala Asn Lys Val Val Glu Met Ser Lys Lys Ala Val Gln Glu
    130                 135                 140

Thr Gln Lys Ala Val Ser Val Ala Gly Glu Ala Thr Phe Leu Ile Glu
145                 150                 155                 160

Lys Gln Ile Met Leu Asn Lys Ser Pro Asn Asn Lys Glu Leu Glu Leu
                165                 170                 175

Thr Lys Glu Glu Phe Ala Lys Val Asp Glu Val Lys Glu Thr Leu Met
            180                 185                 190

Ala Ser Glu Arg Ala Leu Asp Glu Thr Val Gln Glu Ala Gln Lys Val
        195                 200                 205

Leu Asn Met Val Asn Gly Leu Asn Pro Ser Asn Lys Asp Gln Val Leu
    210                 215                 220

Ala Lys Lys Asp Val Arg Lys Ala Ile Ser Asn Val Val Lys Val Ala
225                 230                 235                 240

Gln Gly Ala Arg Asp Leu Thr Lys Val Met Ala Ile Ser Leu Tyr Met
                245                 250                 255

Arg
```

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence:PCR PRIMER

<400> SEQUENCE: 3
ggaattccat atgactaaaa tatttagtaa t                          31

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence:PCR PRIMER

<400> SEQUENCE: 4
cgcggatccg aattcctatc tcatgtataa agaaat                     36

-continued

```
<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence:PCR PRIMER

<400> SEQUENCE: 5
cgcggatcca gattctaaca atgcaaatat t                               31

<210> SEQ ID NO 6
<211> LENGTH: 15
<212> TYPE: PRT
<213> ORGANISM: Borrelia burgdorferi

<400> SEQUENCE: 6

Leu Asp Leu Thr Phe Ala Ile Gly Gly Thr Gly Thr Gly Asn Arg
 1               5                  10                  15

<210> SEQ ID NO 7
<211> LENGTH: 7
<212> TYPE: PRT
<213> ORGANISM: Borrelia burgdorferi

<400> SEQUENCE: 7

Tyr Lys Leu Gly Leu Thr Lys
 1               5

<210> SEQ ID NO 8
<211> LENGTH: 23
<212> TYPE: PRT
<213> ORGANISM: Borrelia burgdorferi

<400> SEQUENCE: 8

Ile Asn Asp Lys Asn Thr Tyr Leu Ile Leu Gln Met Gly Thr Asp Phe
 1               5                  10                  15

Gly Ile Asp Pro Phe Ala Ser
            20

<210> SEQ ID NO 9
<211> LENGTH: 11
<212> TYPE: PRT
<213> ORGANISM: Borrelia burgdorferi

<400> SEQUENCE: 9

Asp Thr Gly Glu Lys Glu Ser Trp Ala Ile Lys
 1               5                  10
```

BORRELIA BURGDORFERI OUTER MEMBRANE PROTEINS

This is a continuation of Ser. No. 08/787,367, filed Jan. 21, 1997 now abandoned, which was originally submitted as provisional application Serial No. 60/010,321, filed Jan. 22, 1996.

This invention was made with Government support through funding from the National Institutes of Health ("NIH") under NIH Grant Nos. Al 21352, Al 29733, Al 12601 and Al 37312. The Government has certain rights in this invention.

TECHNICAL FIELD OF THE INVENTION

This invention relates generally to membrane proteins and specifically to Borrelia burgdorferi membrane proteins, particularly outer membrane-spanning porin proteins, which are used to induce a protective immune response in animals. Such proteins can be used immunologically as vaccines for Lyme disease caused by this organism. Alternatively, diagnosis of Lyme disease can be performed by detecting the presence of the proteins, antibodies to the proteins, or polynucleotides which encode or can be translated into the proteins.

BACKGROUND OF THE INVENTION

Lyme disease is a tick-borne infection with worldwide distribution caused by Borrelia burgdorferi sensu lato. Borrelia burgdorferi sensu stricto (hereinafter referred to as "B. burgdorferi") initially causes a flu-like systemic illness that, if untreated, may develop into a disease characterized by arthritic, cardiac and neurological involvement {Steere, A. C., N. Eng. J. Med., 321:586–596 (1989)}. Although the clinical manifestations of Lyme disease have been well documented, basic knowledge relating the pathogenesis of Lyme borreliosis to specific molecular components, specifically outer membrane (OM) proteins, has been lacking due primarily to the lability of the OM of B. burgdorferi {Luft, B. J., Infect. & Immun., 57:3637–3645 (1989)}. Since OM proteins presumably mediate the host/pathogen interaction, identification and characterization of these molecules may provide important insights into the molecular pathogenesis of Lyme disease.

There are two distinct features of the outer membrane of pathogenic spirochetes which have hindered the characterization of their constituent outer membrane proteins. The outer membrane of pathogenic spirochetes are extremely labile, resulting in the loss of a significant amount of the outer membrane, even under the mildest experimental conditions. In addition, this labile outer membrane of B. burgdorferi has been shown by freeze fracture electron microscopy to contain at least 5-fold less transmembrane outer membrane proteins than that of typical enteric gram negative bacteria {Walker, E. M., et al., J. Bacteriol., 173:5585–5588 (1991)}. This fragility of the outer membrane and paucity of outer membrane proteins has made the application of standard outer membrane purification techniques to spirochetes unsuccessful.

The majority of molecular studies pertaining to Lyme disease have focused on lipoproteins designated Osp which are localized to both the inner and outer membrane of B. burgdorferi {Brusca, J. S., et al., J. Bacteriol., 173:8004–8008 (1991); Norris, S. J. et al., Infect. Immun., 60:4662–4672 (1992)}. Proteins that span the OM of B. burgdorferi, or OM-spanning ("Oms") proteins have only been visualized by freeze-fracture electron microscopy {Walker, E. M., et al., J. Bacteriol., 173:5585–5588 (1991); Radolf, J. D., et al J. Bacteriol., 176:21–31 (1994)} and have not been molecularly characterized.

SUMMARY OF THE INVENTION

The present invention presents B. burgdorferi membrane proteins such as outer membrane porin proteins: Oms28, Oms45, and Oms66. Oms28, Oms45, and Oms66 each have molecular masses of about 28, 45, and 66 kDa respectively and average single channel conductances of about 0.6, 0.22, and 9.7 nS, respectively. Also disclosed are the methods for purifying these proteins from B. burgdorferi, methods for producing antibodies to these proteins, and the resulting antibodies. These proteins and their immunogenic fragments may function as vaccine candidates to protect against Lyme borreliosis, and antibodies capable of binding to them may have bactericidal activity against pathogenic B. burgdorferi. These proteins and the antibodies specific for them could be used in diagnostic assays for Lyme disease. Further disclosed are the nucleotide and amino acid sequences, the cloning of the genes encoding these proteins, e.g. native or recombinant proteins, and methods for obtaining the foregoing. Also included in the present invention are other B. burgdorferi outer membrane proteins obtainable by the isolation and purification methods of the present invention.

Figure 1A:
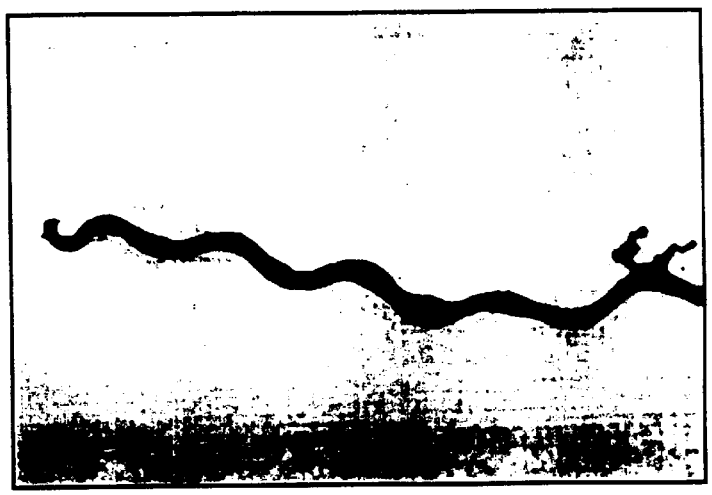
FIG. 1 presents removal of the B. burgdorferi outer membrane with 25 mM citrate buffer pH 3.2.
  (A) Electron micrograph of B. burgdorferi B31 passage 10. Bar equals 0.5 μm.
  (B) Electron micrograph of B. burgdorferi B31 passage 10 incubated with 25 mM citrate buffer pH 3.2 for 20 minutes at room temperature. Bar equals 0.5 μm.
  (C) Outer membrane vesicles ("OMV") isolated from B. burgdorferi B31 passage 10. Bar equals 0.5 μm.

Numbers to the left indicate the molecular masses of protein markers (in kDa).

(A) OMV derived from 5×10$^9$ B31 passage 10 *B. burgdorferi*.

(B) OMV derived from 5×10$^9$ B31 passage 48 *B. burgdorferi*.

(C) OMV derived from 5×10$^9$ B31 avirulent ATCC *B. burgdorferi*.

FIG. 4 presents antigenicity of hydrophobic outer membrane (OM) proteins from *B. burgdorferi* OMV. The nomenclature used is as described in FIG. 3. Identical amounts of Triton X-114 detergent phase OM proteins were separated by 2D gel electrophoresis and immunoblotted as described in Example 1. The immunoblot was incubated in infection-derived rabbit serum adsorbed with avirulent ATCC B31 *B. burgdorferi* as described in the Methods of Example 1.

(A) OMV derived from 5×10$^9$ B31 passage 10 *B. burgdorferi*.

(B) OMV derived from 5×10$^9$ B31 passage 48 *B. burgdorferi*.

(C) OMV derived from 5×10$^9$ B31 avirulent ATCC *B. burgdorferi*.

FIG. 5 presents surface exposure of virulent strain-associated outer membrane proteins. Immunoelectron micrographs of B31 *B. burgdorferi* reacted with various rabbit sera. All micrographs shown are identical in magnification. Bar equals 0.5 μm.

(A) *B. burgdorferi* B31 passage 1 incubated with basal (pre-immune) serum.

(B) *B. burgdorferi* B31 passage 1 incubated with unadsorbed immune rabbit serum (IRS).

(C) *B. burgdorferi* B31 passage 1 incubated with avirulent B31 ATCC adsorbed immune rabbit serum (aIRS).

(D) *B. burgdorferi* B31 passage 50 incubated with avirulent B31 ATCC adsorbed immune rabbit serum (aIRS).

(E) *B. burgdorferi* B31 avirulent ATCC incubated with avirulent B31 ATCC adsorbed immune rabbit serum (aIRS).

FIG. 6 presents identification of outer membrane-associated lipoproteins. B31 passage 5 *B. burgdorferi* and avirulent ATCC were intrinsically labeled with [$^3$H] palmitate as described in Example 1. OMV and whole cells were isolated, incubated with TX-114, and their detergent phase proteins analyzed by 2D electrophoresis, followed by autoradiography.

(A) OMV derived from 5×10$^9$ B31 passage 5 *B. burgdorferi*.

(B) OMV derived from 5×10$^9$ B31 avirulent ATCC *B. burgdorferi*.

(C) 5×10$^8$ B31 passage 5 *B. burgdorferi* whole cells. Numbers with asterisks refer to proteins not observed in the OMV samples. Nomenclature used is identical to that described in FIG. 3. Molecular masses of markers are indicated to the left (in kDa).

FIG. 7 presents porin activity associated with the *B. burgdorferi* B31 OMV.

(A) Solubilized OMV were added to the bilayer at the time designated by the arrow. Step-wise conductances between 12–13 nS were observed. (inset) Observation of both the 12–13 nS porin and a minor 0.6 nS porin. The first arrow shows an increase of the membrane potential from 0 to +30 mV. The second arrow indicates the time of sample addition.

(B) Histogram showing the conductance of the small porin (0.6 nS). Total number of single channel insertions was 97.

(C) Histogram showing the conductance of the large porin (12–13 nS). Total number of single channel insertions was 348.

FIG. 8 presents identification of a 0.6 nS porin activity from *B. burgdorferi*.

(A) Triton X-100 solubilized protein from 3×10$^9$ *B. burgdorferi* B31 passage 7 whole cells separated by two dimensional (2D) gel electrophoresis. The proteins were resolved by non-denaturing isoelectric focusing (ND-IEF) gel electrophoresis in the first dimension and by SDS-10% polyacrylamide gel electrophoresis (SDS-10% PAGE) in the second dimension. Numbers to the left represent molecular weight markers (in kDa). Lines on the bottom represent each of the 24 separate pieces that were tested for porin activity following the elution of protein from the ND-IEF gel. Arrows denote gel fragments that demonstrated porin activity.

(B) Single channel conductance observed in the active fractions from the ND-IEF gel.

Figures 9A, 9B:
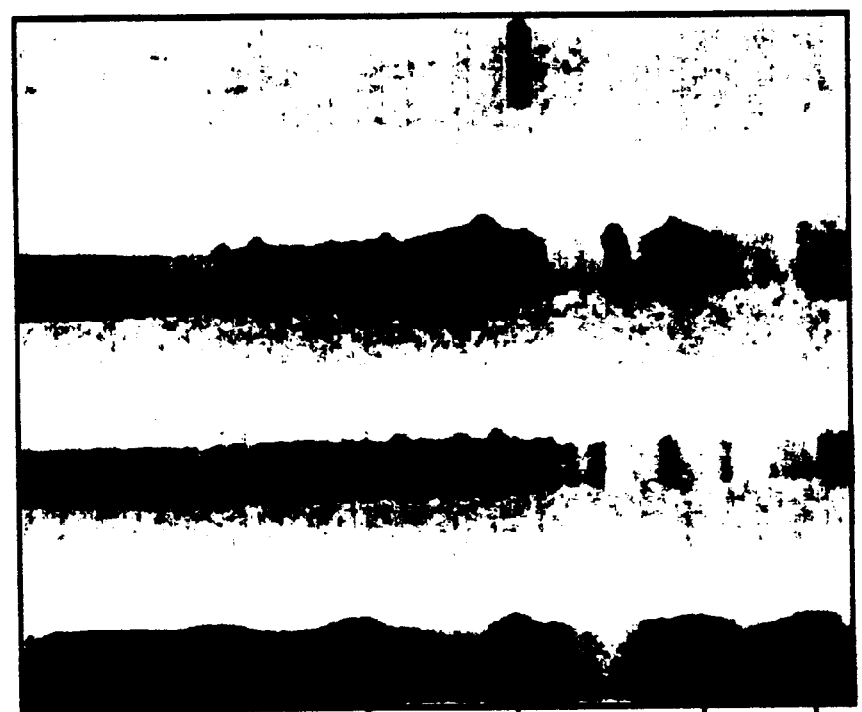

FIG. 9 presents FPLC purification and porin activity of native Oms28.

(A) Amido black stained blot showing the purification of Oms28.
Lane 1, protein molecular weight standards (in kDa).
Lane 2, 10$^8$ *B. burgdorferi* strain B31 passage 3 whole cells.
Lane 3, OMV derived from 2.5×10$^9$ *B. burgdorferi* strain B31 passage 3 whole cells.
Lane 4, Oms28 purified from OMV derived from 2.5×10$^{10}$ *B. burgdorferi* strain B31 passage 3 whole cells.

(B) Immunoblot of FPLC and gel purified Oms28 probed with Oms28 antiserum.
Lane 4, Oms28 purified from OMV derived from 8×10$^9$ *B. burgdorferi* strain B31 passage whole cells.

(C) Single channel conductance of purified native Oms28. Purified Oms28, at a concentration of 0.4 ng/ml, was added to a planar lipid bilayer bathed in 1 M KCl, 5 mM HEPES pH 7.4.

(D) Histogram of the single channel conductance events observed for purified native Oms28 (n=181).

FIG. 10 presents nucleotide sequence of the oms28 gene and deduced amino acid sequence of Oms28 from *B. burgdorferi* (also identified as SEQ ID NOS 1 and 2, respectively). Numbers shown are relative to the start of the oms28 open reading frame. The oms28 locus encodes a 257 amino acid protein with a putative 24 amino acid leader peptidase I signal sequence. The predicted cleavage site is denoted by a vertical arrow between residues 24 and 25. The putative ribosome binding site (RBS) is underlined in bold and putative −35 and −10 σ$^{70}$ promoter regions are underlined. Dotted lines with arrows represent a rho-independent potential transcription termination signal. Underlined amino acids correspond exactly to sequences obtained following proteolytic digestion of Oms28 with trypsin.

FIG. 11 presents putative outer membrane topology of Oms28. Boxes represent single amphipathic beta pleated transmembrane segments that are proposed to span the outer membrane. Designations for membrane-spanning domains are based on hydrophobic moment plot analysis. Sequences above the boxed region represent the proposed surface exposed loops. Sequences below the boxed region represent loops that are exposed to the periplasmic space.

Figure 12:
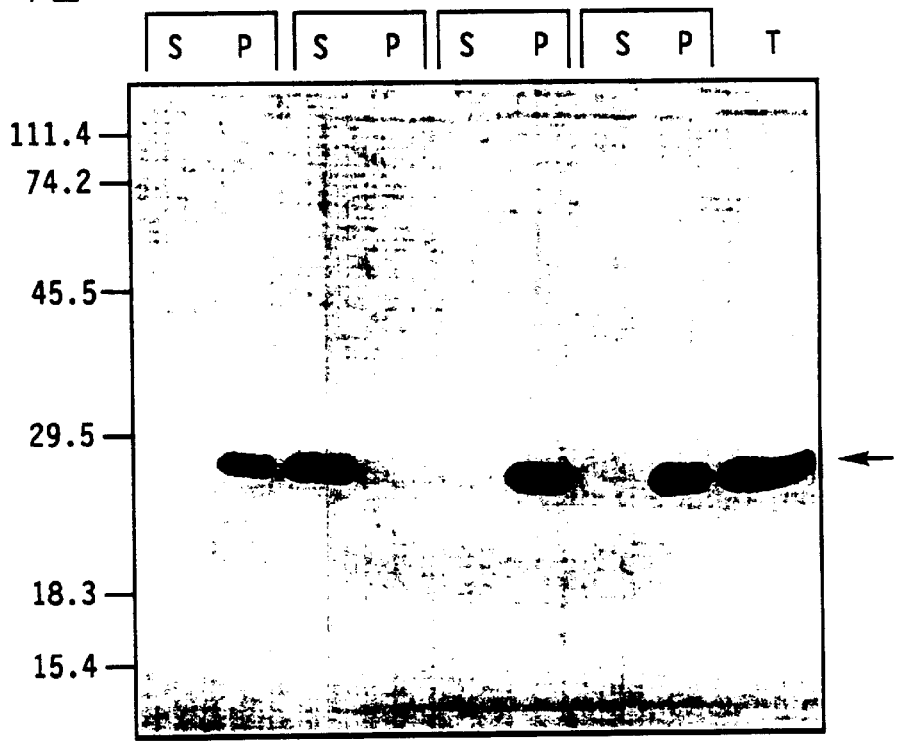

FIG. 12 presents an association of Oms28 with the outer membrane vesicle preparations. OMV derived from 1.25× 10$^9$ *B. burgdorferi* strain B31 passage 3 were washed for 5 minutes with salt solutions to determine if Oms28 was a membrane-spanning protein. P and S refer to pellet and supernatant, respectively, following a 1 hour centrifugation at 40,000 g. Protein samples corresponding to the P and S samples were separated by SDS-polyacrylamide gel electrophoresis, immunoblotted to a PVDF membrane, and probed with antiserum specific for Oms28. Numbers to the left represent the molecular mass of protein standards (in kDa). Arrow at right denotes location of Oms28. PBS, OMV incubated with PBS pH 7.4; TX-100, NaCl, OMV solubilized with 1% Triton X-100, then incubated with 1M NaCl; NaCl, OMV incubated in 1 M NaCl; $Na_2CO_3$, OMV incubated in 0.1 M $Na_2CO_3$, pH 11.0; T, total untreated, unpelleted OMV.

Figure 13A:
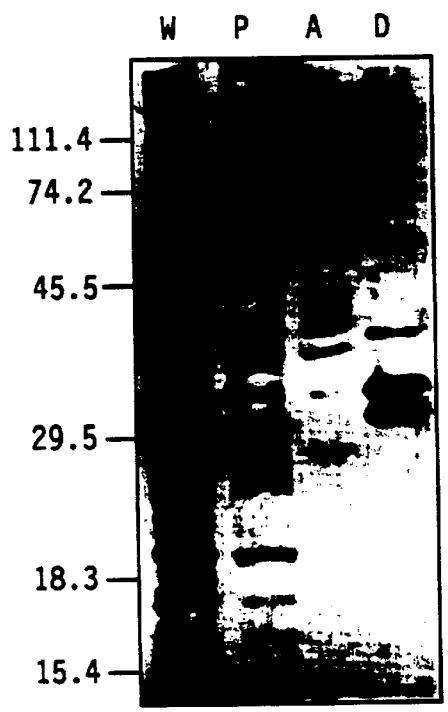
Figure 13B:
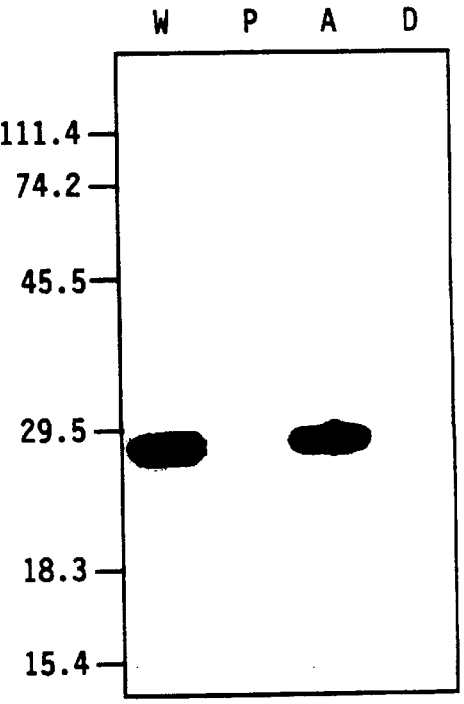
Figure 17:
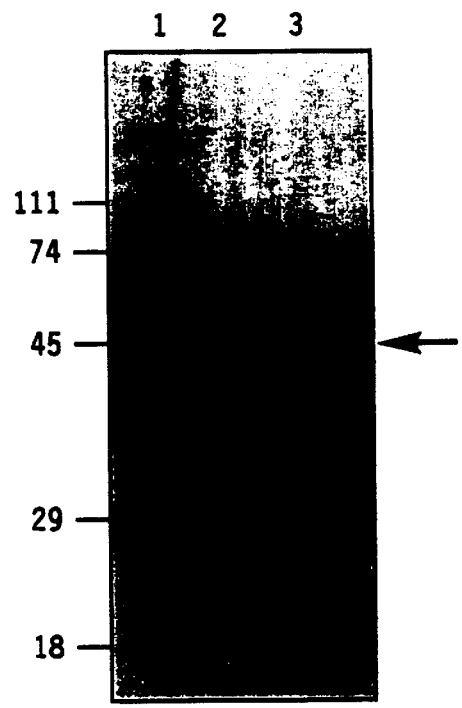

FIG. 13 presents Triton X-114 extracted and phase partitioned material from $10^8$ *B. burgdorferi* strain B31 passage 6 whole cells.

(A) Amido-black stained immunoblot for ECL analysis.

(B) Immunoblot shown in panel A probed with antiserum specific for Oms28. Numbers to the left represent the molecular mass of protein standards (in kDa).

FIG. 14 presents localization of recombinant Oms28 to the outer membrane (OM) of *E. coli*.

(A) Coomassie brilliant blue stained SDS-polyacrylamide gel containing OM derived from 5 $OD_{600}$(ml) equivalents of BL21 DE3 pLysE, pET17b (lane 1) and BL21 DE3 pLysE pET17boms28 overproducing recombinant Oms28 (lane 2).

(B) Immunoblot of the identical samples shown in panel A probed with Oms28 antiserum. Numbers to the left represent the molecular mass of protein standards (in kDa). Arrows denote the location of the *E. coli* OmpA protein and the monomeric and oligomeric forms of recombinant Oms28.

FIG. 15 presents porin activity of recombinant Oms28 (r-Oms28).

(A) Single channel conductance of r-Oms28. Gel eluted r-Oms28, at a concentration of approximately 10 ng/ml, was incubated in a planar lipid bilayer system containing 1 M KCl.

(B) Histogram of the single channel conductance events observed for purified r-Oms28 (n=54).

FIG. 16 presents the presence of Oms28 or Oms28 homologues in various international *B. burgdorferi* isolates and other pathogenic spirochetes. Protein derived from $5 \times 10^7$ whole cells was separated by SDS-polyacrylamide gel electrophoresis, immunoblotted to a PVDF membrane, and probed with antiserum specific for the strain B31 Oms28 protein. The brackets denote whether the *B. burgdorferi* isolate is associated with the United States or Europe. The American samples shown were all passage 1 virulent isolates. The European strains tested were virulent isolates that had been passaged no more than 15 times. Lanes containing protein from other spirochetes are labeled accordingly. Numbers to the left represent the molecular mass of protein standards (in kDa). An arrow denotes the location of Oms28 observed in the *B. burgdorferi* strain B31 and an asterisk marks the location of contaminating levels of rabbit immunoglobulin heavy chain.

Figure 17:
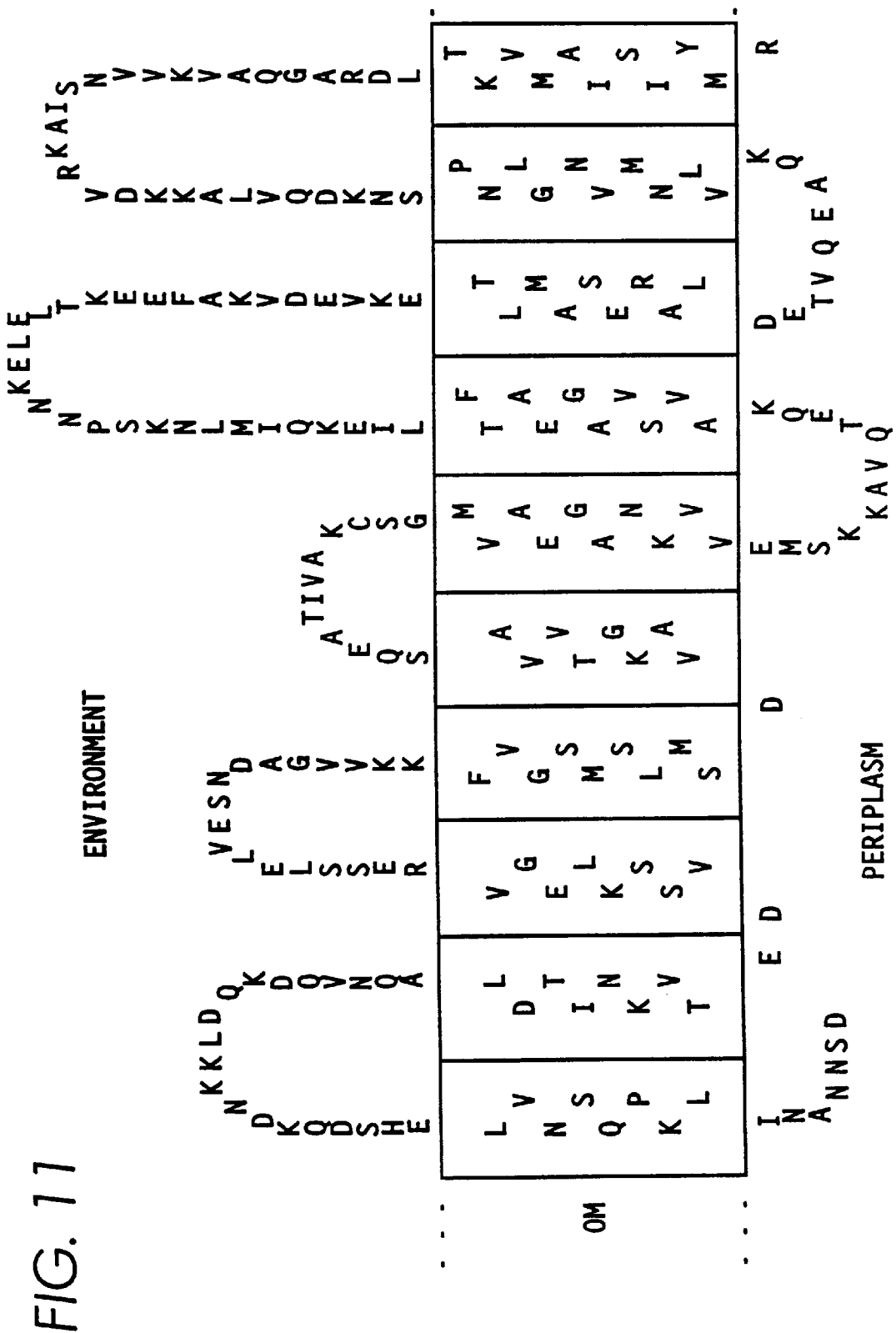

FIG. 17. presents purification of Oms45. Oms45 was purified by Mono Q anion FPLC separation of the detergent phase of whole organisms extracted with 1% Triton X-114. Amido black stain of $1 \times 10^8$ whole *B. burgdorferi* 31 (lane 1), $1 \times 10^8$ equivalence of Triton X-114 detergent phase (lane 2) and $7 \times 10^{10}$ equivalence of Mono Q FPLC purified Oms45.

Figure 18B:
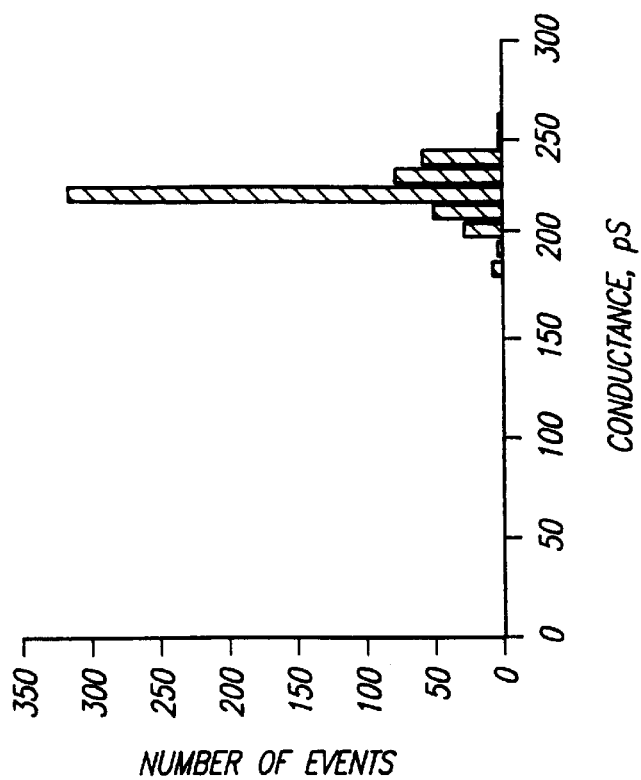
Figure 18A:
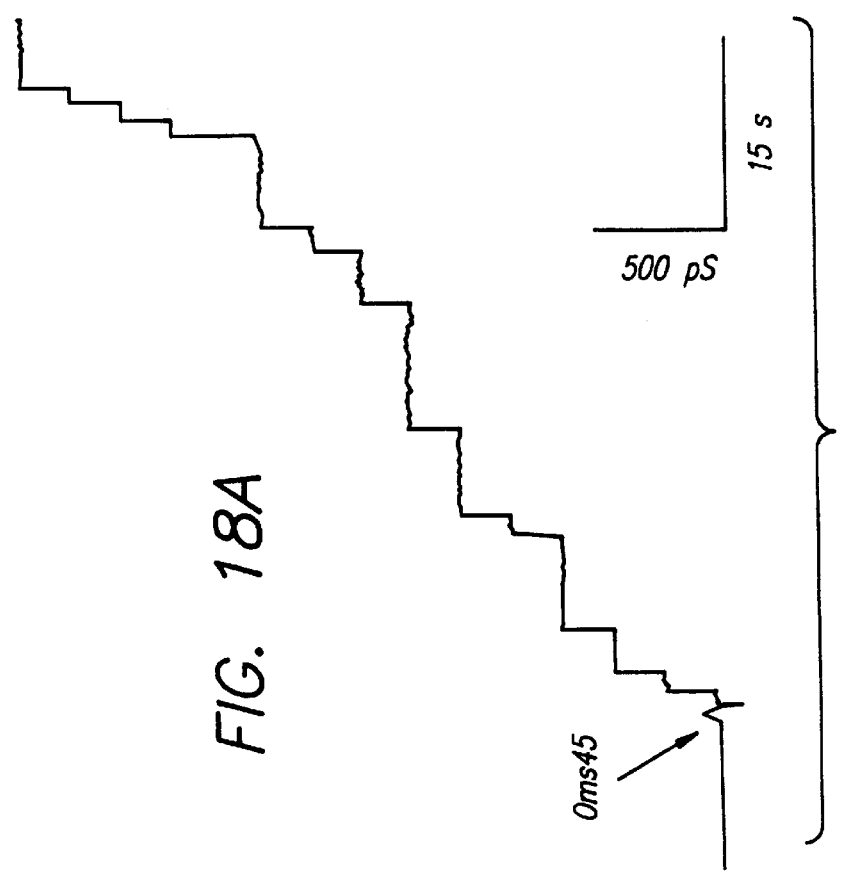

FIG. 18 presents porin activity of Oms45. Black lipid bilayer assay of purified Oms45.

(A) Step increases in conductance at 50 mV after the addition of purified Oms45.

(B) Histogram of single channel conductance increases over 500 observed insertional events. The average single channel conductance was 0.22 nS (220 pS).

FIG. 19 presents localization of Oms28 in fractionated *Escherichia coli* BL21 DE3 pLysE expressing oms28.

(A) Coomassie blue stained SDS-9% polyacrylamide gel of whole cells with the vector pET17b alone induced with isopropylthio-β-D-galactoside (IPTG) for 1 hour and rifampicin for an additional 2 hours (lane 1), whole cells containing oms28, uninduced (lane 2), whole cells expressing oms28 as indicated above (lane 3), soluble protein from whole cells expressing oms28 (lane 4), inner membrane fraction from cells expressing oms28 (lane 5), outer membrane fraction from cells expressing oms28 (lane 6). Arrow denotes the location of oms28 and asterisks mark the location of *E. coli* porin proteins.

(B) Immunoblot of samples identical to that shown in panel A probed with Oms28 antisera.

DETAILED DESCRIPTION OF THE INVENTION

The present invention presents *B. burgdorferi* membrane proteins such as outer membrane porin proteins: Oms28, Oms45, and Oms66. Oms28, Oms45, and Oms66 each have molecular masses of about 28, 45, and 66 kDa respectively and average single channel conductances of about 0.6, 0.22, and 9.7 nS, respectively. Also disclosed are the methods for purifying these proteins from *B. burgdorferi*, methods for producing antibodies to these proteins, and the resulting antibodies. These proteins and their immunogenic fragments may function as vaccine candidates to protect against Lyme borreliosis, and antibodies capable of binding to them may have bactericidal activity against pathogenic *B. burgdorferi*. These proteins and the antibodies specific for them could be used in diagnostic assays for Lyme disease. Further disclosed are the nucleotide and amino acid sequences, the cloning of the genes encoding these proteins, e.g. native or recombinant proteins, and methods for obtaining the foregoing. Also included in the present invention are other *B. burgdorferi* outer membrane proteins obtainable by the isolation and purification methods of the present invention, particularly those described in the "EXAMPLES" section below.

More specifically, the present invention presents the cloning and sequencing of the oms28 gene and the deduced amino acid sequence of the Oms28 protein (FIG. 10). oms28 is the first gene to be cloned and sequenced that encodes a functional Oms protein. Oms28 is not expressed by other spirochetes including *B. garinii, B. hermsii,* and *Treponema pallidum* subspecies *pallidum* (hereinafter referred to as "*T. pallidum*"). Oms28 thus appears to be specific to *B. burgdorferi* sensu stricto.

Oms45 was purified to homogeneity. As far as the applicants are aware, neither the porin activity of Oms45 nor the nucleotide sequence of oms45 has been reported by others.

Peptides from trypsin digested Oms66, a peptide sequence of 15 amino acid residues at the N-terminal, were also sequenced and homology searches indicated that it completely matched the deduced complete amino acid sequence of a protein designated p66, deposited on May 26, 1995, by Sven Bergstrom with GenBank (with accession number X87725). Probert, W. S., et al., *Infect. Immun.*, 63:1933–1939 (1995) also discloses a 15 amino acid residue of the same sequence at the amino terminal of a protein designated p66. None of these two references disclose that the protein has porin activity. Skare, J., et al., {*J. Clin. Investigation*, 96:2380–2392 (1995)} (herein incorporated by reference in its entirety) describes the isolation of the *B. burgdorferi* outer membrane and the porin activities in the OMV derived from *B. burgdorferi*. The relevant part the article is found in Example 1, below. The article reported the large porin (designated herein as Oms66) as having a single channel conductance of 12.6 nS. However, in the present application, Oms66 was further purified and the activity was determined to be 9.7 nS.

Surprisingly, Oms28 and Oms66 partition into the aqueous phase either in whole (Oms28) or in part (Oms66) of *B. burgdorferi* Triton X-114 extracts. On the other hand, Oms45 is found exclusively in the detergent phase of *B. burgdorferi* Triton X-114 extracts. Protease inhibitors were used during the detergent solubilization and purification of these Oms porin proteins.

Extraction of outer membrane proteins from whole cells of *B. burgdorferi* using the nonionic detergent Triton X-114 (TX-114), resulted in the isolation of a number of detergent phase proteins, including Oms45. Extraction of proteins from whole cells of *B. burgdorferi* using nonionic detergent TX-100, resulted in the solubilization of a number of proteins, including Oms28 and Oms66. Oms45, Oms28 and Oms66 are further purified using fast performance liquid chromatography (FPLC). The amino acid and nucleotide sequences of the purified proteins may be obtained, e.g., using the methods described in the "EXAMPLES" section, below. The purified proteins are separated by SDS-polyacrylamide gel electrophoresis, then transferred to a nitrocellulose membrane and digested with trypsin. Tryptic peptides derived from the purified proteins are preferably purified by reverse-phase high performance liquid chromatography (RP-HPLC) and sequenced. Based upon the amino acid sequence, degenerate oligonucleotide probes may be synthesized for each of the proteins. *B. burgdorferi* genomic DNA library may be probed with the oligonucleotides and inserts identified as containing the coding sequence for Oms28, Oms45, and Oms66, respectively. Alternatively, degenerate oligonucleotides could be used to probe genomic digests of *B. burgdorferi* DNA to identify DNA fragments encoding Oms28, Oms45 and Oms66. Recombinant Oms28 was produced in *Escherichia coli* in order to generate specific rabbit antisera. Recombinant Oms45 and Oms66 may be produced using methods known in the art, preferably similar to the method described in Example 2, below.

Oms28, Oms45, and Oms66 can be identified in different *Borrelia genus* (hereinafter referred to as "Borrelia") by their immunoreactivity with antibodies raised against the Oms28, Oms45, and Oms66 described in or derived from (e.g. as recombinant proteins or antigenic fragments) the "EXAMPLES" section, below. Immunoblot studies may be conducted to determine whether there is a strong correlation between Borrelia, *B. burgdorferi* sensu lato, or *B. burgdorferi* sensu stricto (the latter is hereinafter referred to as *B. burgdorferi*) pathogenicity and reactivity with antisera specific for either Oms28, Oms45, or Oms66. Further, immunoblot and immunohistochemical studies may be conducted to determine whether Oms28, Oms45, and Oms66 (or proteins isolated and purified by the methods of the present invention) are present and specific for Borrelia, *B. burgdorferi* sensu lato, or *B. burgdorferi*. An immunoblot assay may be conducted, for example, similar to that described in Example 2, below, under "Presence of Oms28" in other American and European *B. burgdorferi* isolates. Similarly, hybridization assays may be conducted to determine whether Oms28, Oms45, and Oms66 nucleotide sequences are specific to Borrelia, *B. burgdorferi* sensu lato, or *B. burgdorferi*, under moderate or stringent hybridization assay conditions. The nucleotide and amino acid sequences may also be compared with that of other organisms (such as by computer sequence comparison using databases such as that of GenBank) to determine their homology or specificity vis-a-vis other organisms. In the following discussion, for convenience, only Borrelia is mentioned. However, one skilled in the art would understand that according to the specificities of the Oms28, Oms45, and Oms66 proteins, antibodies, and nucleotide sequences, they may be used in relation to Borrelia, Borrelia sensu lato, and/or *B. burgdorferi*, in the following discussion, e.g. in regard to diagnostic tests, therapeutics and vaccines. For example, Oms28 appears specific for *B. burgdorferi* based on the findings of Example 2, below. In the present invention, *B. burgdorferi* sensu lato refers to species of Borrelia that cause Lyme disease or diseases resembling Lyme disease; such species include *B. garinii*, *B. afzelii*, and *B. burgdorferi*. In the most preferred embodiment of the invention, the proteins (e.g. Oms28, Oms45, and Oms66), their antibodies, and nucleotide sequences will be used to detect *B. burgdorferi*, treat and vaccinate against Lyme disease. In the following discussion, Oms28, Oms45, and Oms66 proteins are exemplified. However, within the scope of this invention are also other Oms proteins and nucleotide sequences obtainable by the methods of the present invention, in particular those described in the "EXAMPLES" section, and the inventions relating to them as they are used in addition to or in place of Oms28, Oms45, and Oms66 proteins in the following discussion.

Unless otherwise modified, the term "protein" as used herein encompasses both native and synthetic polypeptides and peptides. Synthetic protein includes recombinant and chemically synthesized proteins and proteins produced by a cell-free in vitro translation system. Unless otherwise indicated, "Oms28", "Oms45" and "Oms66" proteins include both their native and synthetic versions.

The nucleotide sequences disclosed in FIG. 10 is in the form of DNA. However, based on the disclosed sequences, one skilled in the art could determine their complementary DNA and RNA sequences, and the RNA sequences complementary to the foregoing. Thus, the term "nucleotide sequence" includes both the DNA and RNA sequences. Further, as used in this application, the SEQ ID Nos. and disclosed nucleotide sequences include: (1) the DNA sequences as disclosed, (2) the nucleotide sequences (which may be RNA or DNA) complementary to the disclosed sequences, (3) the corresponding RNA sequences to the DNA sequences wherein the Thymidine (T) in the disclosed DNA sequences is replaced with Uracil (U), (4) nucleotide sequences wherein other nucleotides known in the art such as nucleotide analogs, replace those in the foregoing sequences, for example, 5-methyl-cytosine replacing cytosine, and (5) nucleotide sequences that are equivalent, e.g., those within about a 10%, or preferably a 20%, variance to the respective nucleotide sequences.

Since nucleotide codons are redundant, also within the scope of this invention are equivalent nucleotide sequences which include: nucleotide sequences which code for or can be translated into Oms28, Oms45, and Oms66; their protein variants, functional equivalents, or derivatives. These nucleotide sequences may also be used in the practice of the invention.

In addition to the above, Oms28, Oms45, and Oms66 nucleotide sequences also include: (1) nucleotide sequences that are capable of hybridizing to the coding sequences of the respective nucleotide sequences, under stringent hybridization conditions, and (2) fragments of or mutagenized nucleotide sequences of those disclosed herein which (a) encode or can be translated into proteins having substantially the same biological characteristics/activities of Oms28, Oms45, and Oms66, respectively; or (b) are able to induce a cellular and/or humoral response in an animal vaccinated with the nucleotide sequences. Preferably, the determinative biological characteristic/activity is the retention of at least one immunoepitope. Preferably, when used in an immunoassay for Borrelia, these proteins are immunoreactive with antibodies directed to Borrelia but not immunoreactive with antibodies directed against other antigens not specific to Borrelia found in a biological sample. More preferably, these proteins are immunoreactive with antibodies specific to Borrelia sensu lato, and most preferably *B. burgdorferi*.

As herein defined, a "biological sample" can be a biological fluid or tissue sample. Examples of a biological fluid sample include: blood, serum, plasma, synovial, and cerebro-spinal fluid. Examples of a biological tissue sample include tissue samples from the liver and kidney and tissue of endothelial origin. A biological sample can also include feces and discharge. Thus, for example, immunohistochemical assay can be conducted on these tissue samples. Preferably, these samples are from mammals, such as humans, wild or domestic mammals. More preferably, these proteins and the immunoassays can additionally distinguish between Borrelia and other spirochetes. More preferably, these proteins and immunoassays are specific for Borrelia sensu lato, and most preferably *B. burgdorferi*. Alternatively, the fragments of nucleotide sequences can be nucleotide probes of at least 20 nucleotides in length. Preferably, when used in a hybridization assay for Borrelia, under moderate to stringent hybridization condition, these probes do not detectably hybridize to the nucleotide sequences of non-Borrelia organisms which are found in a biological sample. More preferably, these hybridization assays are specific for Borrelia sensu lato, and most preferably *B. burgdorferi*; particularly under moderate to stringent hybridization condition. For example, when used to assay a biological sample, these probes do not detectably bind to non-specific nucleotide sequences found in a biological sample. Most preferably, these nucleotide sequences and the hybridization assays can additionally distinguish between pathogenic *B. burgdorferi* and non-pathogenic *B. burgdorferi*.

Alternatively, the nucleotide sequences hybridize to at least 10 consecutive nucleotides in the coding sequences of the above nucleotide sequences. The nucleotide sequences include a nucleotide sequence which encodes a protein containing at least 8; more preferably, 5 to 6; and most preferably, 4 amino acids. Preferably, the protein is specific to Borrelia, more preferably Borrelia sensu lato, and most preferably *B. burgdorferi*. Alternatively, the protein retains one or more biological functions of Borrelia, more preferably Borrelia sensu lato, and most preferably *B. burgdorferi*.

The terms "Oms28", "Oms45", and "Oms66", as used in relation to proteins are, respectively, as defined above, together with: (1) protein variants containing amino acid sequences that have for example, at least 95%, more preferably at least 70% of their amino acids matching the sequences disclosed herein, excluding their signal peptides, respectively; (2) the functional equivalents of these proteins and their variants, respectively; and (3) the derivatives, including fragments, of Oms28, Oms45, and Oms66 proteins and their variants, respectively.

Preferably, when used in an immunoassay for Borrelia, these proteins are immunoreactive with antibodies directed to Borrelia but not detectably immunoreactive with non-Borrelia specific antibodies found in a biological sample, and other spirochetes. More preferably, these proteins and immunoassays are specific for Borrelia sensu lato, and most preferably *B. burgdorferi*.

More preferably, these proteins and the immunoassays can additionally distinguish between pathogenic *B. burgdorferi* and non-pathogenic *B. burgdorferi*. Alternatively, or additionally, these proteins retain one or more biological functions of Borrelia, preferably Borrelia sensu lato, and most preferably *B. burgdorferi*. Thus, preferably, the fragment of these proteins claimed in this application contains at least one immunogenic epitope of Borrelia, preferably Borrelia sensu lato, and most preferably *B. burgdorferi*. Another example of a fragment is one which is capable of being bound by polyclonal antibodies directed to *B. burgdorferi*. In the case of antibodies which recognize linear epitopes, they generally bind to epitopes defined by about 3 to 10 amino acids.

Alternatively or additionally, these proteins possess the ability to induce a cellular and/or humoral response in an animal vaccinated with the proteins. More preferably, the cellular and/or humoral response is directed against Borrelia, preferably Borrelia sensu lato, more preferably *B. burgdorferi*, and most preferably pathogenic *B. burgdorferi*. Most preferably, animals vaccinated with these proteins are immunized against disease caused by Borrelia, preferably Borrelia sensu lato, or more preferably *B. burgdorferi* (such as Lyme disease) or such vaccinations ameliorate the disease in infected animals. The animal is preferably a mammal. More preferably, the animal is a human or a domestic animal. Alternatively, these proteins or their amino acid sequences are derived from the membrane proteins of *B. burgdorferi* and are immunoreactive with antibodies raised against the Oms28, Oms45, and/or Oms66 disclosed in the "EXAMPLES", below.

The variants can result from, e.g. substitution, insertion, or deletion of one or more amino acids from the amino acid sequences of Oms28, Oms45, and/or Oms66. The derivatives of the proteins and their variants, include fragments of these proteins and their immunogenic epitopes. As described above, preferably, too, each variant retains at least one immunoepitope of Borrelia, preferably Borrelia sensu lato, more preferably *B. burgdorferi*, and most preferably pathogenic *B. burgdorferi*. Preferably the immunoepitope is specific to Borrelia, preferably Borrelia sensu lato, more preferably *B. burgdorferi*, and most preferably pathogenic *B. burgdorferi*.

Two amino acid sequences are functionally equivalent if they have substantially the same biological activities such as the ability to induce a cellular and/or humoral response in an animal vaccinated with the proteins. The proteins may be fused to other proteins, for example, signal sequence fusions may be employed in order to more expeditiously direct the secretion of the Oms28, Oms45, or Oms66 protein; further, a fusion protein may be produced which contains one or more of these proteins. The nucleotide sequences encoding these fusion proteins are also included in the present invention. A heterologous signal may replace the native Oms28, Oms45, or Oms66 signal, and when the resulting fusion is recognized, i.e. processed and cleaved by the host cell, the Oms28, Oms45, or Oms66 protein is secreted. Signals are selected based on the intended host cell, and may include bacterial, yeast, insect, and viral sequences.

Substitutional variants of the proteins disclosed herein are those in which at least one residue in the disclosed sequences has been removed and a different residue inserted in its place. Preferably, the amino acid change is conservative. Thus, modifications of Oms28, Oms45, and Oms66 primary amino acid sequences also include conservative variations. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

Further, as is the case for all proteins, the precise chemical structure depends on a number of factors. As ionizable amino and carboxyl groups are present in the molecule, a particular protein may be obtained as an acidic or basic salt, or in neutral form. All such preparations which retain their activity when placed in suitable environmental conditions are included in the definition. Additionally, the primary amino acid sequence may be augmented by derivatization using sugar moieties (glycosylation) or by other supplementary molecules such as lipids, phosphate, acetyl groups and the like, more commonly by conjugation with saccharides. The primary amino acid structure may also aggregate to form complexes, most frequently dimers. Certain aspects of such augmentation are accomplished through post-translational processing systems of the producing host; other such modifications may be introduced in vitro. In any event, such modifications are included in the definition so long as the activity of the protein is not destroyed. It is expected that such modifications may quantitatively or qualitatively affect the activity, either by enhancing or diminishing the activity of the protein in various assays.

Individual amino acid residues in the chain may also be modified by oxidation, reduction, or other derivatization, and the protein may be cleaved to obtain fragments which retain activity. Such alterations which do not destroy activity do not remove the protein sequence from the definition. The following discusses some of the modifications in further detail by way of example.

Thus, glycosylation variants are included within the scope of Oms28, Oms45, and Oms66. They include variants completely lacking in glycosylation (unglycosylated) and variants having at least one less glycosylated site than the native form (deglycosylated) as well as variants in which the glycosylation has been changed.

The invention also includes a method of producing the Oms28, Oms45, or Oms66 using recombinant DNA techniques. Recombinant Oms28, Oms45, and Oms66 fusion proteins may be produced in *Escherichia coli* (*E. coli*). These proteins can be used to immunize a mammal to generate antisera. The genes encoding the Oms28, Oms45, and Oms66 proteins may be cloned into a plasmid vector which is then used to transform *E. coli*.

The bacterial genes encoding the Oms28, Oms45, and Oms66 proteins can be derived from any strain Borrelia. Preferably the genes are from *B. burgdorferi*.

The invention provides polynucleotides encoding the Oms28, Oms45, and Oms66 proteins. These polynucleotides include DNA and RNA sequences which encode the protein. As discussed previously, it is understood that all polynucleotides encoding all or a portion of Oms28, Oms45, and Oms66 are also included herein, so long as they exhibit a function of Oms28, Oms45, and Oms66, such as the ability to induce or bind antibody. Such polynucleotides include both naturally occurring and intentionally manipulated, for example, mutagenized polynucleotides.

DNA sequences of the invention can be obtained by several methods. For example, the DNA can be isolated using hybridization procedures which are well known in the art. These include, but are not limited to: (1) hybridization of probes to genomic libraries to detect shared nucleotide sequences and (2) antibody screening of expression libraries to detect shared structural features, e.g. epitopes.

Hybridization procedures are useful for the screening of recombinant clones by using labeled mixed synthetic oligonucleotide probes where each probe is potentially the complete complement of a specific DNA sequence in the hybridization sample which includes a heterogeneous mixture of denatured double-stranded DNA. For such screening, hybridization is preferably performed on either single-stranded DNA or denatured double-stranded DNA. By using stringent hybridization conditions directed to avoid non-specific binding, it is possible, for example, to allow the autoradiographic visualization of a specific DNA clone by the hybridization of the target DNA to that single probe in the mixture which is its complete complement {Wallace, et al., *Nucleic Acid Research*, 9:879 (1981)}.

Alternatively, an expression library can be screened indirectly for Oms28, Oms45, and Oms66 peptides having at least one epitope using antibodies to Oms28, Oms45, and Oms66. Such antibodies can be either polyclonally or monoclonally derived and used to detect expression product indicative of the presence of Oms28, Oms45, and Oms66 DNA. Generally, a lambda gt11 library is constructed and screened immunologically according to the method of Huynh, et al. {in *DNA Cloning: A Practical Approach*, D. M. Glover, ed., 1:49 (1985)}. Alternatively, a lambda Exlox system can be used (Novagen, Inc., Madison, Wis.).

The development of specific DNA sequences encoding Oms28, Oms45, and Oms66 can also be obtained by e.g.: (1) isolation of a double-stranded DNA sequence from the genomic DNA, (2) chemical manufacture of a DNA sequence to provide the necessary codons for the polypeptide of interest, and (3) polymerase chain reaction (PCR).

DNA sequences encoding Oms28, Oms45, and Oms66 can be expressed in vitro by DNA transfer into a suitable host cell or by the use of cell-free in vitro translation systems known in the art. "Recombinant host cells" or "host cells" are cells in which a vector can be propagated and its DNA expressed. The term also includes any progeny of the subject host cell. It is understood that not all progeny are identical to the parental cell since there may be mutations that occur at replication. However, such progeny are included when the terms above are used.

The term "host cell" as used in the present invention is meant to include not only prokaryotes, but also, such eukaryotes as yeasts, filamentous fungi, as well as plant and animal cells. The term "prokaryote" is meant to include all bacteria which can be transformed with the gene for the expression of the Oms28, Oms45, or Oms66 protein. Prokaryotic hosts may include Gram negative as well as Gram positive bacteria, such as *E. coli*, *S. typhimurium*, *Listeria monocytogenes* and *Bacillus subtilis*.

A recombinant DNA molecule coding for the Oms28, Oms45, or Oms66 protein can be used to transform a host using any of the techniques commonly known to those of ordinary skill in the art. Especially preferred is the use of a plasmid containing the Oms28, Oms45, or Oms66 coding sequence for purposes of prokaryotic transformation. Where the host is prokaryotic, such as E. coli, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

In the present invention, the Oms28, Oms45, or Oms66 sequence may be inserted into a recombinant expression vector. The term "recombinant expression vector" refers to a plasmid, virus or other vehicle known in the art that has been manipulated by insertion or incorporation of oms28, oms45, or oms66 genetic sequence. Such expression vectors contain a promoter sequence which facilitates the efficient transcription of the inserted genetic sequence in the host. The expression vector typically contains an origin of replication, a promoter, as well as specific genes which allow phenotypic selection of the transformed cells. The transformed prokaryotic hosts can be cultured according to means known in the art to achieve optimal cell growth. Various shuttle vectors for the expression of foreign genes in yeast have been reported {Heinemann, et al., *Nature*, 340:205 (1989); Rose, et al., *Gene*, 60:237 (1987)}. Biologically functional DNA vectors capable of expression and replication in a host are known in the art. Such vectors are used to incorporate DNA sequences of the invention.

Methods for preparing fused, operably linked genes and expressing them in bacteria are known and are shown, for example, in U.S. Pat. No. 4,366,246 which is incorporated herein by reference. The genetic constructs and methods described therein can be utilized for expression of oms28, oms45, and oms66 in prokaryotic hosts.

Examples of promoters which can be used in the invention are: recA, trp, lac, tac, bacteriophage lambda $p_R$, or $p_L$ and bacteriophage T7. Examples of plasmids which can be used in the invention are listed in Sambrook, et al., {Molecular Cloning, Cold Spring Harbor Laboratories, 1982}.

Antibodies provided in the present invention are immunoreactive with Oms28, Oms45, or Oms66 protein. These antibodies can be polyclonal antibodies or monoclonal antibodies. Polyclonal antibodies can be produced according to methods known in the art, such as, vaccinating an animal with Oms28, Oms45, or Oms66 protein, collecting and purifying the animal's antisera directed against Oms28, Oms45, or Oms66. Monospecific polyclonal antibodies can also be produced using methods known in the art. Antibody which consists essentially of pooled monoclonal antibodies with different epitopic specificities, as well as distinct monoclonal antibody preparations are also provided. Monoclonal antibodies are made from antigen containing fragments of the protein by methods well known in the art {Kohler, et al., *Nature*, 256:495 (1975); *Current Protocols in Molecular Biology*, Ausubel, et al., ed., (1989)}. For example, monoclonal antibodies can be produced by the method of Kohler and Milstein {*Nature*, 256:495–497 (1975)} by immortalizing spleen cells from an animal inoculated with the immunogen or a fragment thereof, usually by fusion with an immortal cell line (preferably a myeloma cell line), of the same or a different species as the inoculated animal, followed by the appropriate cloning and screening steps. The antibodies may also be recombinant monoclonal antibodies produced according to the methods disclosed in Reading, U.S. Pat. No. 4,474,893, or Cabilly, et al., U.S. Pat. No. 4,816,567. The antibodies may also be chemically constructed according to the method disclosed in Segel, et al., U.S. Pat. No. 4,676,980.

The term antibody, or immunoglobulin, as used in this invention includes intact molecules as well as fragments thereof, such as Fab, $F(ab')_2$, Fv, and single chain antibody (SCA) which are capable of binding an epitopic determinant on Oms28, Oms45, or Oms66. SCA is a genetically engineered fused single chain molecule containing the variable region of the light chain and the variable region of the heavy chain linked by a suitable polypeptide linker. Methods for making these fragments are known in the art, see e.g., Harlow and Lane, *Antibodies: A Laboratory Manual*, Cold Spring Harbor Laboratory, New York (1988).

As discussed previously, minor modifications of Oms28, Oms45, and Oms66 primary amino acid sequences may result in proteins which have substantially equivalent function compared to the Oms28, Oms45, and Oms66 proteins described herein. Such modifications may be deliberate, as by site-directed mutagenesis, or may be spontaneous. All proteins produced by these modifications are included herein as long as Oms28, Oms45, and Oms66 functions exist.

Isolation and purification of microbially expressed proteins, or fragments thereof, provided by the invention, may be carried out by the methods described herein together with conventional means including preparative chromatography and immunological separations involving monoclonal or polyclonal antibodies.

The invention extends to any host modified proteins according to the methods described, or modified by any other methods, commonly known to those of ordinary skill in the art, such as, for example, by transfer of genetic material using a lysogenic phage, and which result in a prokaryote expressing the gene for Oms28, Oms45, or Oms66 protein. Prokaryotes transformed with the gene encoding the Oms28, Oms45, or Oms66 protein are particularly useful for the production of proteins which can be used for the immunization of an animal.

In one embodiment, the invention provides a pharmaceutical composition useful for inducing an immune response to Borrelia in an animal comprising an immunologically effective amount of Oms28, Oms45, and/or Oms66 in a pharmaceutically acceptable carrier. The term "immunogenically effective amount," as used in describing the invention, is meant to denote that amount of Borrelia antigen which is necessary to induce in an animal the production of an immune response to the respective Borrelia. Oms28, Oms45, and Oms66 are particularly useful in sensitizing the immune system of an animal such that, as one result, an immune response is produced which ameliorates the effect of infection by these Borrelia. Oms28, Oms45, and Oms66 proteins i.e., their variants, functional equivalents, and derivatives, which are effective as vaccines against the disease caused by Borrelia antigen, can be screened for using the methods known in the art such as described in Fikrig, E., et al., *Science*, 250:553–556 (1990). The vaccination methods disclosed in this reference and methods known in the art can also be used for vaccinating animals with Oms28, Oms45, and Oms66 proteins.

Oms28, Oms45, and Oms66 proteins can be administered, alone or in combination, e.g. parenterally by injection, rapid infusion, nasopharyngeal absorption, dermal absorption, and enterally, e.g., orally. Pharmaceutically acceptable carrier preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers for occlusive dressings can be used to increase skin permeability and enhance antigen absorption. Liquid dosage forms for oral administration may generally comprise a liposome solution containing the liquid dosage form. Suitable forms for suspending the liposomes include emulsions, suspensions, solutions, syrups, and elixirs containing inert diluents commonly used in the art, such as purified water.

Besides the inert diluents, such compositions can also include adjuvants, wetting agents, emulsifying and suspending agents, and sweetening, flavoring, and perfuming agents.

For example, recombinant bacteria and viruses expressing Oms28, Oms45, and/or Oms66 can be used as vaccines in the above compositions, and be administered, e.g. orally. The vaccines can also be added to baits against potential carriers of Borrelia such as rodents so that they will not be infected by Borrelia and be carriers in spreading Borrelia and the disease to humans and other animals, such as domestic animals.

It is also possible for the antigenic preparations containing the Oms28, Oms45, and/or Oms66 proteins of the invention to include an adjuvant. Adjuvants are substances that can be used to nonspecifically augment a specific immune response. Normally, the adjuvant and the antigen are mixed prior to presentation to the immune system, or presented separately, but into the same site of the animal being immunized. Adjuvants can be loosely divided into several groups based on their composition. These groups include oil adjuvants (for example, Freund's Complete and Incomplete Adjuvants), mineral salts (for example, $AlK(SO_4)_2$, $AlNa(SO_4)_2$, $AlNH_4(SO_4)$, silica, alum, $Al(OH)_3$, $Ca_3(PO_4)_2$, kaolin, and carbon), polynucleotides (for example, poly IC and poly AU acids), and certain natural substances (for example, wax D from *Mycobacterium, tuberculosis*, as well as substances found in *Corynebacterium parvum, Bordetella pertussis*, and members of the genus Brucella).

In another embodiment, a method of inducing an immune response to Borrelia in animals is provided. Many different techniques exist for the timing of the immunizations when a multiple immunization regimen is utilized. It is possible to use the antigenic preparation of the invention more than once to increase the levels and diversity of expression of the immune response of the immunized animal. Typically, if multiple immunizations are given, they will be spaced two to four weeks apart. Suitable subjects include any animal susceptible to infection by the respective Borrelia. The animals are preferably mammals. Examples of the mammals are: humans, domestic and wild mammals. The domestic mammals include: livestock such as cattle, swine, goats, horses, buffaloes; and pets such as cats and dogs.

Generally, the dosage of Oms28, Oms45, and/or Oms66 proteins administered to an animal will vary depending on such factors as age, condition, sex and extent of disease, if any, and other variables which can be adjusted by one of ordinary skill in the art.

The antigenic preparations of the invention can be administered as either single or multiple dosages and can vary, e.g. from about 10 μg to about 1,000 μg for the Oms28, Oms45, and/or Oms66 antigen per dose, more preferably from about 50 μg to about 700 μg Oms28, Oms45, and/or Oms66 antigen per dose, most preferably from about 50 μg to about 300 μg Oms28, Oms45, and/or Oms66 antigen per dose.

When used for immunotherapy, the antibodies, preferably monoclonal antibodies or SCA, of the invention may be unlabeled or labeled with a therapeutic agent. These agents can be coupled either directly or indirectly to the antibodies of the invention. One example of indirect coupling is by use of a spacer moiety. These spacer moieties, in turn, can be either insoluble or soluble {Diener, et al., *Science*, 231:148 (1986)} and can be selected to enable drug release from the antibody molecule at the target site. Examples of therapeutic agents which can be coupled to the antibodies for immunotherapy are drugs, radioisotopes, lectins, and toxins.

The labeled or unlabeled antibodies can also be used in combination with therapeutic agents such as those described above. Especially preferred are therapeutic combinations comprising the antibody and immunomodulators and other biological response modifiers.

When the antibody is used in combination with various therapeutic agents, such as those described herein, the administration of the antibody and the therapeutic agent usually occurs substantially contemporaneously. The term "substantially contemporaneously" means that the antibody and the therapeutic agent are administered reasonably close together with respect to time. Usually, it is preferred to administer the therapeutic agent before the antibody. For example, the therapeutic agent can be administered 1 to 6 days before the antibody. The administration of the therapeutic agent can be daily, or at any other interval, depending upon such factors, for example, as the nature of the disorder, the condition of the patient and half-life of the agent.

The dosage ranges for the administration of antibodies are those large enough to produce the desired effect in which the onset symptoms of the disease caused by Borrelia are ameliorated. The dosage should not be so large as to cause adverse side effects, such as unwanted cross-reactions, anaphylactic reactions, and the like. Generally, the dosage will vary with the age, condition, sex and extent of the disease in the subject and can be determined by one of skill in the art. The dosage can be adjusted by the individual physician in the event of any complication. Dosage can vary, e.g., from about 0.1 mg/kg to about 2000 mg/kg, preferably about 0.1 mg/kg to about 500 mg/kg, in one or more dose administrations daily, for one or several days. Generally, when the antibodies are administered conjugated with therapeutic agents, lower dosages, comparable to those used for in vivo diagnostic imaging, can be used.

The antibodies can be administered parenterally by injection or by gradual perfusion over time. The antibodies can be administered intravenously, intraperitoneally, intramuscularly, subcutaneously, intracavity, or transdermally, alone or in combination with effector cells.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents and inert gases, preferably isolated or substantially pure, and the like.

An animal may also be vaccinated, or treated using the disclosed, preferably isolated or in substantially pure composition, with nucleotide sequences, their mutagenized sequences or fragments thereof, which may be directly administered or incorporated into a plasmid and administered into the animal. The nucleic acid sequences may be mixed with a pharmaceutically acceptable carrier prior to administration. The administrations may be by means of microinjection or particle bombardment using methods known in the art. For example, the injection may be by means of a gene gun, such as described in Yang, N.-S. et al., *Gene Therapy via Particle Bombardment: Applications of the Accell Gene Gun*, in *Gene Therapeutics: Methods and Applications of Direct Gene Transfer*, Wolff, J. A., ed., Birkhauser, USA (1994).

In a further embodiment, the invention provides a method of detecting a pathogenic Borrelia-associated disorder in a subject comprising contacting a cell component with a reagent which binds to the cell component. The cell component can be nucleic acid, such as DNA or RNA, or it can be protein. When the component is nucleic acid, the reagent is a nucleic acid probe or PCR primer. When the cell component is protein, the reagent is an antibody probe. The probes are detectably labeled, for example, with a radioisotope, a fluorescent compound, a bioluminescent compound, a chemiluminescent compound, a metal chelator or an enzyme. Those of ordinary skill in the art will know of other suitable labels for binding to the antibody, or will be able to ascertain such, using routine experimentation.

For purposes of the invention, an antibody or nucleic acid probe specific for Oms28, Oms45, and/or Oms66 proteins may be used to detect the presence of the respective Oms28, Oms45, and/or Oms66 proteins (using antibody) or polynucleotide (using nucleic acid probe) in biological samples. Any specimen containing a detectable amount of Oms28, Oms45, and/or Oms66 antigen or polynucleotide can be used. Preferred specimens of this invention are a biological fluid or tissue sample. Preferred examples of a biological fluid sample include: blood, serum, plasma, synovial, and cerebro-spinal fluid. Preferred examples of a biological tissue sample include tissue samples from the liver and kidney and tissue of endothelial origin.

When the cell component is nucleic acid, it may be necessary to amplify the nucleic acid prior to binding with a Borrelia specific probe. Preferably, polymerase chain reaction (PCR) is used, however, other nucleic acid amplification procedures such as ligase chain reaction (LCR), ligated activated transcription (LAT) and nucleic acid sequence-based amplification (NASBA) may be used.

Another technique which may also result in greater sensitivity consists of coupling antibodies to low molecular weight haptens. These haptens can then be specifically detected by means of a second reaction. For example, it is common to use such haptens as biotin, which reacts with avidin, or dinitrophenyl, pyridoxal, and fluorescein, which can react with specific antihapten antibodies.

Alternatively, Oms28, Oms45, or Oms66 protein can be used to detect antibodies to the respective Oms28, Oms45, or Oms66 protein in a specimen. The Oms28, Oms45, and Oms66 of the invention is particularly suited for use in immunoassays in which they can be utilized in liquid phase or bound to a solid phase carrier. In addition, Oms28, Oms45, and Oms66 used in these assays can be detectably labeled in various ways.

Examples of immunoassays which can utilize the Oms28, Oms45, and Oms66 proteins described in the invention include competitive and noncompetitive immunoassays in either a direct or indirect format. Examples of such immunoassays are the radioimmunoassay (RIA), the sandwich (immunometric assay) and the Western blot assay. Detection of antibodies which bind to the Oms28, Oms45, or Oms66 protein of the invention can be done utilizing immunoassays which run in either the forward, reverse, or simultaneous modes, including immunohistochemical assays on biological samples. The concentration of Oms28, Oms45, and Oms66 which is used will vary depending on the type of immunoassay and nature of the detectable label which is used. However, regardless of the type of immunoassay which is used, the concentration of Oms28, Oms45, and Oms66 utilized can be readily determined by one of ordinary skill in the art using routine experimentation.

The Oms28, Oms45, and Oms66 of the invention can be bound to many different carriers and used to detect the presence of antibody specifically reactive with the polypeptide. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for purposes of the invention. Those skilled in the art will know of other suitable carriers for binding Oms28, Oms45, and Oms66 or will be able to ascertain such, using routine experimentation.

There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds.

For purposes of the invention, the antibody which binds to Oms28, Oms45, or Oms66 of the invention may be present in various biological samples. Any sample containing a detectable amount of antibodies to Oms28, Oms45, or Oms66 can be used. Preferred specimens of this invention are: a biological fluid or tissue sample. Preferred examples of a biological fluid sample include: blood, serum, plasma, synovial, and cerebro-spinal fluid. Preferred examples of a biological tissue sample include tissue samples from the liver and kidney and tissue of endothelial origin.

The antibodies of the invention, preferably monoclonal antibodies and SCA, directed toward Oms28, Oms45, or Oms66, are also useful for the in vivo detection of antigen. The detectably labeled antibody is given in a dose which is diagnostically effective. The term "diagnostically effective" means that the amount of detectably labeled monoclonal antibody is administered in sufficient quantity to enable detection of Oms28, Oms45, or Oms66 antigen for which the antibodies are specific.

The concentration of detectably labeled antibody which is administered should be sufficient such that the binding to those cells, body fluid, or tissue having Oms28, Oms45, and/or Oms66 is detectable compared to the background. Further, it is desirable that the detectably labeled antibody be rapidly cleared from the circulatory system in order to give the best target-to-background signal ratio.

As a rule, the dosage of detectably labeled antibody for in vivo diagnosis will vary depending on such factors as age, sex, and extent of disease of the subject. The dosage of antibody can vary, e.g., from about 0.001 mg/m$^2$ to about 500 mg/m$^2$, preferably 0.1 mg/m$^2$ to about 200 mg/m$^2$, most preferably about 0.1 mg/m$^2$ to about 10 mg/m$^2$. Such dosages may vary, for example, depending on whether multiple injections are given, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 key range, which may be readily detected by conventional gamma cameras.

For in vivo diagnosis, radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr, and $^{201}$Tl.

The antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

The antibodies, preferably monoclonal antibodies and SCA, of the invention can also be used to monitor the course of amelioration of Borrelia associated disorder. Thus, by measuring the increase or decrease of Oms28, Oms45, and/or Oms66 proteins or antibodies to Oms28, Oms45, and/or Oms66 proteins present in various body fluids or tissues, it would be possible to determine whether a particular therapeutic regiment aimed at ameliorating the disorder is effective.

The materials for use in the method of the invention are ideally suited for the preparation of a kit. Such a kit may comprise a carrier means being compartmentalized to receive in close confinement one or more container means such as vials, tubes, and the like, each of the container means comprising one of the separate elements to be used in the method. For example, one of the container means may comprise a Oms28, Oms45, and/or Oms66 binding reagents, such as an antibody. A second container may further comprise Oms28, Oms45, and/or Oms66 proteins. The constituents may be present in liquid or lyophilized form, as desired.

In the above discussion, the diagnostic tests, e.g. nucleic acid hybridization assays or immunoassays, may test for either or both Oms28, Oms45, and Oms66. Alternatively, they may consist of panel tests which test for both Oms28, Oms45, and Oms66 proteins or nucleic acid sequences, in combination with other proteins or nucleic acid sequences specific for Borrelia. Similarly, the compositions, e.g. for immunoassays or vaccinations, may consist of Oms28, Oms45, or Oms66, singly. Alternatively, they may consist of a cocktail containing both Oms28, Oms45, and Oms66, or these proteins in combination with other proteins specific for Borrelia. The antibody compositions may consist of antibodies specific to Oms28, Oms45, or Oms66. Alternatively, they may consist of a cocktail containing antibodies to Oms28, Oms45, and Oms66, or to these proteins and other proteins specific for Borrelia. The hybridization assays are preferably run at moderate to stringent conditions. The immunoassays are preferably conducted under conditions of reduced non-specific binding. Thus, the test kits and methods using these compositions are varied accordingly.

The following examples are intended to illustrate but not limit the invention. While they are typical of those that might be used, other procedures known to those skilled in the art may alternatively be used.

EXAMPLES

Example 1

Isolation of the OM of B. buradorferi and the Identification of its Porin Activities and Candidate Outer Membrane-Spanning Proteins The abbreviations used in this Example are defined as follows:

aIRS—adsorbed immune rabbit serum;
ATCC—American Type Culture Collection
DTT—dithiothreitol
ECL—enhanced chemiluminescence
EF—endoflagella
EM—erythema migrans
IM—inner membrane
IRS—immune rabbit serum
MAb—monoclonal antibody
OM—outer membrane
OMV—outer membrane vesicles
NEPHG—non-equilibrium pH gel
NEPHGE—non-equilibrium pH gel electrophoresis
nm—nanometer
nS—nano-Siemen
TX-100—Triton X-100
TX-100—Triton X-100
TX-114—Triton X-114.

This Example shows the isolation and purification of the OM of B. burgdorferi and its protein constituents. It focuses on functional Oms proteins, more specifically porin proteins that allow for the passive diffusion of nutritional solutes. Porin proteins are indisputable markers of the OM in gram negative bacteria and their identification in B. burgdorferi would establish the paradigm for the membrane-spanning organization of other Oms proteins. This Example also demonstrates that two porin activities were associated with the OMV derived from B. burgdorferi, one having a single channel conductance of approximately 0.6 nS and the other having a conductance of approximately 12.6 nS. These two porin proteins represent the first two functional OM-spanning proteins characterized biochemically in B. burgdorferi. In addition, the findings in this Example implicate certain surface exposed OM candidate proteins in infectivity and in induction of protective immunity.

In more detail, we have isolated and purified OMV from Borrelia burgdorferi strain B31 based on methods developed for isolation of T. pallidum OMV. Purified OMV exhibited distinct porin activities with conductances of 0.6 and 12.6 nS and had no detectable β-NADH oxidase activity indicating their outer membrane origin and their lack of inner membrane contamination, respectively. Hydrophobic proteins were identified by phase partitioning with Triton X-114. Most of these hydrophobic membrane proteins were not acylated, suggesting that they are outer membrane-spanning proteins (Oms). Identification of palmitate labeled lipoproteins revealed that several were enriched in the OMV, several were enriched in the protoplasmic cylinder inner membrane fraction, and others were found exclusively associated with the inner membrane. The protein composition of OMV changed significantly with successive in vitro cultivation of strain B31. Using antiserum with specificity for virulent strain B31, we identified OMV antigens on the surface of the spirochete, and identified proteins whose presence in OMV could be correlated with virulence and protective immunity in the rabbit Lyme disease model. These virulent strain-associated Oms proteins may provide new insight into the pathogenesis of Lyme disease.

METHODS

Bacterial Strains and Media

*Borrelia burgdorferi* sensu stricto strain B31 was used in the experiments presented in this report and will be referred to as *B. burgdorferi* strain B31 throughout this Example. Virulent *B. burgdorferi* was originally isolated from infected mouse or rabbit tissue as previously described {Foley, D. M. et al., *J. Clin. Invest.*, 96:965–975 (1995)}. The term "passage" and the corresponding number refers to the number of times a B31 *B. burgdorferi* log phase culture was transferred to fresh BSK II media. Previous studies indicated that *B. burgdorferi* strain B31 maintained infectivity in rabbits and mice to at least passage 47 and 85, respectively {Id.}. The avirulent *B. burgdorferi* strain B31 (ATCC 35210) has been passaged several hundred times in vitro in our laboratory and is non-infectious for both mice and rabbits {Id. and Norris, S. J. et al., *Infect. Immun.*, 60:4662–4672 (1992)}. Each of the *B. burgdorferi* passages was grown in BSK II media supplemented with 6% normal rabbit serum (NRS) as previously described {Barbour, A. G., Yale *J. Biol. Med*, 57:521–525 (1984)}.

Antiserum Specific for Virulent *B. burgdorferi* Strain B31

Rabbits were infected intradermally with $4\times10^7$ virulent B31 *B. burgdorferi* passage 4 and challenged with equivalent amounts of virulent homologous *B. burgdorferi* 22 weeks later {Foley, D. M. et al., *J. Clin. Invest.*, 96:965–975 (1995)}. These rabbits were immune to challenge as assessed by both the lack of EM development and the absence of disseminated infection {Id.}. The rabbits were bled 4 weeks post-challenge (referred to as immune rabbit serum or IRS) and the immune serum cleared of antibodies common to both the avirulent and virulent *B. burgdorferi* by adsorption with avirulent ATCC B31 spirochetes as follows. A frozen pellet containing $6.25\times10^9$ whole cells of avirulent B31 *B. burgdorferi* was incubated with 750 μl of the 4 week post-challenge infection-derived serum. The samples were incubated overnight at 4° C. with continuous vortexing to maintain a homogenous mixture of cells within the serum. After each incubation, the cells were pelleted by centrifugation at 15,000×g for ten minutes and the serum supernatant transferred to a new tube containing another $6.25\times10^9$ frozen whole cells of avirulent B31 *B. burgdorferi*. This procedure was repeated eight times. After the eighth adsorbtion, the serum was incubated overnight at 4° C. with an acetone powder {Harlow, E., et al., *Antibodies: A Laboratory Manual*, Cold Spring Harbor Laboratory Press, Cold Spring Harbor, N.Y., p. 726 (1988)} corresponding to $1.5\times 10^{10}$ equivalents of PBS-washed avirulent B31 *B. burgdorferi*; this procedure was repeated four times. The serum was considered adsorbed when reactivity to proteins derived from $3\times10^7$ avirulent B31 cells was no longer observed in ECL immunoblots yet maintained reactivity with proteins from the identical amount of virulent B31 passage 1 cells {Foley, D. M. et al., *J. Clin. Invest.*, 96:965–975 (1995)}. This serum, enriched for antibodies specific to low-passage, virulent strain-associated antigens, is designated adsorbed immune rabbit serum (aIRS).

Monoclonal antibodies H3TS, H6831, and H9724 {Barbour, et al., *J. Infect. Dis.*, 152:478–484 (1985); Barbour, et al., *Infect. Immun.*, 45:94–100 (1984), specific for the OspA, OspB, and EF, respectively were kindly provided by Dr. Alan Barbour, University of Texas Health Science Center, San Antonio, Tex. Polyclonal antiserum against OspD {Norris, S. J. et al., *Infect. Immun.*, 60:4662–4672 (1992)} was a generous gift from Dr. Steven Norris, University of Texas at Houston.

Isolation of the *B. burgdorferi* Outer Membrane

The outer membrane of *B. burgdorferi* was isolated as described for *T. pallidum* and *Treponema vincentii* {Blanco, D. R., et al., *J. Bacteriol.*, 176:6088–6099 (1994)} with the following modifications. Half-liter cultures of *B. burgdorferi* were grown in BSK II to late log phase and harvested by centrifugation at 5,800×g for 20 min. The resulting pellet corresponding to $5\times10^{10}$ to $1\times10^{11}$ *B. burgdorferi* was washed once in phosphate buffered saline pH 7.4 (PBS) supplemented with 0.1% bovine serum albumin (BSA) and centrifuged again as described above. The supernatant was discarded and the pellet was resuspended in 90 ml of ice-cold 25 mM citrate buffer pH 3.2 containing 0.1% BSA. The suspension was incubated on a rocker at room temperature for a total of 2 hours and, additionally, was vortexed for 1 minute every 30 minutes. The resulting outer membrane vesicles (OMV) and protoplasmic cylinders (PC) were pelleted at 20,000×g for 30 minutes and resuspended in 12 ml of 25 mM citrate buffer pH 3.2, 0.1% BSA. Six-ml aliquots were layered onto a discontinuous sucrose gradient (in citrate buffer pH 3.2 at 5° C.) composed of 5 ml 56% (wt/wt) sucrose, 15.5 ml 42% (wt/wt) sucrose, and 12.5 ml 25% (wt/wt) sucrose, and were centrifuged at 100,000×g for 16 hr at 5° C. using a Beckman SW28 rotor (Beckman Instruments, Inc., Fullerton, Calif.). After centrifugation, two separate bands corresponding to the OMV fraction (upper band) and the PC fraction (lower band) were removed by needle aspiration, diluted five- to seven-fold in cold PBS pH 7.4, and pelleted by centrifugation at 141,000×g for 4 hr at 5° C. The pelleted OMV material was resuspended in 1 ml of 25 mM citrate buffer pH 3.2, applied to a continuous 10%–42% (wt/wt) sucrose gradient (12 ml in volume), and centrifuged using a SW41 rotor at 100,000×g for 16 hours at 5° C. The membrane band was removed by needle aspiration, diluted 7-fold in PBS pH 7.4, and the total OMV pelleted at 141,000×g for 4 hours at 5° C. The final OMV pellet was resuspended in 50–100 μl PBS pH 7.4 containing 1 mM phenylmethylsulfonyl fluoride (PMSF) and was stored in aliquots at −80° C. The PC material was pelleted at 10,000×g for 20 minutes at 5° C., resuspended in 1 ml PBS pH 7.4, and stored at either −20° C. or −80° C.

β-NADH Oxidase Assays

OMV were prepared from *B. burgdorferi* B31 avirulent ATCC as described above except that 0.5 mM dithiothreitol (DTT) was added to all buffers and sucrose solutions used in the OMV isolation. β-NADH oxidase assays were conducted as described by Osborn, et al. {Osborn, et al., *J. Biol. Chem.*, 247:3962–3972 (1972) with slight modifications {Thom, J. R., et al., *J. Bacteriol.*, 170:5654–5661 (1988); Norris, S. J., et al., *Microbiol. Rev.*, 57:750–779 (1993); Stanton, T. B., et al., *J. Bacteriol.*, 175:2980–2987 (1993); Radolf, J. D., et al., *Infect. Immun.*, 63:2154–2163 (1995); Norris, S. J., personal communication}. Twenty equivalent 1.8-ml fractions were collected from a sucrose gradient, their density determined using a refractometer, and 90 μl used for the β-NADH oxidase assay. Values reported reflect the average of three independent assays.

Protein Assays

The concentration of protein was determined using the BCA protein assay system of Pierce Chemical Co. (Rockford, Ill.).

Triton X-114 Phase Partitioning of Outer Membrane Vesicle Proteins

Triton X-114 (TX-114) extractions were conducted essentially as previously described {Cunningham, T. M., et al., *J. Bacteriol.*, 170:5789–5796 (1988)} with the following modifications. OMV material derived from $1 \times 10^9$ to $5 \times 10^9$ *B. burgdorferi* was solubilized in 1 ml PBS pH 7.4 containing 1% TX-114 by gentle rocking at 4° C. overnight. The TX-114 insoluble material was removed by two successive centrifugations at 15,000×g at 4° C. for 15 minutes. The supernatant was transferred to a sterile microcentrifuge tube and incubated at 37° C. for 15 minutes followed by separation of the two phases via centrifugation at 15,000×g for 15 minutes at room temperature. The top aqueous phase was transferred to a new tube and re-extracted three times with 1% TX-114 as described above. The bottom detergent phase was washed with 1 ml PBS pH 7.4 and re-extracted three times. Protein within the final detergent phase, a total of approximately 15 μg to 25 μg, was precipitated by adding a 10-fold volume of ice-cold acetone. Precipitated protein was pelleted by centrifugation (15,000×g for 30 minutes, 4° C.) and resuspended in non-equilibrium pH two-dimensional (2D) gel buffer (see below).

Electron Microscopy

Samples analyzed by electron microscopy were loaded in 40-μl volumes onto Parlodion (Mallinckrodt, Inc., St. Louis, Mo.) and carbon-coated 300-mesh copper grids (Ted Pella Inc., Tustin, Calif.), incubated at room temperature for 5 minutes, and washed three times in 50-μl drops of PBS pH 7.4 followed by two washes in 50 μl drops of double distilled water. The grids were then stained for 20 seconds in 1% uranyl acetate, washed three times in 50 μl of double-distilled water, and air dried. The grids were examined with an electron microscope (100 cx; JEOL U.S.A., Inc., Peabody, Mass.) using an accelerating voltage of 80 kV.

Immunoelectron microscopy (IEM) was conducted as follows. $3 \times 10^7$ *B. burgdorferi* strain B31 passages 1, 50, and the avirulent ATCC were pelleted at 2,000×g for 8 minutes and suspended in 10 μl of BSK II media. A 1:5 dilution, 10 μl in volume, of either heat inactivated basal serum, unadsorbed immune rabbit serum (IRS), or adsorbed IRS (aIRS) in 50% normal goat serum (NGS), 0.5×PBS were added separately to the 10 μl *B. burgdorferi* suspension for a final serum dilution of 1:10. The samples were incubated at 34° C. for 5.5 hours, after which the spirochetes were shown to retain motility as assessed by dark-field microscopy. The 20 μl suspension was then diluted to 1 ml with 0.15 M NaCl, 10 mM $CaCl_2$, 10 mM $MgCl_2$ (SCM) and the cells pelleted at 2,000×g for 8 minutes. The cells were resuspended in 30 μl of SCM and a 20-μl droplet incubated on the top surface of a Parlodion 300 mesh copper grid for 10 minutes at room temperature. The grids were washed four times in SCM and then blocked in a humidified chamber for 20 minutes at room temperature in 50% NGS, 0.5×SCM. After 8 further washes in SCM, the grids were incubated in a humidified chamber for 1 hour at 4° C. in a 1:20 dilution of goat anti-rabbit immunoglobulin conjugated to 10 nm colloidal gold (Sigma Chemical Co., St. Louis, Mo.) in 10% NGS, 0.9×SCM. The grids were washed 8 times in SCM and 4 times with double-distilled water ($ddH_2O$), stained for 45 seconds in 1% uranyl acetate, rinsed 3 times with $ddH_2O$, and examined in a JEOL electron microscope at 80 kV accelerating voltage.

Nonequilibrium pH Gel Electrophoresis (NEPHGE)

Nonequilibrium pH gel electrophoresis (NEPHGE) was performed as described by O'Farrell {O'Farrell, et al., *Cell*, 12:1133–1142 (1977)} with modifications reported by Norris et al. {Norris, S. J. et al., *Infect. Immun.*, 60:4662–4672 (1992)}. Briefly, samples corresponding to OMV derived from $1 \times 10^9$ to $5 \times 10^9$ *B. burgdorferi* were extracted with TX-114 as previously described and, after acetone precipitation, suspended in 50 μl sample buffer containing 9.2 M urea, 1.6% pH 5 to 7 and 0.4% pH 3 to 10 ampholines (Bio-Rad Laboratories, Richmond, Calif.), 4% Nonidet P-40 (NP-40; Sigma Chemical Co., St. Louis, Mo.), and 5% β-mercaptoethanol (Sigma Chemical Co.). The sample was loaded onto a nonequilibrium pH gel (NEPHG), 0.2 cm by 12 cm, composed of 4% acrylamide and 0.24% bisacrylamide (GIBCO/BRL, Bethesda, Md.), 9.2 M urea, 1.6% pH 5 to 7 and 0.4% pH 3 to 10 ampholines, and 2% NP-40. The upper and lower tank electrolyte solutions contained 10 mM $H_3PO_4$ and 20 mM NaOH respectively. The NEPHG was pre-run at 400 V constant voltage for 5 min., the sample loaded onto the NEPHG, and the proteins separated at 400 V (constant voltage) for 4 hours. The gel was extruded out of the glass tube and analyzed by SDS-PAGE or stored sealed at −80° C. for subsequent SDS-PAGE.

SDS-PAGE and Western blotting

Two-dimensional separation of protein was performed by SDS-PAGE as described {Blanco, D. R. et al., *J. Bacteriol.*, 176:6088–6099 (1994); O'Farrell, et al., *Cell*, 12:1133–1142 (1977); Laemmli, U. K., *Nature* (London), 227:680–685 (1970)}. Prior to second dimension SDS-PAGE, NEPHG were incubated at room temperature for 30 minutes in 2× final sample buffer (FSB) containing 4% SDS, 10% β-mercaptoethanol, 20% glycerol, and 0.01% bromophenol blue buffered in 62.5 mM Tris HCl pH 6.8. The gel was then placed along the top of the second dimension SDS-polyacrylamide gel and sealed in place using 0.8% low-melting point agarose (GIBCO/BRL, Bethesda, Md.) in SDS-PAGE running buffer (192 mM glycine, 25 mM Tris base, 0.1% SDS, pH 8.3).

Following electrophoresis, protein was transferred to a polyvinylidene difluoride (PVDF; Millipore, Bedford, Mass.) membrane as previously described {Blanco, D. R., et al., *J. Bacteriol.*, 176:6088–6099 (1994); Towbin, H., et al., *Proc. Natl. Acad. Sci. USA*, 76:4350–4354 (1979)} and either stained with 1% Amido Black for subsequent immunoblot analysis, or stained with colloidal gold (AuroDye forte, Amersham Corp., Arlington Heights, Ill.). PVDF membranes used for immunoblotting were blocked for 1 hour with 5% non-fat powdered milk and 0.2% Tween-20 in PBS pH 7.4 (MT-PBS), incubated with either aIRS diluted 1:500, anti-OspD diluted 1:5000, anti-EF diluted 1:50, and anti-OspA or OspB MAb diluted 1:500 in MT-PBS for 1 hour. After incubation, the immunoblots were washed thoroughly with 0.2% Tween-20 in PBS pH 7.4 (T-PBS), and incubated for one hour with either anti-mouse or anti-rabbit immunoglobulin conjugated to horseradish peroxidase diluted 1:2000 or 1:5000 in MT-PBS. After thorough washing of the membrane with T-PBS, antigen-antibody complexes were visualized using the Enhanced Chemiluminescence (ECL) system (Amersham Corp.) and exposure to Kodak X-AR5 film (Eastman Kodak Co., Rochester, N.Y.).

Intrinsic Labeling of *B. burgdorferi* with [$^3$H]Palmitate

*B. burgdorferi* cells were radiolabeled with [$^3$H]palmitate as previously described {Norris, S. J. et al., *Infect. Immun.*, 60:4662–4672 (1992); Brandt, M. E., et al., *Infect. Immun.*, 58:983–991 (1990)} with the following modifications. 5 mCi of [$^3$H]palmitate (Amersham Corp.) was added to 0.5 liters of BSK II media containing $2.5 \times 10^{10}$ *B. burgdorferi* and the culture incubated at 34° C. until the total number of cells was $1 \times 10^{11}$ (approximately 48 hours). The cells were then processed as described above to obtain the OMV material. The OMV proteins were extracted with Triton X-114 and then subjected to NEPHGE and SDS-PAGE. The proteins were fixed in the gel with 40% isopropanol and 10% acetic acid, incubated in fluor (Amplify; Amersham Corp.) for 1 hour, dried at 80° C., and exposed to X-AR 5 film at −80° C. for 1 month.

Planar Lipid Membrane Assays

Solvent-free membranes were formed at room temperature by the union of two monolayers of diphytanoyl phosphatidylcholine (Avanti Polar Lipids, Alabaster, Ala.) as described previously {Kagan, B. L., et al., *Meth. Enz.*, 235:699–713 (1994)}. The monolayers were opposed over a hole 100–200 µm in diameter in a Teflon partition dividing two aqueous phases; the aperture was initially precoated with a 2% solution of hexadecane in n-pentane. Membrane formation and stability were monitored by measuring membrane capacitance. Voltages were applied across the membrane by using a signal generator or a battery driven stimulator. Currents were measured by means of a voltage clamp amplifier (Axopatch 1C, Axon Instruments, Sunnyvale, Calif.) with a headstage (CV-3B) suitable for the planar membrane and recorded on a chart recorder. A digital pulse code modulator (PCM-501 ES, Sony Corporation, Tokyo, Japan) and video cassette recorder (Sharp Instruments, Tokyo, Japan) were used for data acquisition and storage. Agar-agar silver chloride/silver electrodes were used to impose voltages and record currents across the membrane. Membrane conductance (g) was calculated from Ohm's law (g=I/V) in which I is current and V is voltage. Voltage clamp conditions were employed in all experiments with the front chamber functioning as the virtual ground. The porin suspension was added to the front compartment salt solution and the sign of the membrane potential corresponded to the rear compartment of the chamber.

Painted black lipid membranes 500 µm in diameter were formed with a 13 mg/ml solution of diphytanoyl phosphatidylcholine in n-heptane. The construction of the cell used in these porin assays allowed for the displacement of solutions present in the front compartment by adding new aqueous suspensions {Mirzabekov, T. A., et al., *J. Membr. Biol.*, 133:129–143 (1993)}. Membrane formation was monitored by viewing the bilayer as black with incident light and by measuring the capacitance across the membrane. Once the membrane had formed, the solution present in the cis-side of the cell was substituted with a porin-containing suspension (approximately 1–10 ng/ml) of identical ionic strength.

For both the solvent-free or solvent containing bilayer assays, *B. burgdorferi* B31 OMV (approximately 1 µg/µl) were solubilized in 0.1% Triton X-100, phosphate buffered saline (PBS) pH 7.4 at 4° C. for 30 minutes. Samples were diluted 1:1000 to 1:100,000 in 1 M KCl, 5 mM HEPES pH 7.4 and added to the chamber.

Statistical Analysis

The IEM results were expressed as the average and standard deviation of the number of gold particles observed per µm length of *B. burgdorferi* on an electron micrograph. The Wilcoxon ranked sum test was used to analyze the data. Significant differences were accepted when the P value was less than 0.05.

RESULTS

Isolation and Characterization of the *B. burgdorferi* Outer Membrane (OM)

Figure 1B:
Figure 1C:

The *B. burgdorferi* OM was removed and purified using methods developed for the isolation of the OM from *T. pallidum* and *Treponema vincentii* {Blanco, D. R., et al., *J. Bacteriol.*, 176:6088–6099 (1994)}. Modifications of the original procedure resulted in a more efficient release and recovery of the *B. burgdorferi* OM. These changes included a decrease in the concentration of citrate buffer pH 3.2 from 50 mM to 25 mM and the addition of 0.1% bovine serum albumin (BSA). The decrease in citrate buffer concentration resulted in a more efficient release of the OM of *B. burgdorferi* as assessed by whole mount electron microscopy (compare FIG. 1A to FIG. 1B). The decrease in the apparent diameter of citrate treated *B. burgdorferi* (approximately 250 nm in whole cells [FIG. 1A] to approximately 175 nm in citrate treated cells [FIG. 1B]) coupled with the appearance of vesicular material (FIG. 1B) suggested that the addition of citrate buffer pH 3.2 resulted in the efficient release of OM vesicles (OMV) from whole cells. The addition of BSA decreased the aggregation of the protoplasmic cylinders with the OMVs thereby increasing the overall recovery of the OMV material. Since a single membrane band was visible after centrifugation, it was not necessary to use octyidecyl rhodamine to visualize the OM band as in the case of *T. pallidum* {Blanco, D. R., et al, *J. Bacteriol.*, 176:6088–6099 (1994)}. Refractive index analysis indicated that the density of the OMV material, regardless of passage, was 1.13 g/ml (p=1.3852) or identical to the density of 31% (wt/wt) sucrose (data not shown). Whole mount electron microscopy demonstrated the membranous character of the OMV material which ranged in diameter from approximately 300 to 1000 nm (FIG. 1C). The absence of any detectable endoflagellar filaments by electron microscopy suggested that the low pH facilitated the depolymerization of the endoflagella into individual subunits as was observed for *T. pallidum* and *T. vincentii* {Blanco, D. R., et al., *J. Bacteriol.*, 176:6088–6099 (1994)}.

Absence of β-NADH Oxidase Activity in the Purified OMV Preparation

Figure 2:
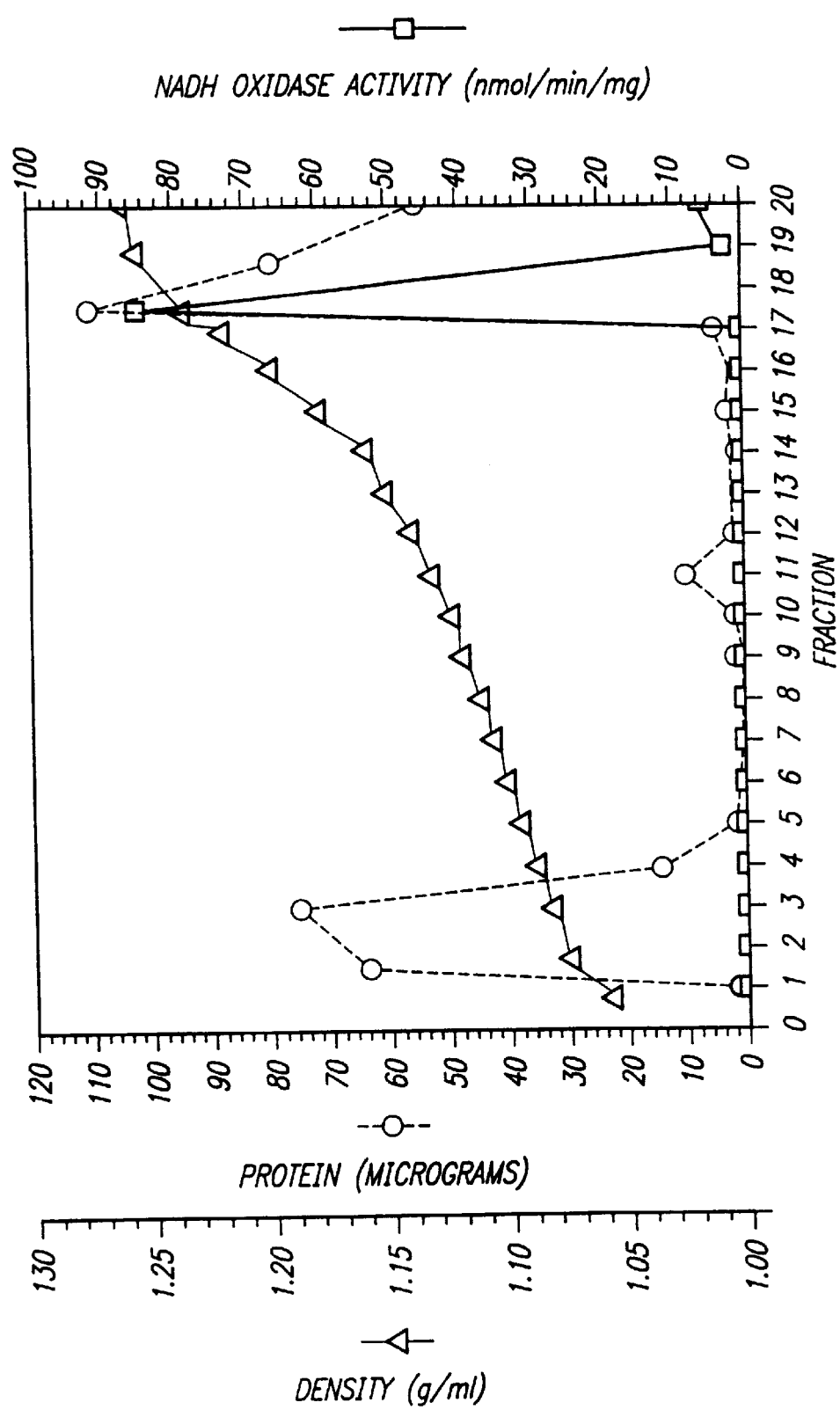
FIG. 2 presents identification of protoplasmic cylinder-associated β-NADH oxidase activity in B. burgdorferi. Outer membrane vesicles ("OMV") and protoplasmic cylinders derived from $2 \times 10^9$ B. burgdorferi were separated on a discontinuous sucrose gradient and fractionated as described in the Methods of Example 1. Fractions were tested for protein concentration (--○--), density (-▲-), and β-NADH oxidase specific activity (-■-). Fractions 11 and 18 correspond to the OMV and the protoplasmic cylinder fractions respectively.

Sucrose gradient fractions derived from $2 \times 10^9$ *B. burgdorferi* B31 avirulent ATCC were assayed for density, protein concentration, and β-NADH oxidase activity (FIG. 2). The OMV isolated for these assays had a density of 1.13 g/ml, identical to that observed in the OMV isolation described above, while the protoplasmic cylinders had a density of approximately 1.24 g/ml (FIG. 2). The protein distribution included soluble protein present in fractions 2 through 4, including the BSA added in the separation technique, OMV protein present in fraction 11, and protoplasmic protein present mostly in fraction 18. The results of the β-NADH oxidase assay indicated that activity resided only in the fraction containing the protoplasmic cylinder material (fraction 18) or samples more dense (fractions 19 and 20). The presence of DTT in all buffers and solutions used was essential in order to detect the β-NADH oxidase activity affiliated with the protoplasmic cylinders. Protoplasmic cylinders derived from citrate-treated *B. burgdorferi* lacked any detectable β-NADH oxidase activity if DTT was not added to the buffers and sucrose solutions (data not shown). The majority of the β-NADH oxidase activity, 91%, was associated with the protoplasmic cylinders while the remaining 9% was split between the final two fractions. No detectable β-NADH oxidase activity was affiliated with the fraction containing the OMV (fraction 11) derived from $2 \times 10^9$ B31 *B. burgdorferi*. Since this sample contained only 11 μg of OMV protein, we conducted β-NADH oxidase assays with 220 μg of OMV protein (derived from 20-fold more B31 *B. burgdorferi*) from OMV isolated from a sucrose gradient and concentrated by centrifugation. Even with this amount of OMV protein no β-NADH oxidase activity was detected. In contrast, when only $6.5 \times 10^8$ citrate-treated protoplasmic cylinders, corresponding to 35 μg of protein, were isolated from a sucrose gradient and concentrated by centrifugation, a β-NADH oxidase specific activity of approximately 60 nmol/min/mg was observed (data not shown). These results indicate that *B. burgdorferi* has an IM-associated β-NADH oxidase activity similar to that of *T. pallidum*. No soluble β-NADH oxidase activity was observed for *B. burgdorferi* in contrast to the soluble oxidase activity observed for *Serpulina hyodysenteriae* {Stanton, T. B., et al., *J. Bacteriol.*, 175:2980–2987 (1993)}.

Hydrophobic Protein Composition of OMV: Definition of Virulent Strain-Associated Outer Membrane Proteins Previous studies in our laboratory demonstrated that rabbits infected intradermally with as few as $4 \times 10^3$ *B. burgdorferi* B31 passage 4, were completely protected against EM and dermal infection following homologous intradermal challenge with $4 \times 10^7$ spirochetes {Foley, D. M., et al., *J. Clin. Invest.*, 96:965–975 (1995)}. In contrast, animals infected in a similar fashion with as many as $4 \times 10^7$ *B. burgdorferi* B31 passage 47, then challenged as described, were protected only against EM and not against dermal infection {Foley, D. M., et al., *J. Clin. Invest.*, 96:965–975 (1995)}; *B. burgdorferi* B31 avirulent ATCC is incapable of conferring any degree of protection against EM or dermal infection following challenge. Based on these findings, we hypothesized that there may be corresponding differences in the protein composition of the OMV derived from these various passages.

Figure 3A:
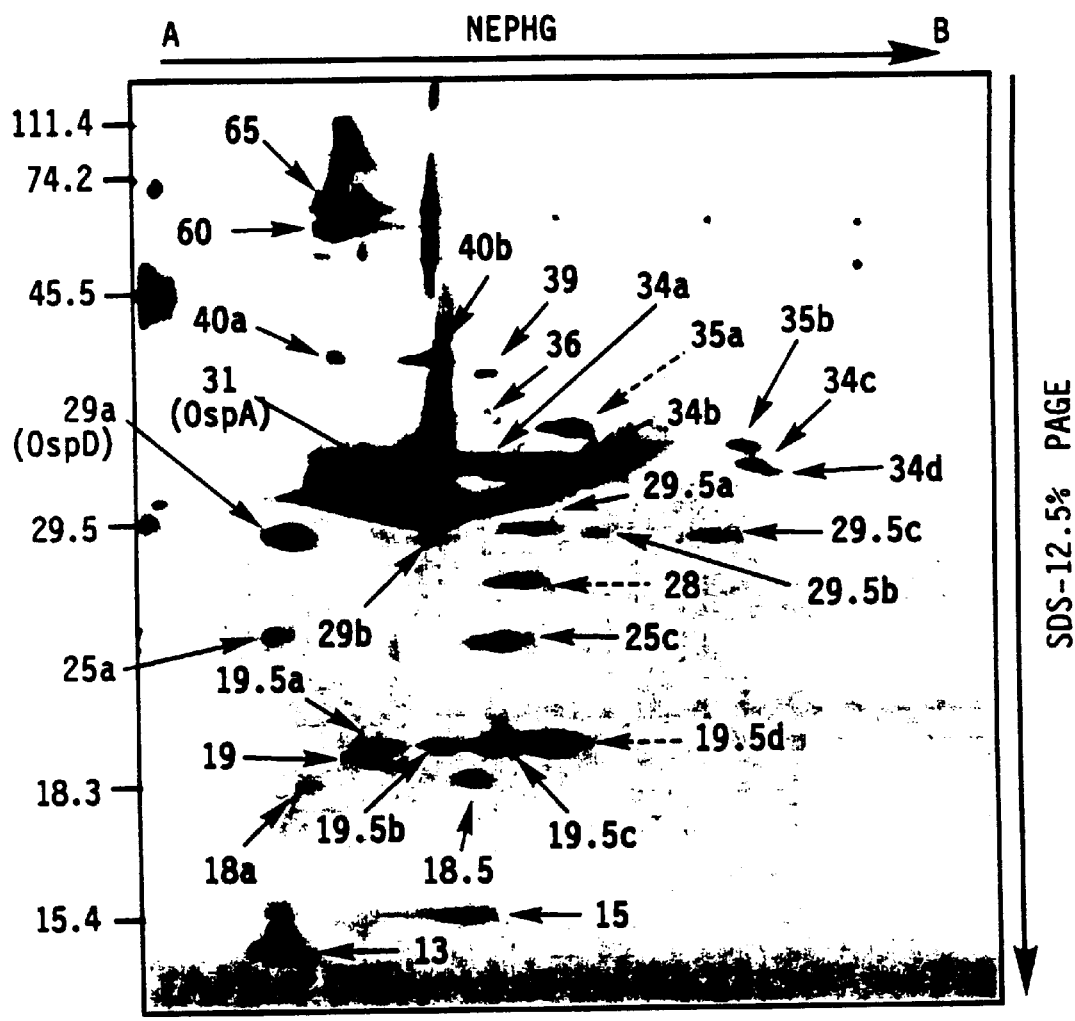
FIG. 3 presents two-dimensional profile of hydrophobic outer membrane ("OM") proteins from B. burgdorferi OMV. Triton X-114 detergent phase proteins were separated by 2D electrophoresis, blotted to PVDF membranes, and stained with colloidal gold. The italicized A and B indicate the acidic and basic ends of the NEPHG respectively. Italicized numbers and solid lines with arrowheads (→) denote proteins unique to the passage 10 B31 OMV. Italicized numbers and dotted lines with arrowheads (····▷) denote proteins observed in the passage 10 B31 and passage 48 B31 OMV. Italicized numbers and lines with open arrowheads (—▷) indicate proteins only observed in the passage 48 B31 OMV. Bold numbers and lines with filled arrowheads (—▶) designate proteins observed in either passage 10, passage 48, and the avirulent ATCC B31 OMV (see Table I). Lower case letters following the numbers listed distinguish proteins of identical molecular mass with different isoeletric points or pI values. The acidic-most spot is designated a; subsequent letter assignments refer to spots with more basic pI values.

In order to catalog the OM proteins, NEPHGE coupled with SDS-PAGE (i.e. two-dimensional gel electrophoresis [2D gel electrophoresis]) was utilized to resolve the TX-114 detergent phase proteins from the OMV derived from $5 \times 10^9$ *B. burgdorferi* (15–25 μg of protein). A colloidal gold stain of TX-114 detergent phase protein from the passage 10 B31 OMV consisted of 30 spots with molecular masses ranging from 13 kDa to 65 kDa (FIG. 3A and summarized in Table I). No differences were detected in the composition of the passage 10 B31 OMV proteins when they were compared to passage 4 B31 OMV proteins suggesting that passage 10 retained virulent strain-associated proteins (not shown).

Figure 3B:
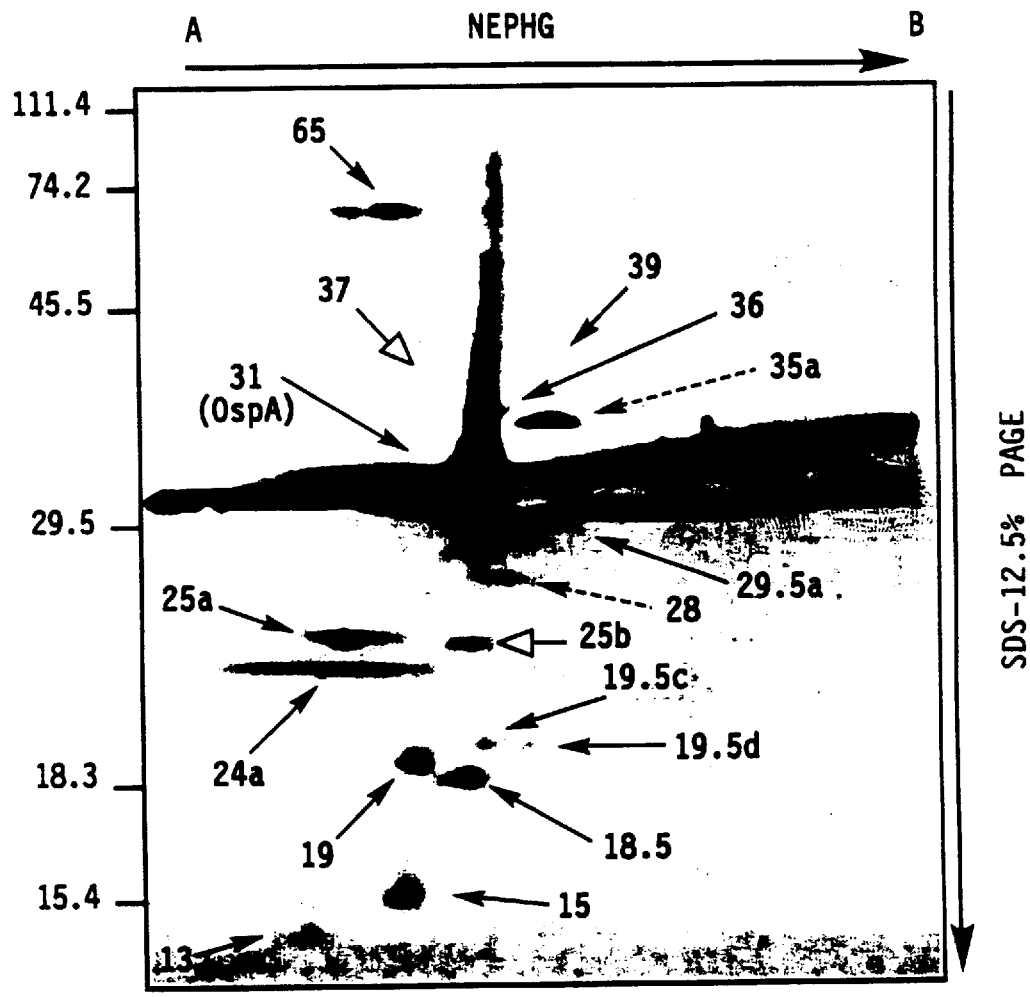
Figure 3C:
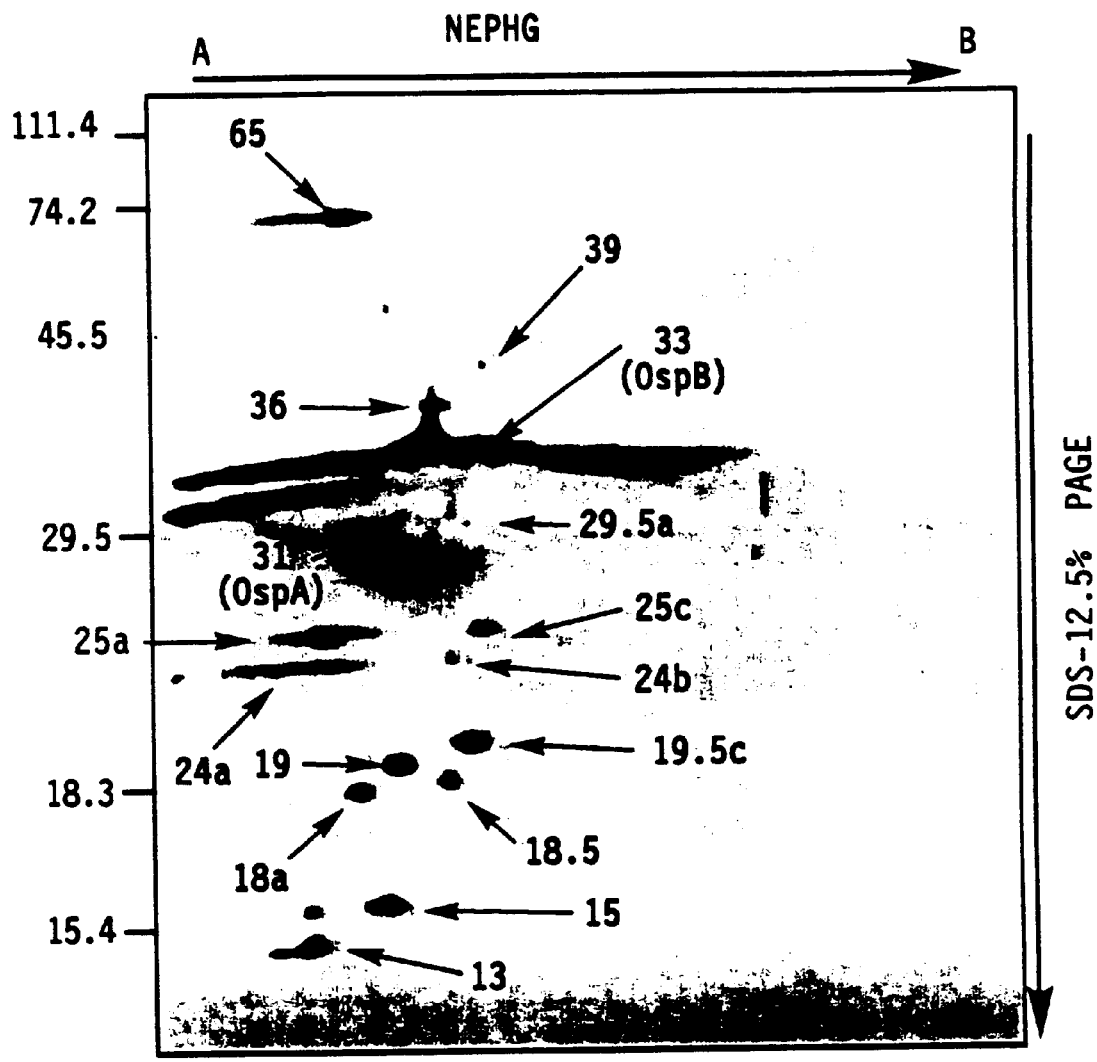

Comparison of the protein profiles of passage 48 B31 OMV (FIG. 3B) with the passage 10 B31 OMV *B. burgdorferi* (FIG. 3A and Table I) indicated that there were fourteen OM proteins uniquely found in the passage 10 OMV. In addition, there were two OM proteins unique to the passage 48 OMV (25b and 37, see Table I). The TX-114 detergent phase protein from the avirulent ATCC B31 OMV consisted of sixteen spots ranging from 13 kDa to 65 kDa, each with molecular masses and isoeletric points indistinguishable from proteins observed in either the passage 10 B31 or the passage 48 B31 OMV material with the exception of the avirulent ATCC B31 OMV unique protein designated 24b (FIG. 3C and Table I). In addition, the avirulent ATCC B31 OMV preparation contained significantly more of the 33-kDa protein. Comparison of these 2D profiles (FIGS. 3A, 3B, and 3C) with previously published 2D profiles {Norris, S. J. et al., *Infect. Immun.*, 60:4662–4672 (1992)} suggested that the abundant 31-kDa and 33-kDa proteins were the OspA and OspB lipoproteins, respectively, and that the 13-kDa species was an uncharacterized lipoprotein. ECL Western blotting with monoclonal antibodies (MAbs) specific for OspA and OspB confirmed that these proteins were OspA and OspB (not shown).

Nineteen proteins ranging in molecular mass from 19.5 kDa to 60 kDa (Table I), found in the passage 10 and passage 48 B31 OMV (FIGS, 3A and 3B) and absent from the avirulent ATCC B31 OMV (FIG. 3C), were designated as "virulent strain-associated". ECL Western blotting with polyclonal antibodies to OspD indicated that the virulent strain-associated 29a protein was the OspD lipoprotein {Norris, S. J. et al., *Infect. Immun.*, 60:4662–4672 (1992)} (data not shown).

The minor 39-kDa spot observed in all B31 OMV preparations was the monomeric endoflagellin (EF) protein based on its reactivity with anti-EF MAb H9724 (data not shown). The amount of contaminating EF varied in several independently derived OMV preparations. In some experiments, no EF was detected in the OMV material (data not shown) and in other experiments EF was a minor contaminant (as shown in FIGS. 3A–C). However, the profile of common candidate membrane-spanning proteins remained constant in all experiments regardless of the amount of EF contamination.

The only significant soluble protein contaminant present in the TX-114 aqueous phase was residual BSA used during the release of OMV as determined by colloidal gold staining and ECL immunoblot analysis with anti-BSA (not shown).

Antigenicity of *B. burgdorferi* Virulent Strain-associated Outer Membrane Proteins Serum containing antibodies specific for putative early-passage, virulent strain-associated proteins was created by depleting infection-derived rabbit serum of antibodies against common antigens of the virulent and avirulent ATCC B31 *B. burgdorferi* (see Methods). A recent report from our laboratory demonstrated that the adsorbed serum had been depleted of antibodies common to the in vitro-expressed proteins from whole cell lysates of virulent and avirulent ATCC isolates of *B. burgdorferi* strain B31 {Foley, D. M. et al., *J. Clin. Invest.*, 96:965–975 (1995)}. These results prompted us to determine if this absorbed serum would identify any virulent strain-associated proteins unique to the passage 10 B31 OMV material.

Figure 4A:
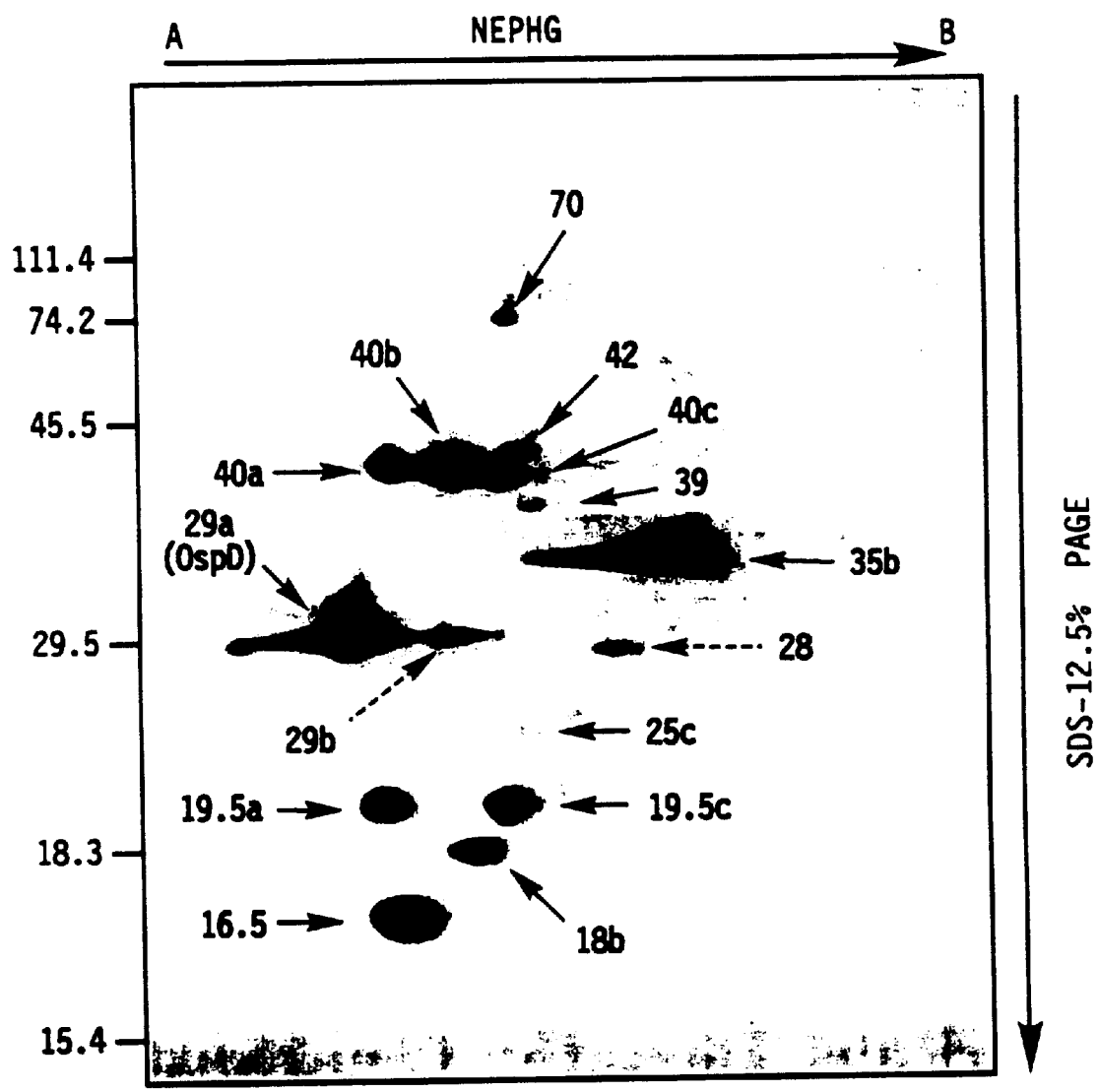
Figure 4B:
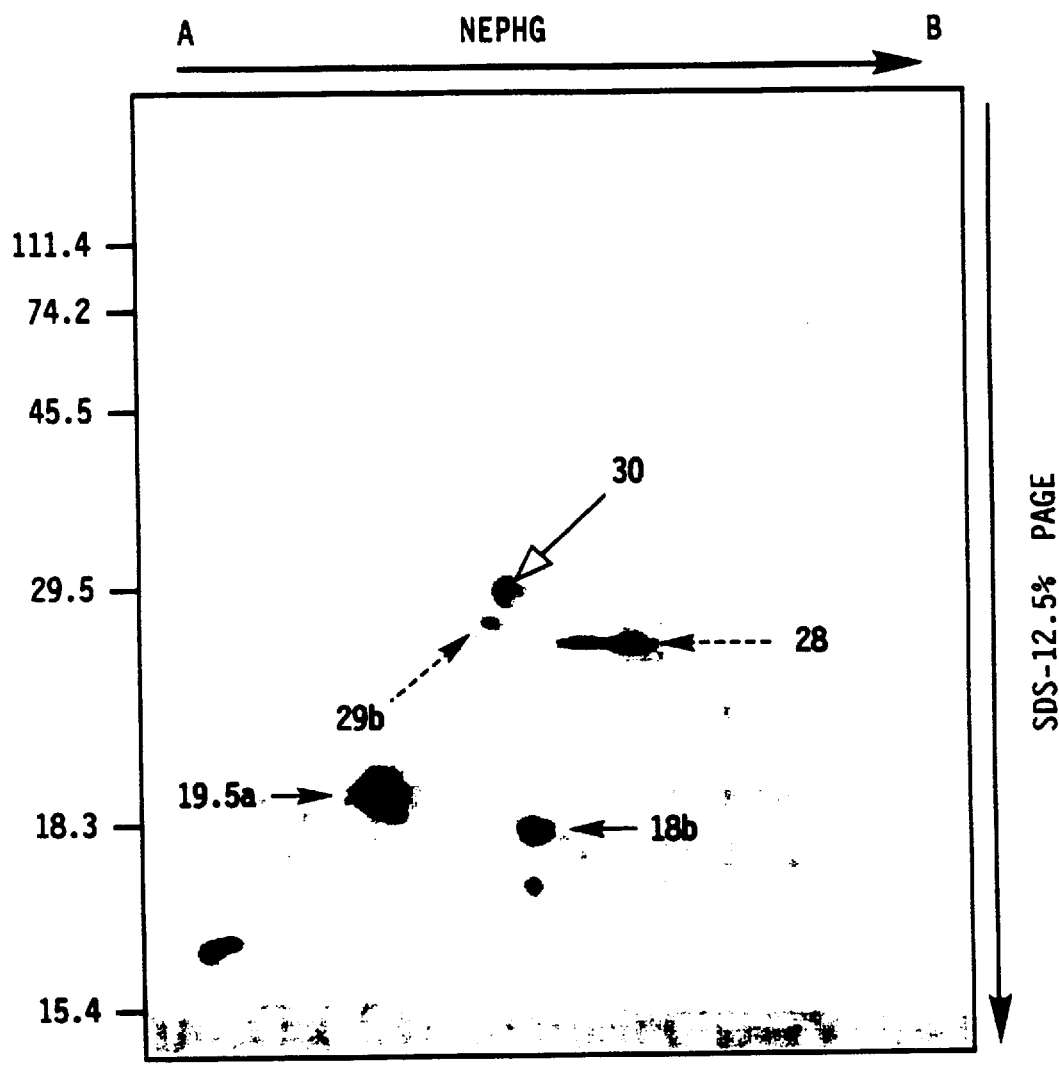
Figure 4C:
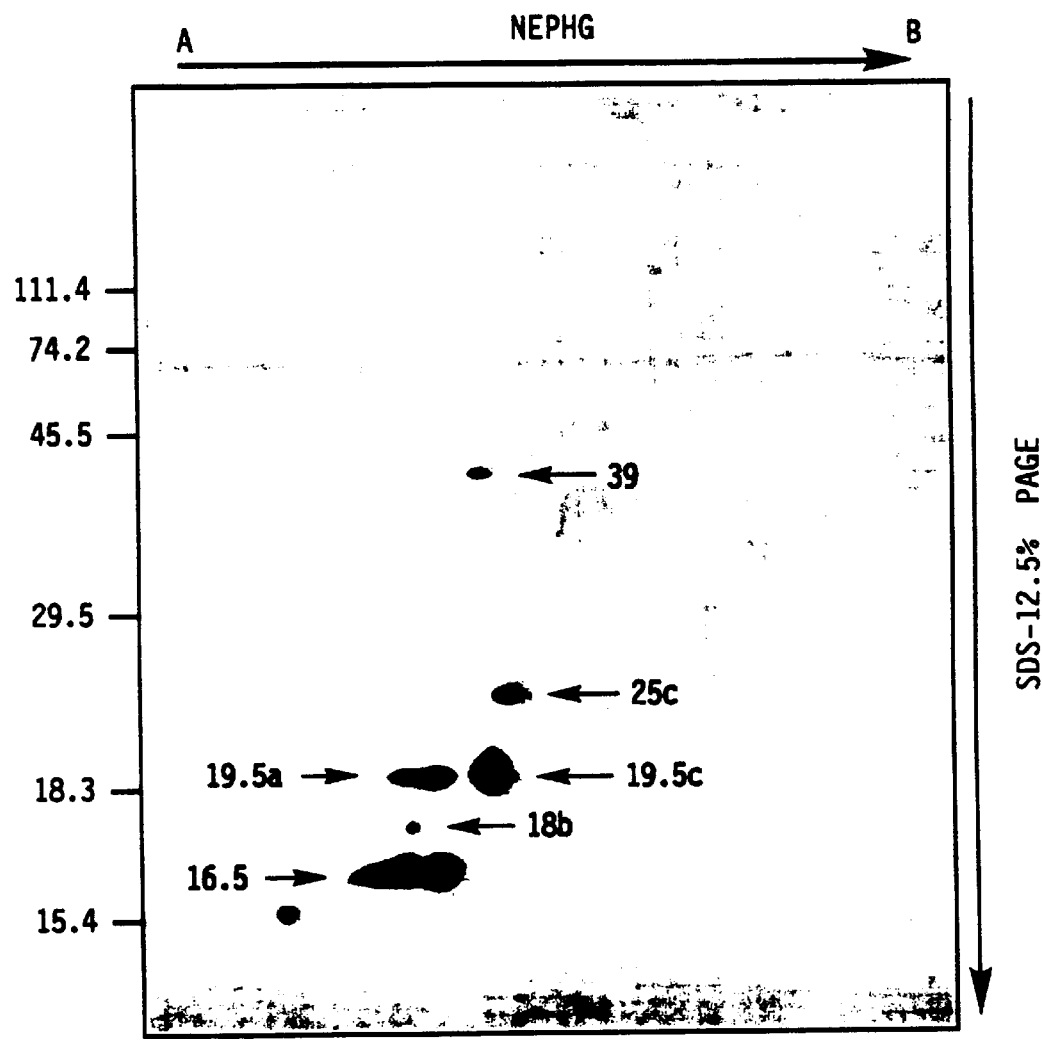

Immunoblots with the identical amount of TX-114 detergent phase OMV protein used for the compositional analysis in FIGS. 3A–C were probed with the adsorbed antiserum. OMV proteins of avirulent ATCC B31 strain retained some reactivity to the adsorbed serum as proteins of 16.5, 18, 19.5 (2 spots), 25, and 39 kDa were observed (FIG. 4C and Table II). However, the adsorbed serum bound 7 antigens found only in passage 10 B31 OMV; the molecular masses of the reactive species were 29 kDa (29a), 35 kDa (35b), 40 kDa (40a, 40b, and 40c), 42 kDa, and 70 kDa (FIG. 4A and Table II). Comparison of the OMV compositional protein profile (FIGS. 3A, 3B, and 3C) with the antigenic profile (FIGS. 4A, 4B, and 4C) indicated that the 29a, the 35b, the 40a, and the 40b antigens were observed in the colloidal gold-stained 2D profile of the passage 10 B31 OMV isolate but not in the passage 48 B31 or avirulent ATCC B31 OMV isolates. The remaining two antigens found uniquely in passage 10 B31 OMV, the 42-kDa and 70-kDa proteins, were not detected in the colloidal gold stain (FIG. 3A) yet were clearly identified in the respective immunoblot (FIG. 4A), most likely due to the high level sensitivity (in the picogram range for some antigen-antibody interactions) inherent to the ECL Western blotting system.

Surface-exposure of Virulent Strain-associated Proteins

Figure 5A:
Figure 5B:
Figure 5E:
Figure 5D:

Whole mount IEM was used to determine if the adsorbed serum with specificity for virulent strain-associated OMV proteins (described above) would recognize antigens located on the surface of *B. burgdorferi* B31 passage 1, passage 50, and avirulent ATCC whole cells. The findings are shown in FIG. 5 and summarized in Table III. The diameters of the organisms shown (between 230–250 nm) are consistent with those of whole intact cells {Barbour, A. G., et al., *Micro. Rev.*, 50:381400 (1986); Brusca, J. S., et al., *J. Bacteriol.*, 173:8004–8008 (1991); Walker, E. M., et al., *J. Bacteriol.*, 173:5585–5588 (1991); Radolf, J. D., et al. *J. Bacteriol.*, 176:21–31 (1994)} and endoflagella were not observed, indicating that the *B. burgdorferi* used were structurally intact. The gold particles observed thus correspond to antibody-bound surface antigens. Only a small number of gold particles were bound by B31 passage 1 whole cells in the presence of basal (pre-immune) serum (FIG. 5A). Unadsorbed immune serum recognized approximately 2-fold more surface antigens per μm length of the B31 passage 1 isolate than for either the passage 50 or the avirulent ATCC B31 isolates (FIG. 5B and Table III). Most importantly, the adsorbed immune rabbit serum (aIRS) recognized greater than 18-fold more surface antigens on the virulent B31 passage 1 cells (FIG. 5C) relative to the avirulent ATCC B31 cells (FIG. 5E) and approximately 4.5-fold more than the passage 50 cells (FIG. 5D). The statistical significance of these findings is shown in Table III.

Lipoprotein Composition of OMV Preparation

Figure 6A:
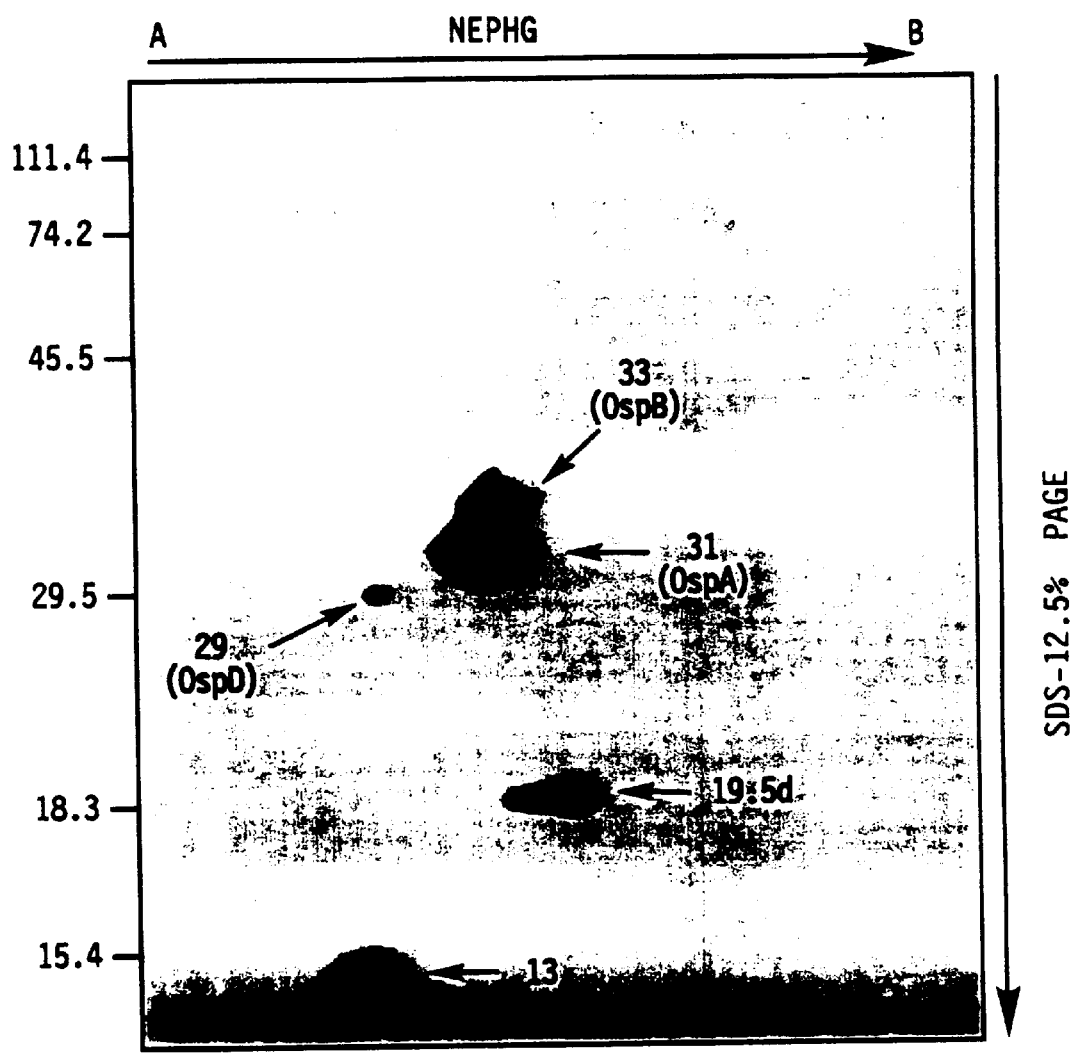
Figure 6B:
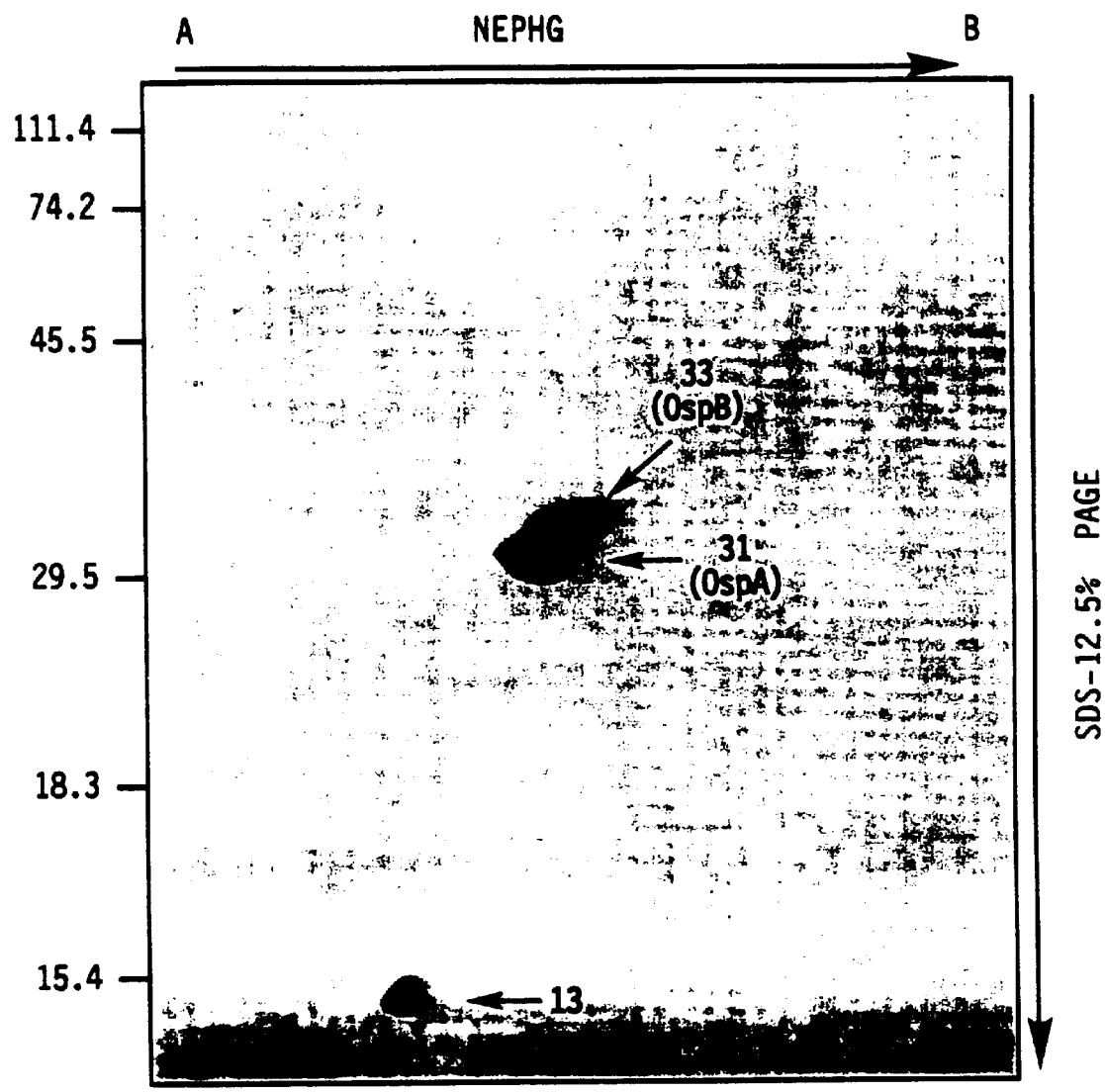
Figure 6C:
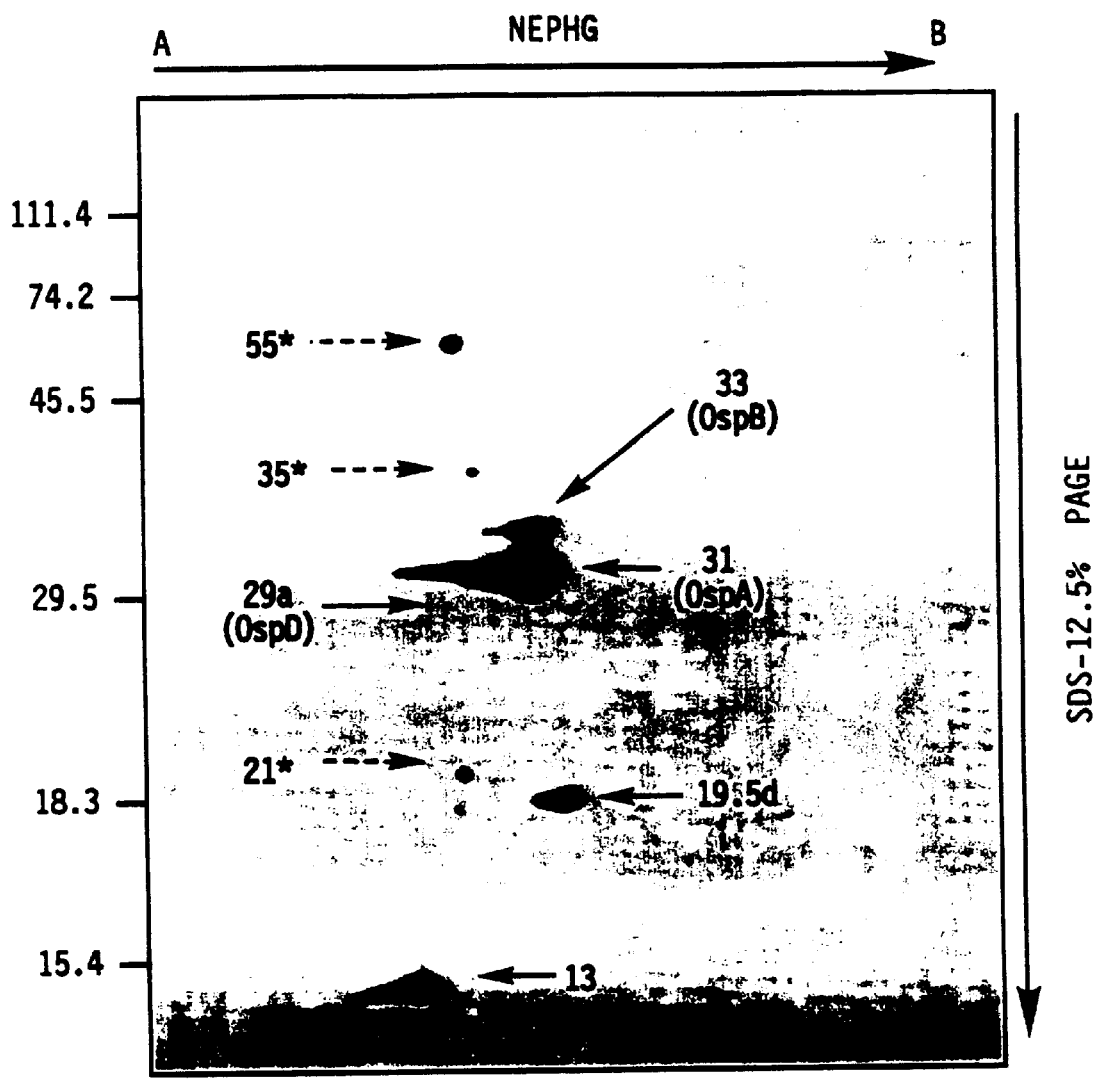

In order to determine if lipoproteins other than OspA, OspB, or OspD were present in the OMV preparations, passage 5 and avirulent ATCC B31 whole cells were labeled with [$^3$H]palmitate and the OM removed with citrate buffer. Hydrophobic OMV proteins were then analyzed by 2D gel electrophoresis as described in the Methods section. Comparison of passage 5 B31 OMV with avirulent ATCC B31 OMV (FIGS. 6A and 6B respectively) indicated that both preparations contained OspA, OspB, and a previously identified 13-kDa lipoprotein {Norris, S. J. et al., *Infect. Immun.*, 60:4662–4672 (1992)}. The passage 5 B31 OMV sample had additional lipoproteins with molecular masses of 29 kDa and 19.5 kDa (FIG. 6A). Based on its location and reactivity with OspD antibodies (data not shown), the 29-kDa spot was determined to be OspD {Norris, S. J. et al, *Infect. Immun.*, 60:4662–4672 (1992)}. The low-passage associated 19.5-kDa species (19.5d of FIG. 6A, Table I) migrated to approximately the same position as a 20-kDa lipoprotein previously reported by Norris, et al. {Norris, S. J. et al., *Infect. Immun.*, 60:4662–4672 (1992)}. Whole cells of B31 passage 5 (FIG. 6C) had three additional lipoproteins of 21 kDa, 35 kDa, and 55 kDa that were missing from the corresponding passage 5 B31 OMV preparation suggesting that these lipoproteins are inner membrane-associated. It is likely that the 21-kDa lipoprotein corresponds to the acidic 20-kDa lipoprotein reported by Norris, et al. {Norris, S. J. et al., *Infect. Immun.*, 60:4662–4672 (1992)}. The 35-kDa and 55-kDa lipoproteins correspond to previously described 37-kDa and 53-kDa lipoproteins {Brandt, M. E., et al., *Infect. Immun.*, 58:983–991 (1990)}.

Porin Activity of the *B. burgdorferi* OMV Preparation

Addition of TX-100 solubilized OMV derived from virulent or avirulent *B. burgdorferi* strain B31 to the planar lipid bilayer system resulted in a step-wise increase in the membrane conductance. Two porin activities were identified with conductances of approximately 0.6 nS and 12.6 nS (FIG. 7A and inset). The channel sizes observed were identical for both virulent passage 10 B31 OMV and avirulent ATCC B31 OMV. The average size of the observed channels were 0.595 nS for the 97 insertional events observed for the small channel (FIG. 7B) and 12.6 nS for the 348 insertional events observed for the large channel (FIG. 7C). The calculated average conductances suggested that the diameter of the small and large channels were 0.6 nm and 3.2 nm respectively, assuming that the height of both channels was 6 nm {Hancock, R. E. W., "Model membrane studies of porin function", In Bacterial Outer Membranes as Model Systems, M. Inouye, ed. John Wiley and Sons, New York, 187–225 (1986)}. No channels were observed when TX-100 alone was added to the bilayer system at the concentration used to solubilize the OMV material. Also, no differences in the properties of the porin channels were observed between solvent-free and solvent-containing bilayers.

DISCUSSION

Although nearly fourteen years have elapsed since the identification of *B. burgdorferi* as the etiologic agent of Lyme disease {Burgdorfer, W., et al., *Science*, 216:1317–1319 (1982); Steere, A. C., et al., *N. Eng. J. Med.*, 308:733–740 (1983)}, the contribution of its outer membrane (OM) proteins to pathogenesis is poorly understood. Typical bacterial OMs contain proteins of two distinct topological categories. Outer membrane spanning proteins contain multiple transmembrane segments of amphipathic beta-sheet structure, such as porins. The second category, lipoproteins, have a lipid moiety anchored to the inner leaflet of the OM and a periplasmic protein moiety. It is the outer membrane spanning proteins of many pathogenic bacteria which are known to mediate essential steps in pathogenesis, such as adhesion {Miller, V. L., et al., *J. Bacteriol.*, 172:1062–1069 (1990); Jerse, A. E., et al., *Proc. Natl. Acad. Sci. USA*, 87:7938–7843 (1990)}, invasion {Isberg, R. R., et al., *Cell* 50:769–778 (1987); Makino, S., et al., *EMBO J.* 10:1307–1315 (1991); Weel, J. F., et al., *J. Exp. Med.*, 173:1395–1405 (1991); Galan, J. E., et al., *J. Bacteriol.*, 174:4338–4349 (1992); Bemardini, M. L., et al., *Infect. Immun.*, 61:3625–3635 (1993)}, and serum resistance {Bliska, J. B., et al., *Proc. Natl. Acad. Sci USA*, 89:3561–3565 (1992); Heffernan, E. J., et al.,*J. Clin. Invest.*, 90:953–964 (1992); Pierson, D. E., et al., *Infect. Immun.*, 61:1846–1852 (1993); Fernandez, R. C., et al., *Infect. Immun.*, 62:4727–4738 (1994)}. In contrast, most studies on pathogenesis and immunity in Lyme disease have focused on *B. burgdorferi* lipoproteins, such as OspA {Fikrig, E., et al., *Science*, 250:553–556 (1990); Simon, M. M., et al., *J. Inf. Dis.*, 164:123–132 (1991); Fikrig, E., et al., *Infect. Immun.*, 60:773–777 (1992); Fikrig, E., et al., *Infect. Immun.*, 60:657–661 (1992); Fikrig, E., et al., *J. Immunol.*, 148: 2256–2260 (1992); Fikrig, E., et al., *Proc. Natl. Acad. Sci USA*, 89:5418–5421 (1992); Bergstrom, S., et al., *Mol. Microbiol.*, 3:479–486 (1989)}, whose principle cellular location appears to be subsurface {Brusca, J. S., et al., *J. Bacteriol.*, 173:8004–8008 (1991)}. In the time since we demonstrated the existence of *B. burgdorferi* OM spanning proteins by freeze-fracture analysis {Walker, E. M., et al.,*J. Bacteriol.*, 173:5585–5588 (1991)}, our studies have been directed toward identification of these proteins and eludication of their role in pathogenesis.

Porins are prototypical OM spanning proteins {Hancock, R. E., In Bacterial Outer Membranes as Model Systems, M. Inouye, ed. John Wiley and Sons, New York, 187–227 (1986); Jeanteur, D., et al., *Mol. Microbiol.*, 5:2153–2164 (1991); Cowan, S. W., et al., *Nature* (London), 358:727–733 (1992)}. In this study, we have isolated the OMV of *B. burgdorferi* and have demonstrated that this OMV material has two distinct porin activities, as expected for vesicles derived from the OM. When the *B. burgdorferi* OMV preparation was solubilized with detergent and added to an in vitro bilayer system, two separate conductances were observed, one of approximately 0.6 nS and the other approximately 12.6 nS (FIG. 7A). These two porin activities resemble the two types of porins characterized in other spirochetes. The small 0.6 nS channel is similar in size to the 0.7 nS Tromp1 porin recently identified in *T. pallidum* {Blanco, D. R., et al., *J. Bacteriol.*, 177:3556–3562 (1995)} and the 1.1 nS OmpL1 porin from *L. kirschneri* {Shang, E. S., et al., *Infect. Immun*, 63:3174–3181 (1995)} while the large 12.6 nS channel is in the same range as the 7.7 nS porin characterized in *Spirocheta aurantia*{Kropinski, A. M., et al., *J. Bacteriol.*, 169:172–179 (1987)} and the 10.9 nS porin reported for *Treponema denticola* {Egli, C. W., et al., *Infect. Immun.*, 61:1694–1699 (1993)}. The histogram in FIG. 7B depicts the number of small channels observed which showed an average conductance of 0.595 nS for the majority of the insertional events. Approximately 20% of the channels observed were much smaller in size (with approximately 50 pS conductance) and may either reflect another smaller porin or a conformational variant of the smaller channel that has an anomalous conductance. We also noted that the small channel had a characteristic "flickering" signature similar to that reported for other porin proteins including the porin of *Mycobacterium chelonae* {Trias, J., et al., *J. Biol. Chem.*, 268:6234–6240 (1993)}. However, partial purification of the channel with conductance of 0.6 nS significantly reduces the "flickering" activity, implying that the presence of other proteins within our total detergent solubilized OMV preparation contribute to this phenomenon.

The possibility that the large porin could represent an aggregated form of the small channels seems unlikely based on the 348 observed large channel insertions that were of uniform size (FIG. 7C). If the small channels did form aggregates, then a heterogeneity in channel size ranging between 0.6 nS and 12.6 nS would be observed. The fact that the large channel forms 348 pores that range mostly in size from 10 to 14 nS with a clear peak at approximately 12.5 nS indicates that this channel is a stable porin protein.

Several additional lines of evidence indicate that the vesicles are of OM origin, contain other OM spanning proteins, and lack contamination with soluble proteins and inner membrane proteins. Our efforts to isolate *B. burgdorferi* OMV were based upon our experience in isolating *T. pallidum* OMV {Blanco, D. R., et al., *J. Bacteriol.*, 176:6088–6099 (1994)}. Electron micrographs of the effects of treatment of *B. burgdorferi* with hypotonic citrate buffer at pH 3.2 (FIG. 1) mirrored that which was observed following similar treatment of *T. pallidum* {Blanco, D. R., et al., *J. Bacteriol.*, 176:6088–6099 (1994)}. Protoplasmic cylinders appeared reduced in diameter compared with intact spirochetes, as expected, but appeared otherwise intact; endoflagella were not seen, and membranous vesicles were released. Taken together, these observations are consistent with the selective release of outer membrane vesicles.

Previous attempts to isolate and identify OM proteins from *B. burgdorferi* have been impeded by the fragility of the OM structure {Barbour, A. G., et al., *Microbiol. Rev.*, 50:381–400 (1986); Holt, S. C., *Microbiol. Rev.*, 42:114–160 (1978)} and the observation that *B. burgdorferi* membranes "bleb" in vitro {Barbour, A. G., et al., *Micro. Rev.*, 50:381–400 (1986); Garon, C. F., et al., *Scanning Microscopy*, 3 (Suppl.):109–115 (1989); Shoberg, R. J., et al., *Infect. Immun.*, 61:3892–3900 (1993)}. These membrane blebs contain DNase I resistant plasmid DNA suggesting that they were at least partially derived from the inner membrane {Garon, C. F., et al., *Scanning Microscopy*, 3 (Suppl.):109–115 (1989)}. Recently Bledsoe, et al. {Bledsoe, H. A., et al., *J. Bacteriol.*, 176:7447–7455 (1994)} have reported separation of *B. burgdorferi* IM from OM using isopynic centrifugation of French pressure cell disrupted *B. burgdorferi* that yielded IM, OM, and hybrid membrane bands. This OM material had a significantly greater density (1.19 g/ml) than the OMV material reported here (1.13 g/ml) perhaps due to differences in cell wall contamination. Single dimension protein profiles observed in the Bledsoe, et al. report {Bledsoe, H. A., et al., *J. Bacteriol.*, 176:7447–7455 (1994)} were similar to our OMV preparations both in complexity and protein amounts, including high levels of the OspA lipoprotein. Comparisons between the two 2D profiles indicate that some similarities may exist between these two OM preparations; however, it is difficult to correlate the spots observed in their OM 2D when compared to FIG. 3A since the separation of protein in the Bledsoe, et al. first dimension NEPHG {Bledsoe, H. A., et al., *J. Bacteriol.*, 176:7447–7455 (1994)} appears to be broader than that observed with our NEPHG. The colloidal gold stain shown in FIG. 3A has more overall protein spots than the Bledsoe, et al. OM 2D. This, coupled with the aforementioned protein complexity of the Bledsoe, et al. single dimension OM protein profile {Bledsoe, H. A., et al., *J. Bacteriol.*, 176:7447–7455 (1994)}, suggests that the differences observed in the 2D profiles may be due to increased amounts of OMV protein loaded in our gel system (FIG. 3).

The hydrophobic nature of candidate OM proteins composing the OMV is expected for a purified outer membrane preparation. Low levels of endoflagellin, dissociated into monomers by exposure to pH 3.2, were found in some preparations of OMV. While contamination with endoflagellin (EF) was variable, the presence of the other 33 proteins in the hydrophobic detergent phase has been fully reproducible for each virulent strain-associated OMV preparation.

Thirteen proteins, including one spot only observed by immunoblotting (18b, Tables I and II), were common between OMV of passage 10, 48, and avirulent ATCC B31. Passage 10 B31 OMV had 20 proteins in addition to those shared with ATCC B31, including three which were detected only with the ATCC B31 adsorbed antiserum from immune rabbits. The fact that there are proteins common to OMV from each of the B31 passages, and proteins unique to the virulent passages, strongly supports the notion that the unique and reproducible OMV composition of each passage indeed reflects proteins of OM origin.

Three OMV proteins are common to both the passage 10 and passage 48 isolate. Because the passage 48 isolate retains infectivity in the rabbit model of Lyme borreliosis {Foley, D. M. et al., *J. Clin. Invest.*, 96:965–975 (1995)}, these three OMV proteins, designated 19.5d, 28, and 35a (Table I), may be important for the initial establishment of infection and the development of EM. The role of these OM proteins in the pathogenesis of Lyme disease awaits further analysis.

Of the proteins found in the OMV of B31 passage 5 spirochetes, only 5 were palmitate-labeled lipoproteins including OspA, OspB, and OspD {Norris, S. J. et al., *Infect. Immun.*, 60:4662–4672 (1992)}. Given the fact that the amount of OspD appears roughly equivalent to many other OMV proteins which do not appear to be acylated, it is unlikely that sensitivity of detection is a factor in lipoprotein detection under these conditions. Therefore it is highly likely that the hydrophobic proteins which are not labeled with palmitate are outer membrane spanning proteins.

While some hydrophobic OMV proteins could be contaminants of inner membrane origin, several lines of evidence argue against this possibility. First, we used the known bacterial IM marker, β-NADH oxidase {Osborn, M. J., et al., *J. Biol. Chem.*, 247:3962–3972 (1972); Thom, J. R., et al., *J. Bacteriol.*, 170:5654–5661 (1988); Norris, S. J., et al., *Microbiol. Rev.*, 57:750–779 (1993); Radolf, J. D., et al., *Infect. Immun.*, 63:2154–2163 (1995)}, to assess the degree of IM protein contamination in our OMV preparation. β-NADH oxidase activity has been reported for several spirochetes, most recently *B. burgdorferi* {Radolf, J. D., et al., *Infect. Immun.*, 63:2154–2163 (1995)}. No β-NADH oxidase activity was detected from OMV derived from $2 \times 10^9$ *B. burgdorferi* (corresponding to 11 μg of OMV protein; FIG. 2). Further, no β-NADH oxidase activity was observed when 220 μg of the OMV protein was assayed. In contrast, 35 μg of protein from $6.5 \times 10^8$ protoplasmic cylinders showed significant β-NADH oxidase activity (60 nmol/min/mg; data not shown). The presence of DTT was critical for the detection of β-NADH oxidase activity as evidenced by the absence of any protoplasmic cylinder-associated activity in the absence of DTT. The 2D OMV protein profiles were identical whether DTT was present or absent indicating that DTT did not alter the isolation of *B. burgdorferi* candidate OM proteins (data not shown). More importantly, the absence of β-NADH oxidase activity indicates that no IM protein contaminants are present in our OMV preparation. Second, we compared the 2D protein profile of *B. burgdorferi* B31 passage 5 whole cells intrinsically labeled with [$^3$H]palmitate (FIG. 6C) with OMV material obtained from the same [$^3$H]palmitate-labeled culture (FIG. 6A). We reasoned that lipoproteins whose cellular location was at least in part within the OM would be observed in both the OMV and whole cell samples whereas IM lipoproteins would only be observed in the whole cell sample and not in the OMV 2D profile. Three lipoproteins with molecular masses of 21 kDa, 35 kDa, and 55 kDa are present only in the [$^3$H]palmitate-labeled whole cells (FIG. 6C) and are absent in the OMV 2D profile (FIG. 6A); these findings suggest that these three lipoproteins are found exclusively in the IM. If the OMV preparation contained significant contamination with IM proteins, the three IM-associated lipoproteins would be observed in the OMV 2D profile. In addition, the equal or greater intensity in whole cell extracts of these lipoproteins as compared to the OspD lipoprotein, known to be OM associated, indicates that if these lipoproteins were a component of the OM, they should be of equal or greater intensity than observed in FIG. 6A for OspD. Finally, the colloidal gold stained passage 10 OMV 2D protein profile (FIG. 3A) lacks the 21 kDa, 35 kDa, and 55 kDa proteins indicating that these putative IM proteins are not present in our OM material.

Although OspA has been described as a surface exposed protein {Fikrig, E., et al., *Science*, 250:553–556 (1990); Simon, M. M., et al., *J. Inf. Dis.*, 164:123–132 (1991); Fikrig, E., et al., *Infect. Immun.*, 60:773–777 (1992); Fikrig, E., et al., *Infect. Immun.*, 60:657–661 (1992); Fikrig, E., et al., *J. Immunol.*, 148:2256–2260 (1992); Fikrig, E., et al., *Proc. Natl. Acad. Sci. USA*, 89:5418–5421 (1992); Bergstrom, S., et al., *Mol. Microbiol.*, 3:479–486 (1989)}, the majority of OspA appears associated with the IM {Brusca, J. S., et al., *J. Bacteriol.*, 173:8004–8008 (1991)}. While OspA is the most abundant protein in the OMV preparation, most OspA is still found in the protoplasmic cylinders after release of OMV with citrate buffer (data not shown). Localization of spirochetal lipoproteins to both the IM and OM has also been observed for the TmpA and the 17 kDa lipoproteins of *T. pallidum* {Blanco, D. R., et al., *J. Bacteriol.*, 176:6088–6099 (1994); Schouls, L. M., et al., *Microb. Pathog.*, 7:175–188 (1989); Akins, D. R., et al., *Infect. Immun.*, 61:1202–1210 (1993)}. Spirochetes have a unique membrane organization in regard to lipoproteins; i.e., there are lipoproteins associated with the OM such as OspD {Norris, S. J. et al., *Infect. Immun.*, 60:4662–4672 (1992)}, lipoproteins that are associated with the IM, such as the 55 kDa lipoprotein, and lipoproteins that are associated with both the IM and OM such as OspA {Brusca, J. S., et al., *J. Bacteriol.*, 173:8004–8008 (1991)}.

Recently we have reported that infection of rabbits with *B. burgdorferi* B31 passage 4 results in the development of complete immunity to reinfection {Foley, D. M. et al., *J. Clin. Invest.*, 96:965–975 (1995)}. The ability to induce protective immunity is diminished with progressive in vitro cultivation. Infection with *B. burgdorferi* B31 passage 27 ultimately results in partial protection against development of erythema migrans (EM), and complete protection against skin infection. Infection with *B. burgdorferi* B31 passage 47 confers partial protection against EM, but no protection against chronic skin infection. Inoculation of *B. burgdorferi* avirulent ATCC B31 results in neither infection nor development of infection-derived immunity. In this context, we regard the changes in OMV hydrophobic protein composition which occur during sequential in vitro passage as particularly significant. Therefore, we attempted to correlate these changes with infectivity and with ability of *B. burgdorferi* to induce protective immunity against EM and skin infection in an effort to identify *B. burgdorferi* proteins involved in Lyme disease pathogenesis.

We have recently described the preparation of an infection-derived antiserum to virulent *B. burgdorferi* that was adsorbed with the avirulent ATCC isolate to remove antibodies that recognize antigens common to both the virulent and avirulent *B. burgdorferi* {Foley, D. M. et al., *J. Clin. Invest.*, 96:965–975 (1995)}. The resulting adsorbed serum contained antibodies specifically enriched for low-passage, virulent *B. burgdorferi* antigens, and was depleted of antibodies to antigens found in the avirulent ATCC B31 strain. When this adsorbed serum was used to identify antigens unique to the virulent OMV material, 7 spots were observed (FIG. 4A) that were not present in either the passage 48 or the avirulent OMV isolate (FIG. 4C) when equivalent amounts of protein were analyzed. Two antigens (28 and 29b of Table II) common to the virulent passage 10 B31 OMV and passage 48 B31 OMV were recognized by the adsorbed serum. As mentioned above, these proteins may be essential for the initial establishment of infection and the development of EM. Further, antibodies against these antigens may protect against challenge with virulent *B. burgdorferi*. Because of their possible roles in pathogenesis and infection derived immunity, we are currently focusing on cloning the genes encoding the 28 and 29*b* antigens. The 29 kDa protein observed in the passage 10 B31 OMV and passage 48 B31 OMV immunoblots was not the OspD lipoprotein based on its location in the NEPHG 2D system and its lack of reactivity with polyclonal anti-OspD serum (data not shown).

Figure 5C:

Findings with whole mount IEM using the avirulent ATCC adsorbed serum reacted against virulent passage 1, infectious passage 50, and the avirulent ATCC B31 *B. burgdorferi* (FIG. 5) parallel the observations made for the compositional colloidal gold-stained profile and subsequent immunoblot analyses of all three of these *B. burgdorferi* isolates. The adsorbed serum was found to be more reactive with the virulent isolate than the avirulent isolate. The observation that the adsorbed serum contains antibodies that specifically and preferentially bind the surface of the virulent B31 passage 1 *B. burgdorferi* relative to the B31 passage 50 and avirulent ATCC B31 spirochetes indicates that the adsorbed serum, as predicted, is a reagent enriched for antibodies specific for early passage and therefore presumably virulent strain-associated antigens. Further, the adsorbed antiserum recognizes surface exposed proteins, indicating that this reagent contains antibodies directed against virulent strain-associated candidate OM proteins. Presumably, some of the antigens recognized in the passage 10 B31 OMV 2D profile (FIG. 4A) are surface exposed antigens observed in the whole mount IEM of passage B31 *B. burgdorferi* (FIG. 5B and FIG. 5C). The number of gold particles observed for *B. burgdorferi* whole cells in the IEM experiment decreased with increasing in vitro passage consistent with the decrease in proteins observed in the compositional and antigenic profiles of the various OMV preparations analyzed (FIGS. 3 and 4).

These findings suggest that the same proteins are being detected by these independent techniques. This further supports the idea that the proteins identified in the OMV are OM proteins. Definitive proof that the candidate Oms proteins are authentic Oms proteins will require the cloning and sequencing of the genes encoding these proteins followed by the localization of these proteins to the OM of *B. burgdorferi*. Determination of correspondence between the individual antigens observed in our OMV material with the surface exposed OM proteins detected by IEM is an important goal of work in progress in our laboratory.

We have chosen the acronym, "Oms", to designate the outer membrane spanning proteins shared by virulent and avirulent *Borrelia burgdorferi* strain B31. We have also chosen the acronym, $Oms^{vsa}$, for Oms that are virulent strain-associated, to designate those candidate outer membrane spanning proteins found in virulent, but not the avirulent ATCC B31 strain. Because $Oms^{vsa}$ include, as our immunoelectron microscopic findings indicate, surface antigens lost upon progressive in vitro cultivation, it is likely that among the $Oms^{vsa}$ are candidate OM proteins which are relevant to the pathogenesis of experimental Lyme disease. While the $Oms^{vsa}$ described here are found in *B. burgdorferi* after in vitro cultivation, it is certainly possible that there are candidate $Oms^{vsa}$ which are only expressed in vivo in environments unique to the vertebrate and invertebrate host of *B. burgdorferi*. Consistent with this possibility, we have recently reported a supercoiled plasmid encoded protein, EppA, that is apparently expressed only during infection {Champion, C. I., et al, *Infect. Immun.*, 62:2653–2661 (1994)}.

The efficacy of Oms and $Oms^{vsa}$ as vaccine candidates and protective immunogens can be tested using methods known in the art such as described in Fikrig, et al., *Science*, 250:553–556 (1990). The efficacy of vaccination with Oms relative to OspA in animal models of Lyme disease can also be similarly tested.

TABLE I

Hydrophobic Protein Composition of OMV Preparations Based on Colloidal Gold Staining (Molecular Mass in kD)

| Passage 10 B31 | Passage 48 B31 | Avirulent ATCC B31 | Description |
|---|---|---|---|
| 13 | 13 | 13 | L, C |
| 15 | 15 | 15 | Oms, C |
| 18a |  | 18a | Oms |
| 18.5 | 18.5 | 18.5 | Oms, C |
| 19 | 19 | 19 | Oms, C |
| 19.5a* |  |  | Oms, vsa‡ |
| 19.5b |  |  | Oms, vsa‡ |
| 19.5c | 19.5c | 19.5c | Oms, C |
| 19.5d | 19.5d |  | L, vsa§ |
|  | 24a | 24a* | Oms |
|  |  | 24b | Oms |
| 25a* | 25a* | 25a* | Oms, C |
|  | 25b |  | Oms, vsa‖ |
| 25c |  | 25c | Oms |
| 28 | 28 |  | Oms, vsa§ |
| 29a (OspD) |  |  | L, vsa‡ |
| 29b |  |  | Oms, vsa‡ |
| 29.5a* | 29.5a* | 29.5a* | Oms, C |
| 29.5b |  |  | Oms, vsa‡ |
| 29.5c |  |  | Oms, vsa‡ |
| 31 (OspA) | 31 (OspA) | 31 (OspA) | L, C |
| (33, OspB)¶ | (33, OspB)¶ | 33 (OspB) | L, C |
| 34a* |  |  | Oms, vsa‡ |
| 34b |  |  | Oms, vsa‡ |
| 34c |  |  | Oms, vsa‡ |
| 34d |  |  | Oms, vsa‡ |
| 35a* | 35a |  | Oms, vsa§ |
| 35b |  |  | Oms, vsa‡ |
| 36 | 36 | 36 | Oms, C |
|  | 37 |  | Oms, vsa‖ |
| 39 | 39 | 39 | C, EF** |
| 40a* |  |  | Oms, vsa‡ |
| 40b |  |  | Oms, vsa‡ |
| 60 |  |  | Oms, vsa‡ |
| 65 | 65 | 65 | Oms, C |

L, lipoprotein; Oms, candidate outer membrane-spanning protein; C, protein common to all OMV preparations;
*for proteins with identical molecular masses, a designates the most acidic protein and the subsequent letters indicate proteins that are more basic;
‡vsa, virulent strain-associated protein present only in passage 10 OMV preparation (FIG. 3 A);
§vsa, virulent strain associated protein present in passage 10 and 48 OMV preparations FIG. 3, A and B);
‖vsa, virulent strain associated protein present only in passage 48 OMV preparation (FIG. 3 B);
¶only detected by [$^3$H]palmitate labeling (FIG. 6 A) or ECL immunoblot analysis with anti-OspB monoclonal antibody (data not shown);
**endoflagellin (EF).

TABLE II

Hydrophobic OMV Antigens Recognized by Immunoblotting with Adsorbed Sera (Molecular Mass in kD)

| Passage 10 B31 | Passage 48 B31 | Avirulent ATCC B31 | Description |
|---|---|---|---|
| 16.5 |  | 16.5 | Oms |
| 18b | 18b | 18b | Oms, C |
| 19.5a* | 19.5a* | 19.5a* | Oms, C |
| 19.5c |  | 19.5c | Oms |
| 25c |  | 25c | Oms |
| 28 | 28 |  | Oms, vsa‡ |
| 29a (OspD) |  |  | L, vsa§ |
| 29b | 29b |  | Oms, vsa‡ |
|  | 30 |  | Oms, vsa‖ |
| 35b |  |  | Oms, vsa§ |
| 39 |  | 39 | EF** |
| 40a |  |  | Oms, vsa§ |
| 40b |  |  | Oms, vsa§ |
| 40c¶ |  |  | Oms, vsa§ |

TABLE II-continued

Hydrophobic OMV Antigens Recognized by
Immunoblotting with Adsorbed Sera (Molecular Mass in kD)

| Passage 10 B31 | Passage 48 B31 | Avirulent ATCC B31 | Description |
|---|---|---|---|
| 42¶ | | | Oms, vsa§ |
| 70¶ | | | Oms, vsa§ |

L, lipoprotein; Oms, candidate outer membrane-spanning protein; C, protein common to all OMV preparations;
*for proteins with identical molecular masses, a designates the most acidic protein and the subsequent letters indicate proteins that are more basic;
‡vsa, virulent strain associated protein present in passage 10 and 48 OMV preparations (FIG. 4, A and B);
§vsa, virulent strain associated protein present only in passage 10 OMV preparation (FIG. 4 A);
∥vsa, virulent strain associated protein present only in passage 48 OMV preparation (FIG. 4 B);
¶not observed in passage 10 OMV 2-D gold stain (FIG. 3 A);
**endoflagellin (EF).

TABLE III

Recognition of Surface Exposed Proteins by IEM Using
Preimmune, Unadsorbed Immune, and Adsorbed Immune Sera

| Strain* | Basal (Preimmune) | Unadsorbed‡ (Immune) | Adsorbed‡ (Immune) |
|---|---|---|---|
| | gold particles per μm length§ | | |
| Passage 1 | 4.24 ± 2.69 (n = 11) | 167.8 ± 67.5∥ (n = 7) | 29.0 ± 11.4¶ (n = 8) |
| Passage 50 | 1.04 ± 0.47 (n = 5) | 90.0 ± 17.9∥ (n = 5) | 6.41 ± 4.23¶ (n = 10) |
| Avirulent ATCC | 0.39 ± 0.18 (n = 5) | 85.3 ± 35.3∥ (n = 5) | 1.58 ± 0.60¶ (n = 10) |

*Whole mount IEM was conducted with B. burgdorferi B31 passage 1, passage 50, and ATCC avirulent whole cells.
‡Unadsorbed immune serum was obtained from a rabbit infected with passage 4 B31 B. burgdorferi (26). Adsorbed serum was obtained by incubating the unadsorbed serum described above with ATCC avirulent B31 B. burgdorferi (see text for details).
§Values represent the average number of gold particles observed per μm length of the B. burgdorferi B31 analyzed ±SD. n refers to the number of fields of each sample analyzed under the electron microscope.
∥Wilcoxon ranked sum test indicated a significant difference (P = 0.039) when the unadsorbed immune serum was reacted with three strains tested.
¶Wilcoxon ranked sum test indicated a significant difference (P = 0.0001) when the adsorbed immune serum was reacted with three strains tested.

Example 2

Purification, Cloning and Nucleotide Sequence Determination of Oms28 Protein

This Example describes the FPLC purification of the 0.6 nS native porin protein from Borrelia burgdorferi that we have designated Oms28 for outer membrane-spanning protein 28. In addition, we have cloned and determined the nucleotide sequence of the oms28 gene. The 28 kDa Oms28 porin protein was overexpressed in Escherichia coli and was partially localized to the OM. Further, recombinant Oms28 (r-Oms28) demonstrated porin activity indicating that r-Oms28 was competent for export, assembly, and function in the E. coli OM and retained a conformation essential for porin activity. The results presented here confirm that Oms28 is an OM-spanning (Oms) protein, the first to be described for B. burgdorferi.

More particularly, Example 1 above reports that outer membrane vesicles of B. burgdorferi have a porin activity with a single channel conductance of 0.6 nS in 1 M KCl, using the black lipid bilayer assay. In this Example, using both non-denaturing isoelectric focusing and fast performance liquid chromatography (FPLC) separation after detergent solubilization, we found that the 0.6 nS porin activity resided in a 28 kDa protein, designated Oms28. The oms28 gene was cloned and its nucleotide sequence determined. The deduced amino acid sequence of Oms28 predicts a 257 amino acid precursor protein with a putative 24 amino acid leader peptidase I signal sequence. Processed Oms28 yields a mature protein with a predicted molecular mass of 25,363 daltons. The primary structure of Oms28 is compatible with a topological model featuring 10 amphipathic membrane spanning beta strands. When overexpressed in Escherichia coli, the Oms28 porin fractionated partially with the outer membrane and SDS-polyacrylamide gel purified Oms28 retained functional activity as demonstrated by an average single channel conductance of 1.1 nS in the planar lipid bilayer assay. These findings indicate that Oms28 is an outer membrane spanning protein of B. burgdorferi, the first to be described. As such, it is of potential relevance to the pathogenesis of Lyme borreliosis, and to the physiology of the spirochete.

MATERIALS AND METHODS

Bacterial Strains and Plasmids

Borrelia burgdorferi sensu stricto strain B31 was used in most of the experiments presented in this study and will be referred to as B. burgdorferi strain B31 in this Example. Virulent B. burgdorferi was originally isolated from infected mouse or rabbit tissue and cultivated in BSK II media at 34° C. as previously described {Skare, J. T., et al., J. Clin. Invest., 96:2380–2392 (1995)}. The term "passage" and the corresponding number refers to the number of times a B31 B. burgdorferi log phase culture was transferred to fresh BSK II media. The avirulent B. burgdorferi strain B31 (ATCC 35210) has been passaged several hundred times in vitro and is non-infectious for both mice and rabbits {Id.}. B. burgdorferi were enumerated using a calibrated ausJena Laboval 4 dark-field microscope.

Additional B. burgdorferi strains used include 297 {Steere, A. C., et al., N. Eng. J. Med., 308:733–740 (1983)}, ECM-86-NY {Schwan, T. G., et al., J. Clin. Microbiol., 26:8933–894 (1988)}, HB19 {Steere, A. C., et al., N. Eng. J. Med., 308:733–740 (1983)}, N40 {Barthold, S. W., et al., J. Infect. Dis., 157:842–846 (1988)}, and Sh-2–82 {Schwan, T. G., et al., J. Clin. Microbiol., 26:8933–894 (1988)}. All of these strains were isolated from infected rabbit tissue and cultivated in BSK-II media. European B. burgdorferi low-passage isolates 2872-2, 2872-3, 2872-6, and 3251-5, as well as Borrelia garinii, were kindly provided by Dr. Vittorio Sambri, University of Bologna, Italy. Borrelia hermsii serotype 7 (low-passage isolate) and serotype 33 (high-passage isolate) were both generously provided by Dr. Alan Barbour, University of Texas Health Science Center, San Antonio, Tex. T. pallidum was cultivated and obtained as previously described {Blanco, D. R., et al., J. Bacteriol., 176:6088–6099 (1994)}.

The Escherichia coli strain BL21 DE3 pLysE (Novagen, Inc., Madison, Wis.) was used to overproduce the B. burgdorferi Oms28 porin protein (see below). DH5α (Bethesda Research Laboratories, Inc., Gaithersburg, Md.) was used to subclone the oms28 gene into the plasmid pBluescript KS (Stratagene, Inc., San Diego, Calif.). The oms28 locus was overexpressed by using the plasmid pET17b (Novagen, Inc.), which contains the T7 promoter upstream from a multi-cloning site. All E. coli cultures were grown with aeration at 37° C. in Luria-Bertani (LB) liquid media or on LB agar at 37° C. {Maniatis, T., et al., Molecular Cloning:

*A Laboratory Manual*, Cold Spring Harbor Laboratory Press, Cold Spring Harbor, N.Y. (1992)}. Ampicillin and chloramphenicol were used at concentrations of 100 µg/ml and 25 µg/ml respectively.

Isolation of *B. burgdorferi* Genomic DNA

Linear and circular, supercoiled plasmid DNA from virulent *B. burgdorferi* strain B31 passage 2 was obtained and separated by cesium chloride density gradient centrifugation essentially as described elsewhere {Champion, C. I., et al., *Infect. Immun.*, 62:2653–2661 (1994)}. *B. burgdorferi* chromosomal DNA was purified essentially as previously described for *T. pallidum* {Blanco, D. R., et al., *Mol. Microbiol.*, 5:2405–2425 (1991)}.

Isolation of Outer Membrane Vesicles (OMV) Derived from *B. burgdorferi*

OMV were obtained as previously described {Skare, J. T., et al., *J. Clin. Invest.*, 96:2380–2392 (1995)}.

SDS-polyacrylamide Gel Electrophoresis (SDS-PAGE) and Immunoblotting

Protein samples were resolved using discontinuous SDS-PAGE according to the method outlined by Laemmli {Laemmli, U. K., *Nature* (London), 227:680–685 (1970)}. Proteins that were analyzed by two dimensional (2D) gel electrophoresis using non-denaturing isoelectric focusing gel electrophoresis in the first dimension and SDS-PAGE in the second dimension were incubated in ND-IEF sample buffer composed of 62.5 mM Tris HCl pH 6.8, 0.1% SDS, 10% glycerol, 0.01% bromophenol blue and were incubated at room temperature (22° C.) for 30 minutes. All other protein samples were incubated in conventional SDS-PAGE sample buffer {Id.}.

Western immunoblotting was conducted as previously described {Skare, J. T., et al., *J. Clin. Invest.*, 96:2380–2392 (1995)}. Rabbit serum specific for Oms28 (described below) was diluted 1:5000, and rabbit serum specific for the *E. coli* proteins OmpA (kindly provided by Dr. W. Wickner, Dartmouth College) and $F_1F_o$ ATPase subunit c (kindly provided by Drs. J. Hermolin and R. Filingame, University of Wisconsin, Madison, Wis.) were both diluted 1:10,000 for Western blot analyses. Donkey anti-rabbit immunoglobulin conjugated to horseradish peroxidase was diluted 1:5000 and used as the secondary antibody (Amersham Corp.). Antigen-antibody complexes were detected using the enhanced chemiluminescence (ECL) system of Amersham (Arlington Heights, Ill.) as previously described {Skare, J. T., et al., *J. Clin. Invest.*, 96:2380–2392 (1995)}.

Identification and Polyacrylamide Gel Purification of Native Oms28

Frozen aliquots of phosphate buffered saline pH 7.4 (PBS) washed *B. burgdorferi* B31 passage 2 corresponding to $3 \times 10^9$ whole cells or OMV {Skare, J. T., et al., *J. Clin. Invest.*, 96:2380–2392 (1995)} derived from $5 \times 10^9$ *B. burgdorferi* B31 passage 7, were incubated for 2 hours at 4° C. in 100 µl PBS, 1% Triton X-100 (TX-100, CalBiochem, San Diego, Calif.). After 2 hours, 100 µl of sterile water was added and the samples were rocked at 22° C. for 30 minutes. The samples were then diluted further with 200 µl of sterile water and rocked at 22° C. for an additional 20 minutes. The protoplasmic cylinders or insoluble membrane material were removed by two successive centrifugation steps at 13,000×g. The supernatant was then concentrated to approximately 40 µl. The zwitterionic detergent CHAPS {3-[(3-cholamidopropyl)-dimethyl-ammonio]-1-propanesulfonate, CalBiochem} was then added to a final concentration of 2% (wt./vol.). Additionally, ampholytes with a pH range of 3 to 10 and 5 to 7 (Bio-Rad, Richmond, Calif.) were added to a final concentration of 0.4% and 2%, respectively, along with glycerol to a final concentration of 10%. The protein sample was then resolved by non-denaturing isoelectric focusing (ND-IEF) polyacrylamide gel electrophoresis as described elsewhere {Blanco, D. R., et al., *J. Bacteriol.*, 177:3556–3562 (1995)}. After electrophoresis, the tube gel (0.2 cm by 12 cm) was cut into 24 equal 0.5 cm pieces, crushed with a sterile pestle in 0.1 M NaCl, 0.1% TX-100, and assayed in the planar lipid bilayer assay as described below. After the location of the porin activity in the first dimension gel was determined (see below), this region was further analyzed using SDS-polyacrylamide gel electrophoresis in the second dimension (2D SDS-PAGE). Two identical uncut tube gels were incubated in 0.1 M Tris HCl pH 6.8, 0.1% SDS, 100% glycerol, 0.05% bromophenol blue for 30 minutes at 22° C. and then separated in the second dimension by 0.1% SDS-10% PAGE. One of the SDS-polyacrylamide gels (SDS-PAG) was stained with Coomassie brilliant blue and destained {Ausubel, F., et al., *Current Protocols In Molecular Biology*, ed. John Wiley and Sons, New York (1988)}. A 28 kDa protein common to the 2D profiles from whole cells and the OMV preparations was cut out of an unfixed and unstained SDS-polyacrylamide gel (SDS-PAG) and crushed with a sterile pestle in a 200–300 µl 0.1 NaCl, 0.1% TX-100 suspension. This sample was then assayed for porin activity using the planar lipid membrane bilayer assay as described below.

Fast Performance Liquid Chromatography (FPLC) Purification of Oms28

OMV derived from $5 \times 10^{10}$ *B. burgdorferi* B31 passage 2 or B31 avirulent ATCC were solubilized in 50 mM Tris HCl pH 8.0, 1% hydrogenated Triton X-100 (hTX-100; CalBiochem Corp., San Diego, Calif.). Residual particulate material was removed by two successive 13,000×g centrifugations. The supernatant was kept on ice and the protein samples, ranging from 1 to 5 mg, were separated by FPLC using the Pharmacia LCC-500 Model Controller (Pharmacia LKB Biotechnology Inc., Piscataway, N.J.). The proteins were applied to a 1 ml Mono Q column and, when the $OD_{280}$ reached baseline, were eluted off the anion exchanger in a 30 ml volume using a 0 to 600 mM NaCl linear gradient buffered in 50 mM Tris HCl pH 8.0, 0.5% hTX-100. All fractions were collected in 0.5 ml volumes. The resulting fractions were screened for the presence of Oms28 by spotting 2 µl per fraction onto nitrocellulose followed by an incubation with Oms28-specific antiserum and ECL immunoblotting. Fractions containing Oms28 were pooled, repurified by FPLC with the 1 ml Mono Q column as described above. Fractions containing Oms28 were supplemented with SDS to a final concentration of 0.1%, glycerol to a final concentration of 10%, and the pH adjusted to 6.8. The sample was resolved by SDS-PAGE, and the 28 kDa region excised from the gel. Oms28 was eluted in 0.1 M NaCl, 0.5% hTX-100 and tested for porin activity as described below or rerun on SDS-PAGE, immunoblotted to a polyvinylidene fluoride (PVDF; Millipore, Bedford, Mass.), and stained with either colloidal gold (AuroDye forte, Amersham Corp., Arlington Heights, Ill.) or amido black to determine the purity of the Oms28 porin.

Planar Membrane Assays of Purified Oms28

Porin activity was assessed essentially as described {Skare, J. T., et al., *J. Clin. Invest.*, 96:2380–2392 (1995)}. FPLC and gel purified native Oms28 was diluted 1 to 10,000 or 1 to 30,000 prior to addition to the bilayer. In contrast, gel purified r-Oms28 was diluted 1 to 500 or 1 to 2000 prior to the addition to the bilayer.

Amino Acid Sequencing of Oms28

TX-100 detergent solubilizations, non-denaturing IEF gel electrophoresis, and SDS-PAGE (i.e., non-denaturing 2D analysis) were conducted essentially as described above for the gel purification of native Oms28 except that *B. burgdorferi* B31 passage 13 was used as the source of Oms28. After non-denaturing IEF gel electrophoresis and SDS-PAGE, the TX-100 solubilized proteins were immunoblotted to nitrocellulose (Scheicher and Schuell, Keene, N.H.) as described {Towbin, H., et al., *Proc. Natl. Acad. Sci. USA*, 76:4350–4354 (1979)} and stained with 1% amido black. The blot was destained and the spot corresponding to the 28 kDa Oms28 porin (approximately 10 $\mu$g) was excised from the membrane, placed in sterile water, and was frozen at −20° C. The Oms28 protein was then partially digested with trypsin and processed for internal amino acid sequencing as described elsewhere {Blanco, D. R., et al., *J. Bacteriol.*, 177:3556–3562 (1995)}.

Cloning and Sequencing of the Oms28 Gene

Southern blot analysis was performed as described by Maniatis, et al. {Maniatis, T., et al., *Molecular Cloning: A Laboratory Manual*, Cold Spring Harbor Laboratory Press, Cold Spring Harbor, N.Y. (1982)} utilizing end-labeled [Y-$^{32}$P]ATP (Amersham Corp., Arlington Heights, Ill.) mixed oligonucleotides 28A2 and 28B1 which correspond to peptides A and B respectively (see Results section, below). Briefly, *B. burgdorferi* chromosomal, supercoiled plasmid, and linear plasmid DNA was digested with various restriction enzymes and separated by agarose gel electrophoresis. Following hybridization and autoradiography, two linear plasmid DNA HindIII restriction fragments of 1.6 kb and 3.0 kb were identified by probes 28A2 and 28B1, respectively. Linear plasmid DNA digested with HindIII was separated by agarose gel electrophoresis and the 1.6 kb and 3.0 kb regions were excised and purified separately using Geneclean II (Bio 101, La Jolla, Calif.) and cloned into the HindIII site of pBluescript KS previously treated with shrimp alkaline phosphatase (United States Biochemical, Cleveland, Ohio.). Following transformation into DH5α, clones containing the 1.6 kb and 3.0 kb inserts were identified separately by colony hybridization using probes 28A2 and 28B1. Positive clones were sequenced using the dideoxynucleotide chain termination method previously described {Sanger, et al., *Proc. Natl. Acad. Sci. USA*, 74:5463–5467 (1977)} using [α-$^{35}$S]dATP (Amersham Corp., Arlington Heights, Ill.).

DNA and Protein Sequence Analysis

The nucleotide sequence of oms28 was analyzed using the DNA Strider version 1.0 program {Marck, C., et al., *Nucleic Acids Res.*, 16:1829–1836 (1988)}. Homology searches with either full length Oms28 or tryptic peptides derived from Oms28 were conducted using a BLASTP search of the National Center for Biotechnology Information (NCBI) database {Altschul, S. F., et al., *J. Mol. Biol.*, 215:403–410 (1990)}. The Oms28 hydrophobic beta moment plot was deciphered as previously described {Blanco, D. R., et al., *J. Bacteriol.*, 177:3556–3562 (1995)}.

Oligonucleotides

Oligonucleotides were synthesized using the Applied Biosystem model 470B automated DNA synthesizer and OPC chromatography as previously described {Blanco, D. R., et al., *J. Bacteriol.*, 177:3556–3562 (1995)}.

Polymerase Chain Reaction (PCR)

PCR was conducted using the GeneAmp kit containing AmpliTaq (Perkin-Elmer Cetus, Foster City, Calif.) and the Programmable Thermal Controller PTC-100 (M. J. Research, Inc., Watertown, Mass.) according to the manufacturers specifications. Briefly, 50 $\mu$l PCR reactions were incubated with 10 or 100 ng of either chromosomal, linear plasmid, or supercoiled, circular plasmid DNA as template with 1 $\mu$M primers, 10 mM Tris HCl pH 8.3, 50 mM KCl, 2 mM MgCl$_2$, 0.001% (wt./vol.) gelatin, 200 $\mu$M of each deoxynucleotide triphosphate, and 1.25 U AmpliTaq. After a 50 $\mu$l overlay with mineral oil, the PCR reaction mixtures were incubated for 35 cycles, starting with a denaturation step at 94° C. for 2 minutes followed by 94° C. for 1 minute, 45° C. for 1 minute, 72°C. for 2 minutes, and a final extension step at 72° C. for 6 minutes. The amplimers were resolved by agarose gel electrophoresis buffered in 40 mM Tris acetate pH 8.7, 1 mM EDTA and purified with Geneclean II (Bio 101, La Jolla, Calif.).

OMV Washes

OMV preparations derived from 1.25×10$^9$ *B. burgdorferi* strain B31 passage 3 (in 10 $\mu$l volumes) were diluted to 100 $\mu$l with the following salt solutions: PBS pH 7.4; 1 M NaCl; 0.1 M Na$_2$CO$_3$ pH 11.0. A control sample was presolubilized with 1% Triton X-100 and then incubated with 1 M NaCl. The samples were incubated on ice for 5 minutes, diluted to 1 ml with PBS pH 7.4, and pelleted at 40,000 g for 1 hour at 4° C. The supernatant was removed and the protein concentrated by precipitation with trichloroacetic acid (TCA). The pelleted and supernatant material were resuspended in Laemmli sample buffer and the proteins resolved by SDS-polyacrylamide gel electrophoresis {Laemmli, U. K., *Nature* (London), 227:680–685 (1970)}. The proteins were then electroblotted to a PVDF membrane and immunoblotted with antiserum specific for Oms28.

Triton X-114 Phase Extraction

1×10$^9$ *B. burgdorferi* B31 passage 2 whole cells were subjected to Triton X-114 phase partitioning as previously described {Skare, J. T., et al., *J. Clin. Invest.*, 96:2380–2392 (1995)}, analyzed by SDS-PAGE, and immunoblotted using Oms28-specific antiserum as described above.

Fractionation and Localization of Recombinant Oms28 in *E. coli*

The native oms28 gene was cloned into pET17b vector (Novagen, Inc.) using PCR primers with restriction enzyme sites engineered at their ends. The primer oms28N5' (5' GGAATTCCAT<u>ATG</u>ACTAAAATATTTAG TAAT 3'; SEQ ID NO:3) contains a NdeI site (italicized) that encodes the codon for the initiating methionine (underlined) of oms28 directly at the 5' end. A primer corresponding to the carboxy terminus, designated C (5' CGCGGATCCGAATTC <u>CTA</u>TCTCATGTATMAGAAAT 3'; SEQ ID NO:4), contains an EcoRI site (italicized) immediately 3' from the stop codon of oms28 (underlined; corresponds to the stop codon sequence from the non-coding strand). PCR, using 10 ng of *B. burgdorferi* B31 passage 2 linear plasmid DNA as template and the primers oms28N5' and oms28E3', yielded an approximately 800 bp fragment that was then digested with NdeI and EcoRI and purified with Geneclean II (Bio 101). The plasmid pET17b was digested with NdeI and EcoRI, purified using Geneclean II, and incubated with shrimp alkaline phosphatase (United States Biochemical, Cleveland, Ohio.) according to the manufacturers instructions. The PCR amplimer and pET17b were ligated together and transformed into BL21 DE3 pLysE. Positive clones were grown in 50 ml of LB broth containing ampicillin and chloramphenicol to an OD$_{600}$ of 0.5. Isopropylthio-β-D-galactoside (IPTG) was then added to a final concentration of 1 mM and incubated at 37° C. for 1 hour. After 1 hour, rifampicin was added to a final concentration of 150 $\mu$g/ml and the incubation at 37° C. was continued an additional 2 hours. The OD$_{600}$ of the culture was determined and the cells harvested by centrifugation at 8000×g for 10 minutes. The cells were then resuspended in PBS such that the density was between 5–10 $OD_{600}$ equivalents per ml and were frozen at −20° C. overnight. The sample was thawed the next day and the cells lysed by a French pressure cell set at 600–1000 lb./in.$^2$. Unlysed cells were pelleted at 4000×g for 10 minutes. The supernatant was transferred to a new tube and centrifuged again at 10,000×g for 1 minute. The supernatant was then recentrifuged at 40,000×g for 30 minutes at 4° C. to pellet total membrane. The supernatant represented the soluble protein fraction. Pelleted membrane was resuspended in PBS, 2% TX-100 and rocked at 4° C. for 1 hour, then at room temperature for 1 hour. Outer membrane (OM) was pelleted by centrifugation at 40,000×g for 30 minutes. The supernatant was saved as the TX-100 soluble inner membrane (IM) fraction. IM protein was concentrated by TCA precipitation. The OM pellet was washed with PBS and recentrifuged at 40,000×g for 30 minutes at 4° C. The final OM pellet was resuspended in PBS such that the OM concentration is equivalent to 1 $OD_{600}$(ml) per μl. Fractions were then analyzed by SDS-PAGE and either stained with Coomassie brilliant blue or immunoblotted using antiserum specific for Oms28 that was adsorbed with BL21 DE3 pLysE, pET17b as previously described {Gruber, A., et al., BioTechniques, 19:28–30 (1995)}.

Antisera

Antiserum specific for Oms28 was obtained by overproducing Oms28 using the 17 regulated plasmid vector pET17b (Novagen, Inc.) as follows. Oligonucleotides specific for the sequence corresponding to the amino (N) terminus and carboxy (C) terminus of mature Oms28 were synthesized with BamHI and EcoRI restriction sites at the 5' ends respectively. The N oligonucleotide (5' CGCGGATCCAGATTCTAACAATGCMATATT 3'; SEQ. ID NO:5: BamHI site is italicized) and oms28E3' oligonucleotide (5' CGCGGATCCGAATTCCTATCTCATGTATAAAGMAT 3'; SEQ ID NO:4 EcoRI site is italicized) were combined with 10 ng of linear plasmid DNA and subjected to PCR as described above. The amplified DNA fragment, approximately 700 base pairs, was digested with EcoRI and BamHI, and purified using Geneclean (Bio 101, La Jolla, Calif.). Separately, plasmid pET17b was digested with BamHI and EcoRI, purified by Geneclean, and incubated with shrimp alkaline phosphatase (United States Biochemical, Cleveland, Ohio.). The phosphatased vector and insert were ligated using standard molecular biology techniques and the resulting construct transformed into E. coli BL21 DE3 pLysE. The resulting construct encoded a fusion protein containing 22 residues from the T7 gene 10 protein fused to the processed or mature Oms28 protein. Overproduction of the processed Oms28 was performed according to the manufacturer's instructions (Novagen, Inc.) and the recombinant Oms28 protein purified using FPLC as described above for native Oms28. Fractions containing an induced 28 kDa protein were further purified by preparative SDS-polyacrylamide gel electrophoresis and visualized by staining in 0.05% Coomassie brilliant blue in distilled $H_2O$ for 10 minutes. Protein corresponding to 100 μg was combined with incomplete Freund's adjuvant and inoculated subcutaneously and intramuscularly into a New Zealand white rabbit. Boosting was conducted with equivalent amounts of recombinant Oms28 in incomplete Freund's adjuvant 4 weeks post inoculation and serum was obtained 17 days post-boost. Serum used for analysis with E. coli samples was preadsorbed with lysates from BL21 DE3 pLysE prepared as previously described {Gruber, A., et al., BioTechniques, 19:28–30 (1995)}.

RESULTS

Identification of a Porin Activity Associated with the OM of B. burgdorferi

Figure 8A:
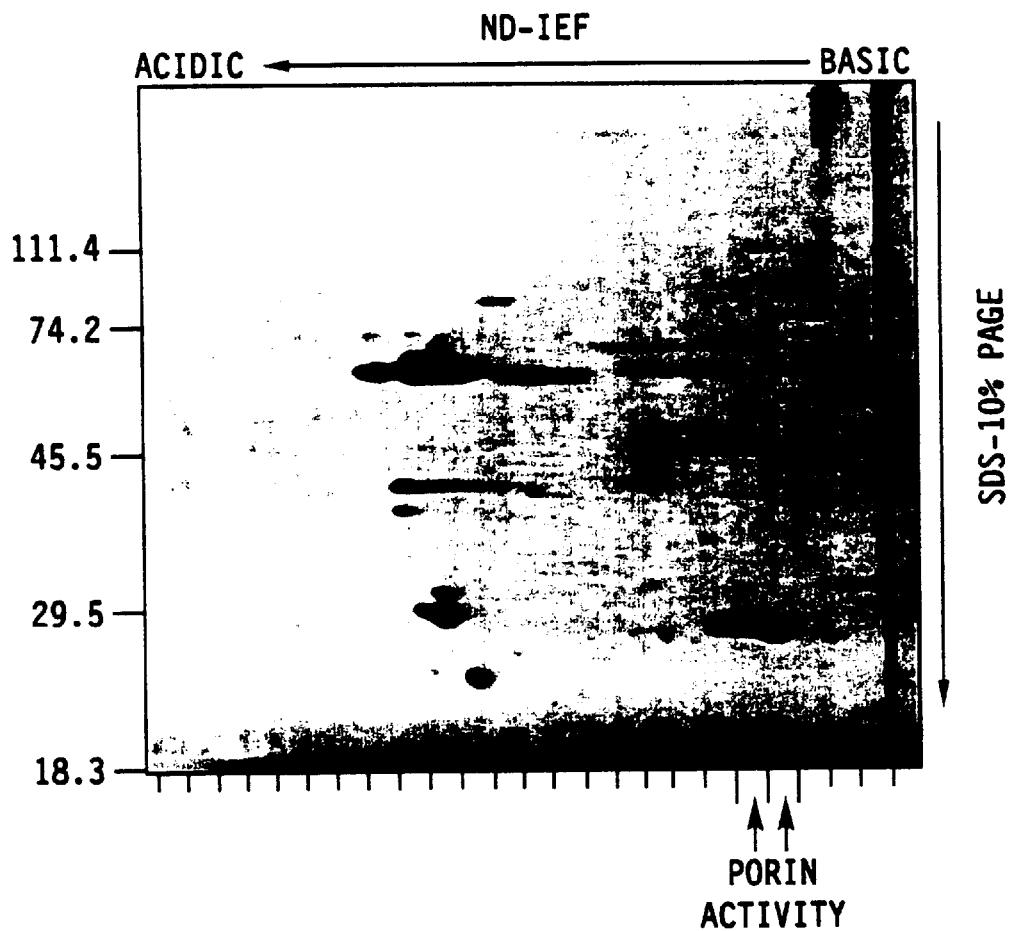
Figure 8B:

To determine which OM protein had the 0.6 nS porin activity we had previously observed in Example 1, in our OMV preparation {Skare, J. T., et al., J. Clin. Invest., 96:2380–2392 (1995)}, whole B. burgdorferi strain B31 and OMV derived from B. burgdorferi were incubated in 1% TX-100 and the solubilized proteins separated by non-denaturing isoelectric focusing (ND-IEF) gel electrophoresis. After the IEF gel was cut into separate pieces, the protein eluted and assayed in the planar lipid bilayer assay system, a single channel conductance of 0.6 nS was observed in a fraction containing several proteins of which a molecule with an apparent molecular mass of 28 kDa was the most abundant (FIG. 8A). A previously described "flickering" activity {Id.} was observed for the 0.6 nS porin suggesting that the channel was not in a native conformation (FIG. 8B). Similar ND-IEF analyses were conducted with OMV derived from both virulent B. burgdorferi B31 passage 7 and avirulent B. burgdorferi B31 ATCC and a similar 0.6 nS conductance was observed for the OMV solubilized material (data not shown). Comparison of the solubilized whole cells and the solubilized OMV material indicated that the 28 kDa species was the only protein in the ND-IEF eluted sample that was common between these different preparations suggesting that the 28 kDa protein was the 0.6 nS porin.

FPLC Purification of the Native Oms28 Porin Protein

Figure 9D:
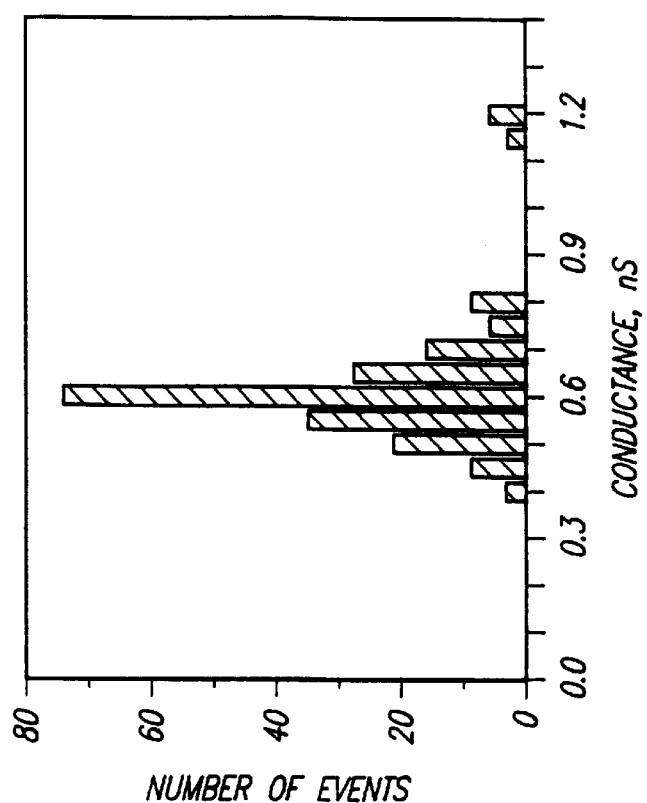
Figure 9C:
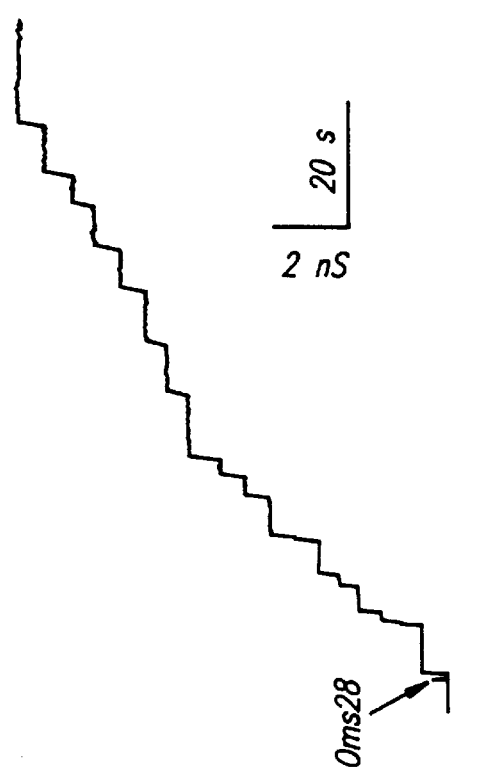

To determine whether the 28 kDa protein was the 0.6 nS porin, we separated detergent solubilized OMV proteins by FPLC. A 28 kDa protein was observed in fractions that eluted off the Mono Q column at a concentration of NaCl ranging between 80 to 90 mM. These fractions were pooled and separated again by FPLC and the 80 to 90 mM NaCl eluates tested for porin activity. The amount of Oms28 obtained from OMV derived from $10^{10}$ virulent or avirulent B. burgdorferi was approximately 2 μg or 0.5 μg respectively, implying that oms28 is expressed preferentially in the virulent isolate (data not shown). The FPLC fractions containing Oms28 were contaminated with the B. burgdorferi large channel {Skare, J. T., et al., J. Clin. Invest., 96:2380–2392 (1995)} which has an approximate 25- to 50-fold greater specific activity than the Oms28 specific activity in these fractions. Therefore, dilutions that eliminated the contaminating large channel activity yielded no detectable 0.6 nS porin activity since the amount of functional Oms28 remaining were below the threshold of detection. To circumvent this problem, the fractions containing Oms28 were separated by SDS-PAGE, the 28 kDa region excised, the protein eluted from the gel and tested for purity and porin activity (FIG. 9). A 0.6 nS channel was observed in the gel eluted material corresponding to the 28 kDa region of the SDS-PAG. The large number of channel insertions into the bilayer (n=181; FIG. 9D) and the absence of the flickering (FIG. 9C) suggests that the 28-kDa protein was in a stable conformation. Porin activity was observed at concentrations of Oms28 ranging from 0.13 to 0.4 ng/ml which is approximately 5 to 10-fold more dilute than that observed for other porin protein in conventional lipid bilayer assays {Trias, J., et al., J. Biol. Chem., 268:6234–6240 (1993); Hancock, R. E. W., Bacterial Outer Membranes As Model Systems, John Wiley and Sons, New York, N.Y., pp.187–225 (1986)}. The 28-kDa porin was designated Oms28 for outer membrane-spanning 28-kDa protein.

In separate experiments, an SDS-PAG lane was cut into 12 separate pieces representing the entire vertical length of the gel, the proteins eluted and tested separately for porin activity (data not shown). Greater than 90% of the 0.6 nS activity was observed in the sample containing the 27- to 30-kDa region of the gel; the remaining 10% of the 0.6 nS activity was evenly distributed in samples in the molecular mass range between 30 to 100 kDa implying that the Oms28 porin formed aggregates that resolve at various molecular masses. No large channel activity was observed in any of the fractions tested indicating that this porin protein is not functional in the presence of 0.1% SDS (data not shown).

Cloning and Nucleotide Sequence of Oms28

In order to clone the gene encoding the Oms28 porin protein, approximately 15 μg of the 28-kDa protein spot that retained the 0.6 nS porin activity was submitted for amino acid sequencing. The Oms28 porin was digested with trypsin and the resulting peptides separated by reverse-phase high performance liquid chromatography (RP-HPLC) as previously described {Tempst, P., et al., in *Methods a companion to Meth. in. Enz.*, 6:248–261 (1994); Blanco, D. R., et al., *J. Bacteriol.*, 177:3556–3562 (1995)}. The sequence of five peptides was obtained. Two peptides, designated A and B, were used to create degenerate oligonucleotides; there sequence is as follows: peptide A; DS NNANILKPQSNVLEHSDQKDNK (SEQ ID NO:2; amino acids 25–48); peptide B; AL DETVQEAQK (SEQ ID NO:2; amino acids 197–207). The underlined amino acids correspond to the residues utilized to design the degenerate oligonucleotides. These oligonucleotides, designated 28A2 (with a 192-fold degeneracy from peptide A) and 28B1 (with a 128-fold degeneracy from peptide B), were then used as probes against HindIII digested *B. burgdorferi* B31 passsage 2 chromosomal, linear plasmid, and circular, supercoiled plasmid DNA to identify the gene encoding Oms28 (data not shown). The 28A2 and 28B1 oligonucleotides recognized a 1.6 kb and 3 kb fragment in the HindIII digested linear plasmid DNA, respectively. This suggested that a single HindIII restriction site split the oms28 gene into two fragments and that the degenerate oligonucleotides recognized sequences both upstream (5') and downstream (3') of the HindIII site. These two fragments were cloned into pBluescript as two stable constructs and sequenced using both the Universal and Reverse oligonucleotides as primers (Bethesda Research Laboratories, Gaithersburg, Md.). Open reading frames were identified in the clones that confirmed both the presence of a single HindIII site in oms28 and the amino acid sequence of the A and B tryptic peptides derived from Oms28. The oms28 gene was sequenced to completion by primer walking on both strands using the dideoxynucleotide method of Sanger {Sanger, et al., *Proc. Natl. Acad. Sci. USA*, 74:5463–5467 (1977)}.

Sequence Analysis

The nucleotide sequence of oms28 revealed an open reading frame of 771 base pairs encoding for a 257 amino acid protein with a calculated molecular weight of 28,002 daltons (FIG. 10). Upstream sequences resembling a conventional gram negative −35 (TTTAAA; SEQ ID NO:1, nucleotides 39–48) and −10 (TATGTT; SEQ ID NO:1, nucleotides 57–62) $\sigma^{70}$ promoter consensus as well as a putative ribosome binding site (AAGGAG; SEQ ID NO:1, nucleotides 101–106) were identified (FIG. 10). A putative rho-independent transcriptional termination sequences was also identified. The predicted amino terminal end of the full-length Oms28 protein contains a 24 amino acid leader peptide sequence typical of exported proteins with a basic residue followed by a hydrophobic core (amino acids 4 to 20) and a potential leader peptidase I cleavage site {Von Heijne, G., *J. Mol. Biol.*, 184:99–105 (1985)}, Val-Phe-Ala (SEQ ID NO:2, amino acids 22–24). The cleavage of the 24 amino acid leader sequence would yield a mature Oms28 protein composed of 233 amino acids with a molecular mass of 25,363 daltons. Comparison of the deduced amino acid sequence of Oms28 with the tryptic peptide A sequence (see above) derived from Oms28 indicated that the amino terminus of peptide A was preceded by an alanine residue instead of an arginine or lysine residue required for cleavage by trypsin (see above and FIG. 10). This indicates that peptide A represents the amino terminal end of the cleaved, mature Oms28 protein.

No proteins homologous to Oms28 were identified from a search of the NCBI database using the full-length amino acid sequence of Oms28. Hydrophobic moment plot analysis was used to predict a topological model for Oms28 (data not shown). The model, as shown in FIG. 11, suggests that Oms28 contains 10 beta pleated sheets structures capable of spanning an outer membrane with large surface exposed loops and short periplasmic loops. The membrane spanning domains contain alternating hydrophobic and hydrophilic residues consistent with the organization observed for several gram negative outer membrane porin proteins, including those whose crystal structures have been determined {Cowan, S. W., et al., *Nature* (London), 358:727–733 (1992)}. These observations, coupled with the porin activity described above, imply that Oms28 is a *B. burgdorferi* outer membrane-spanning protein, the first to be functionally characterized. Additionally, oms28 is the first gene to be cloned and sequenced that encodes a functional Oms protein.

Outer Membrane Localization of Oms28 in *Borrelia burgdorferi*

To determine whether native Oms28 was an Oms protein or a peripherally associated periplasmic protein in our OMV preparations, we utilized harsh salt solutions which are known to release soluble proteins yet retain integral membrane proteins {Fujiki, Y., et al., *J. Cell Biol.*, 93:97–102 (1982); Fujiki, Y., et al., *J. Cell Biol.*, 93:103–110 (1982)}. As shown in FIG. 12, Oms28 remained exclusively affiliated with the pelleted material, as detected with recombinant Oms28 antisera and ECL immunoblotting, after a short incubations in either 1 M NaCl or 0.1 M $Na_2CO_3$ pH 11 and subsequent centrifugation except when the OMV was presolubilized with 1% Triton X-100. Under identical conditions, contaminating levels of BSA fractionated into the supernatant fractions (data not shown). These results suggest that Oms28 is an integral membrane protein, consistent with its porin activity.

*B. burgdorferi* whole cell preparations were subjected to Triton X-114 phase partitioning to determine if Oms28 was a detergent phase protein as one would predict for an Oms protein. Surprisingly, Western immunoblot analysis showed that Oms28 partitioned exclusively into the aqueous phase (FIG. 13B) suggesting that Oms28 was no longer folded into a membrane-spanning conformation and therefore separated anomalously as a soluble protein. In contrast to samples solubilized with Triton X-100, OMV solubilized with Triton X-114 never demonstrated any 0.6 nS porin activity, even following FPLC purification of the aqueous phase proteins, consistent with the observation that Oms28 lacks the conformation essential for activity after exposure to Triton X-114 phase partitioning.

Outer Membrane Localization and Functional Activity of Recombinant Oms28 in *Escherichia Coli*

Figure 19A:
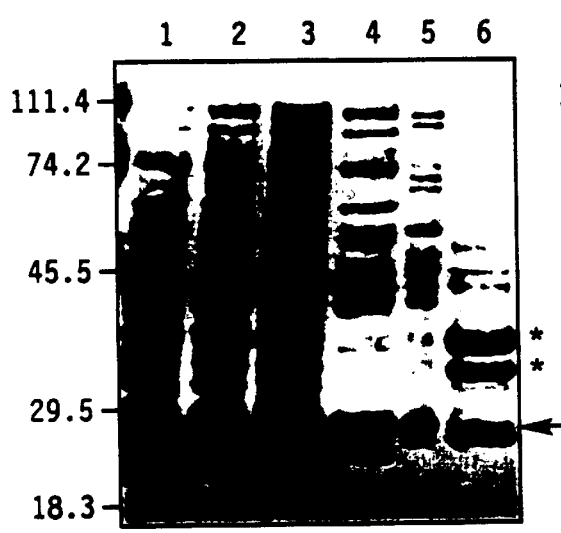
Figure 19B:
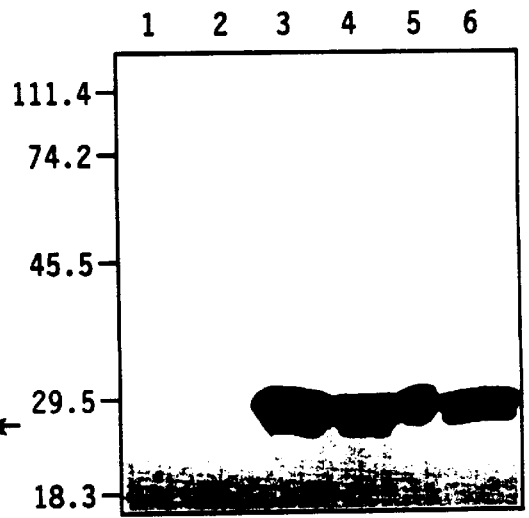

Recombinant Oms28 (r-Oms28) was overexpressed in *Escherichia coli* and the cells fractionated to determine whether this spirochetal porin protein would be competent for export, assemble in the OM of *E. coli*, and exhibit porin activity in a heterologous system. When oms28 was overexpressed, r-Oms28 was distributed in the soluble, inner membrane (IM) and outer membrane (OM) fractions with the majority in the soluble fraction (FIG. 19A, lanes 4 and 6, respectively). The soluble form of r-Oms28 observed is located either within the cytoplasm or periplasm although it would appear, based on its apparent molecular mass, to be processed (e.g., cleaved by E. coli leader peptidase I) which would suggest that it is an exported and therefore located within the periplasm. Approximately 3 μg of r-Oms28 was observed in OM derived from $10^9$ induced E. coli cells (or approximately 1.5 $OD_{600}$[ml] of cells) expressing oms28. Residual r-Oms28 was detected in the IM fraction by Coomassie brilliant blue staining (FIG. 19A, lane 5) and approximately 20% was observed in the IM fraction following ECL immunoblotting with specific antisera generated against r-Oms28 (FIG. 19B). This suggests that either the IM fraction was contaminated with OM or residual steady-state levels of r-Oms28 were being processed across the IM at the time of cell harvesting.

Overproduced r-Oms28 fractionated to the OM in E. coli and, when the sample was not heated or exposed to reducing agents, formed, in addition to an induced 28-kDa species, an oligomeric structure of approximately 80 kDa that reacted with antiserum specific for Oms28 as shown in FIG. 14. Neither the 28 or 80 kDa forms of r-Oms28 were observed in OM derived from induced E. coli cells harboring the vector plasmid alone indicating that both of these proteins originated from the induction of oms28. Since porin proteins have an oligomeric stoichiometry {Cowan, S. W., et al., Nature (London), 358:727–733 (1992)}, including the spirochetal porin proteins OmpL1 {Shang, E. S., et al., Infect. Immun., 63:3174–3181 (1995)} and Tromp1 {Blanco, D. R., et al., [Manuscript in preparation]}, it is tempting to speculate that r-Oms28 has a similar organization.

To determine if r-Oms28 retained porin activity we gel eluted OM material derived from the vector only control and the Oms28 expressing E. coli. The unheated samples were resolved by SDS-PAGE (as described in the methods section) and the region of the gel corresponding to the molecular mass of 28 kDa of both the control and r-Oms28-containing OM were tested for porin activity. Whereas the control showed no porin activity for the 28 kDa region (data not shown), the r-Oms28 sample had a 1.1 nS channel forming activity similar to that observed at low levels for native Oms28 (compare FIG. 9D and FIG. 16B). The amounts of r-Oms28 required for detectable porin activity were between 10–15 ng/ml or approximately 25- to 75-fold less than the amounts used to demonstrate porin activity for native Oms28 (FIGS. 9C and 9D). The "flickering" observed in the conductance profile shown (FIG. 15A) indicated that the r-Oms28 protein was not in a stable conformation consistent with its difference in intrinsic conductance. However, the number of insertional events observed, 54 (FIG. 15B), and the similarity in conductance relative to native Oms28 further confirmed that Oms28 was a porin protein observed in our previously OMV preparation {Skare, et al., J. Clin. Invest., 96:2380–2392 (1995)}.

Presence of Oms28 in Other American and European B. burgdorferi Isolates

To determine whether Oms28 was present in other virulent B. burgdorferi isolates, we probed an immunoblot containing protein extracts from either passage 1 American strains or low-passage European isolates (FIG. 16). Additionally, we examined if a protein similar to Oms28 was present in a related Borrelia, Borrelia garinii, and in the etiologic agents of relapsing fever and syphilis, Borrelia hermsii and T. pallidum, respectively (FIG. 16). All American and European isolates tested contained an Oms28-like protein although N40 and the European strain 2872-3 synthesized less Oms28 relative to the other B. burgdorferi isolates. A doublet was observed in strain 2872-3 that was not apparent in any other B. burgdorferi isolate tested. No Oms28 protein was observed in the other spirochetal pathogens B. garinii, B. hermsii, or T. pallidum suggesting that Oms28 is a protein specific to B. burgdorferi.

Example 3

Purification if Oms45

In this Example, we have identified another porin protein from the detergent phase of Triton X-114 extracted organisms and demonstrated an average single channel conductance of 0.22 nS. We have purified a 45 kDa protein which corresponds to the observed porin activity and have designated it as Oms45.

METHODS

Bacterial Strains

Avirulent B. burgdorferi strain B31 (American Type Culture Collection [ATCC] 35210, Rockville, Md.) has been passaged several hundred times in vitro and was grown in BSK II media supplemented with 6% normal rabbit serum as previously described {Barbour, A. G., Yale J. Biol. Med., 57:521–525 (1984)}.

Triton X-114 Phase Partitioning of B. burgdorferi

Triton X-114 (TX-114) (CalBiochem) extractions were performed as previously described {Cunningham, T. M., et al., J. Bacteriol., 170:5789–5796 (1988)}. Briefly, $3\times10^{10}$ organisms at a concentration of $2\times10^8$ organisms/ml were centrifuged at 6,000×g for 20 min. at room temperature. The pellet was washed once with 50 mM Tris-HCl pH 8.0 and centrifuged again as described above. The supernatant was discarded and the pellet was resuspended in 9 ml of cold 50 mM Tris-HCl pH 8.0 to a final concentration of $3\times10^9$ organisms/ml. To this suspension was added 1 ml of 10% TX-114 to a final detergent concentration of 1%. The suspension was incubated on a rocker at 4° C. for 2 hr. and the insoluble material removed by two successive centrifugations at 15,000×g at 4° C. for 15 min. The supernatant was incubated at 37° C. for 10 min. and the phases partitioned by centrifugation at 10,000×g for 10 min at room temperature. The aqueous phase was discarded and the detergent phase was re-extracted three times with cold 50 mM Tris-HCl pH 8.0 as described above. The final detergent phase was resuspended to 10 ml of 50 mM Tris-HCl pH 8.0 containing 0.5% hydrogenated Triton X-100 (hTX-100) (CalBiochem).

Separation of TX-114 Proteins by Fast Performance Liquid Chromatography (FPLC)

The TX-114 detergent phase sample (6.5 ml) was applied to a Mono Q anion exchange column (Pharmacia LKB Biotechnology Inc., Piscataway, N.J.) at a flow rate of 1.0 ml/min. Unbound proteins were eluted with 18 ml of 50 mM Tris-HCl pH 8.0 containing 0.5% hTX-100 (Buffer A). Proteins which bound the column were eluted with a 30 ml salt gradient from 0 mM to 600 mM NaCl with 50 mM Tris-HCl pH 8.0, 0.5% hTX-100, 1M NaCl (Buffer B) and collected in 0.5 ml volumes with a P-500 Fraction collector (Pharmacia). The chromatogram of the eluted proteins were measured with a UV-1 monitor (Pharmacia) and recorded with a P-500 chart recorder (Pharmacia). The eluted samples were assayed for porin activity with the black lipid bilayer assay and analyzed by SDS-PAGE. Fractions which contained porin activity were pooled, dialyzed against 50 mM Tris-HCl pH 8.0 and reseparated over the Mono Q column with a 40 ml salt gradient from 0–400 mM NaCl.

Black Lipid Bilayer Assays

FPLC eluted fractions were tested with the black lipid bilayer assay as previously described {Skare, J. T., et al., *J. Clin. Invest*., 96:2380–2392 (1995) and Mizabekov, T. A., et al., *J. Membr. Biol*., 133:129–143 (1993)}. The lipid bilayer consisted of diphytanoyl phosphatidylcholine (Avanti Polar Lipids, Alabaster, Ala.) bathed in 1 M KCl, 5 mM Hepes pH 7.4 with an applied voltage of 50mV. The samples were diluted 1:2,000 to 1:30,000 with 1M KCl, 5 mM Hepes pH 7.4 and added to the chamber. Fractions which contained porin activity were then subjected to SDS-PAGE.

SDS-PAGE

Samples were precipitated with 10% trichloracetic acid (TCA), washed with acetone and resuspended in 2× final sample buffer (FSB) containing 4% SDS, 10% β-nercaptoethanol, 20% glycerol, and 0.01% bromphenol blue in 100 mM Tris HCl pH 6.8 and separated over a 11% SDS-polyacrylamide gel as previously described {Laemmli, U. K., *Nature* (London), 277:680–685 (1970)}.

After electrophoresis, protein was transferred to a polyvinylidene difluoride (PVDF; Millipore Corp., Bedford, Mass.) membrane as previously described {Towbin, H., et al., *Proc. Natl. Acad. Sci. USA*, 76:4350–4354 (1979)} and stained with either 1% Amido Black or Auroforte Dye (Amersham Corp., Arlington Heights, Ill.) as described by the manufacturer.

RESULTS

Purification of the 45 kDa Porin Protein from *B. burgdorferi*.

We chose to purify the porin protein from avirulent *B. burgdorferi* based on our preliminary results. The 0.22 nS protein was more abundant in the avirulent strain which also lacks outer surface protein D which co-purified with the porin protein. Treatment of *B. burgdorferi* with 1% Triton X-114 resulted in the solubilization of the outer membrane and the release of several soluble proteins. The phase partitioning characteristics of Triton X-114 allowed for the concentration of hydrophobic proteins in the detergent phase as shown in FIG. 17, lane 2. The major components of this hydrophobic detergent phase were the OspA and OspB lipoproteins (31 and 32 kDa) as previously described. Preliminary screening of the crude detergent preparation with the black lipid bilayer assay resulted in only a few observations of porin activity with single channel conductances of 0.22 nS.

In an attempt to further separate the hydrophobic proteins, we applied the detergent phase over a Mono Q anion exchange FPLC column. This resulted in OspA and OspB appearing in the flowthrough fractions (data not shown), consistent with the predicted PI of these proteins at 8.3 and 8.5 respectively. This allowed for the preliminary removal of the contaminating Osps and the initial separation of the porin proteins from other contaminating proteins. Black lipid membrane analysis of the eluted fractions revealed increased activity of the 0.22 nS porin protein which eluted with 180 mM NaCl. This phenomenon of increasing activity upon further purification has been previously reported with other porin proteins and suggested to be due to contaminating proteins which either inhibit the activity of the porin or compete with porins for binding to the lipid bilayer. SDS-PAGE analysis of the fraction containing porin activity revealed the presence of 5 proteins (data not shown). In an attempt to further purify the porin protein, the active fractions were re-applied over the Mono Q column with a narrower salt gradient/fraction. This resulted in the elution of a 45 kDa protein with 150 mM NaCl. Black lipid bilayer analysis of this purified fraction showed a single channel conductance of 0.22 nS (FIG. 17, lane 3). This unique approach of TX-114 solubilization and separation with the FPLC has allowed for a simple and quick method of purifying hydrophobic proteins from pathogenic spirochetes.

The paucity of Oms45 is supported by several lines of evidence. Oms45 is not visible in the TX-114 detergent phase from $1\times10^8$ organisms and was only visible from the purified fraction containing an equivalent of $7\times10^{10}$ organisms (FIG. 17, lane 3). In addition, the 0.22 nS activity was not detectable in the original detergent solubilization and required further purification in order to be detectable at low levels. Lastly, Oms45 is not visible in 2-D IEF gels from $1\times10^9$ organism equivalence in the outer membrane vesicle preparation {Skare, J., et al., *J. Clin. Investigation*, 96:2380–2392 (1995)}. However, Triton X-114 solubilization of outer membrane vesicles derived from passage 4 *B. burgdorferi* followed by Mono Q FPLC separation resulted in extremely low levels of 0.22 nS activity.

Black Lipid Bilayer Assay

The sensitivity of the perfusion chamber used in our black lipid bilayer analysis has allowed for the detection of relatively rare porin proteins which would normally not be detectable with standard bilayer chambers. This has allowed for the identification of a third porin protein in addition to the 0.6 nS and 10 nS channels previously observed in the outer membrane vesicle preparation. Measurement of 500 insertional events (FIG. 18A) revealed that the average single channel conductance of the Oms45 porin protein was 0.22 nS (220 pS) (FIG. 18B). The demonstration that the purified 45 kDa has porin activity again confirms that it is a transmembrane outer membrane protein of *B. burgdorferi*.

The identification of this outer membrane porin protein further contributes to the characterization of the poorly understood constituent proteins of the outer membrane. We are currently in the process of obtaining amino acid sequences from the purified 45 kDa protein to generate degenerate oligonucleotides in order to clone the gene encoding Oms45.

Example 4

Porin Activity of Oms66 from *Borrelia burgdorferi*

Porin proteins are membrane proteins that, as their name implies, form pores within lipid bilayers. Gram negative bacteria contain two membranes: an inner membrane (IM) and an outer membrane (OM). Since the IM must remain intact in order to support an electrochemical gradient, proteins that form pores, like porins, if integrated in the lipid bilayer, would be lethal due to the depolarization of the cytoplasmic membrane potential. In contrast, the OM in gram negative bacteria is essentially unenergized and must contain pores in order to obtain nutrients via passive diffusion. Therefore, porin proteins are indisputable, functional OM proteins. {Hancock, R. E. W., In Bacterial Outer Membranes As Model Systems, M. Inouye, ed. John Wiley and Sons, New York, N.Y., pp. 187–225 (1986)}. Once nutritional solutes pass through the OM, they may be actively transported across the energized IM.

Until recently no outer membrane-spanning (Oms) proteins had been described for *Borrelia burdorferi*, the etiologic agent of Lyme disease even though Oms proteins had been observed previously by freeze fracture electron microscopy {Walker, E. M., et al., *J. Bacteriol*., 173:5585–5588 (1991)}. In the present invention a methodology was developed that resulted in both the isolation of the OM in the form of OM vesicles (OMV), and the characterization of the protein constituents from the B. burdorferi {Example 1, above, also described in Skare, J. T., et al., J. Clin. Invest., 96:2380–2392 (1995)}. In addition to identifying OM proteins present in the OMV preparations, we also observed two distinct porin activities from the detergent solubilized OMV material with single channel conductances of 0.6 and 12.6 nS.

In this Example we describe the purification of a 66-kDa protein that we have designated Oms66 and demonstrate that this protein functions as porin in an in vitro lipid bilayer with an average single channel conductance of 9.7 nS. The voltage dependence of the previously described 12.6 nS OMV porin and the purified Oms66 reported here were essentially identical, indicating that these two proteins are most likely the same molecule. The amino acid sequence of peptides derived from purified Oms66 was identical to the deduced amino acid sequence of the p66 protein {Bunkitis, J., et al., GenBank accession number X 87725, NCBI gi: 8607874} which has been shown to be surface exposed based on protease digestions of intact B. burgdorferi cells that reduce its apparent molecular mass from 66 kDa to 50 kDa {Probert, W. S., et al., Infect. Immun., 63:1933–1939 (1995)}. These findings indicate that the nucleotide sequence of p66 in the database and its corresponding deduced amino acid sequence encodes the B. burgdorferi Oms66 porin protein.

METHODS

Purification of the Oms66 Porin Protein

Outer membrane vesicles (OMV) derived from $5 \times 10^{10}$ B. burgdorferi strain B31 passage 3 were obtained as previously described {Skare, J. T., et al., J. Clin. Invest., 96:2380–2392 (1995)} and were incubated overnight at 4° C. in a 5 ml volume containing 2% hydrogenated Triton X-100 (hTX-100) buffered in 50 mM Tris HCl pH 8.0. The insoluble material was removed by two successive centrifugations at 13,000 g for 10 minutes at 4° C. The resulting protein within the supernatant was separated with a 1 ml Mono Q column using the Pharmacia fast performance liquid chromatography (FPLC) system (Pharmacia Biotech, Piscataway, N.J.). The column was washed with a 15 ml volume of 0.5% hTX-100 buffered in 50 mM Tris HCl pH 8.0 and thirty separate 0.5 ml flow-through fractions were collected. Proteins bound to the column were eluted off using a 0 to 600 mM linear NaCl gradient containing 0.5% hTX-100 buffered in 50 mM Tris HCl pH 8.0. Sixty consecutive fractions were collected, each representing a successive increase in 10 mM NaCl. The fractions were pooled and tested for porin activity as described previously {Skare, J. T., et al., J. Clin. Invest., 96:2380–2392 (1995)}. Fractions containing peak porin activity were rechromatographed using the Mono Q column as described above.

Planar Lipid Bilayer Assays

Assays to detect porin activity using diphytanoyl phosphatidylcholine as the lipid substrate were conducted essentially as described {Skare, J. T., et al., J. Clin. Invest., 96:2380–2392 (1995)}. Fractions with peak activity were diluted from 1 to 100,000 to as low as 1 to 1,000,000.

SDS-Polyacrylamide Gel Electrophoresis (SDS-PAGE) and Immunoblotting

SDS-PAGE and immunoblotting were conduced essentially as described previously (Skare, J. T., et al., J. Clin. Invest., 96:2380–2392 (1995)}. Briefly, fractions containing peak porin activity were concentrated by precipitation with either a 10-fold excess of ice-cold acetone or 5% trichloroacetic acid (TCA). The precipitated protein was concentrated by centrifugation at 16,000 g for 15 minutes, washed once with ice-cold acetone, and resuspended in Laemmli sample buffer {Laemmli, U. K., Nature (London), 277:680–685 (1970)}. The unboiled samples were resolved by SDS-PAGE, electroblotted to polyvinylidene difluoride (PVDF; Millipore Corp., Bedford, Mass.) and stained with either 1% amido blue or colloidal gold to determine the purity of the given fractions. Immunoblotting was conducted using serum from rabbits immune to challenge {Foley, D. M., J. Clin. Invest., 96:965–975 (1995)}, e.g. immune rabbit serum (IRS), diluted 1 to 1,000. Immobilized immune complexes on the PVDF membrane were detected using a 1 to 2,500 dilution of donkey anti-rabbit immunoglobulin conjugated to horseradish peroxidase (Amersham Corp., Arlington Heights, Ill.). Immunoblots were developed using the enhanced chemiluminescence (ECL) system (Amersham Corp.).

RESULTS

Identification of a 66 kDa Porin Protein from the OM of B. burgdorferi

Detergent solubilization and subsequent FPLC separation indicated that a large channel activity, with an approximate 10 nS conductance, was present in the flow-through fractions adjacent to the start of the NaCl gradient. That is, while the majority of the flow-through proteins were immediately collected early in the 15 ml wash (between 0 to 2 ml), the 10 nS channel washed off late (between 10 to 14 ml with a peak between 11 to 12 ml). These active fractions were reapplied to the Mono Q column and washed off at exactly the same volume range (peak between 11 to 12 ml of the wash). Porin assays of the rechromatographed fractions indicated that these samples had a high specific activity since dilutions out to 1 to 100,000 yielded at least 581 individual step-wise insertional events over a total time period of approximately 15 minutes. The average conductance observed for the 581 individual events was 9.7 nS. In contrast to the 9.7 nS observed here, in Example 1, above, we reported a large channel activity of 12.6 nS {also described in Skare, J. T., et al., J. Clin. Invest., 96:2380–2392 (1995)}. One possible explanation for the differences in the large channel conductance observed in this study could be due to the purification of the porin protein away from other contaminating proteins present in the previous study {Example 1 above; also described in Skare, J. T., et al., J. Clin. Invest., 96:2380–2392 (1995)}. These proteins may have modified the conformation of the large channel thereby yielding an anomalously larger conductance.

SDS-PAGE analysis of these active fractions, and subsequent transfer to PVDF membrane and staining with either colloidal gold or amido black indicated that these samples contained a single 66 kDa protein that we designated Oms66 for outer membrane-spanning 66 kDa protein. Protein assays of active fractions containing Oms66 indicated that between 30 to 50 µg of Oms66 were present in the detergent solubilized OMV supernatant derived from $5 \times 10^{10}$ B. burgdorferi strain B31 passage 3. Further, individual fractions with peak activity contained approximately 14 to 20 µg/ml of Oms66. Therefore, dilutions of 1 to 100,000 yielded active fractions at a final concentration of 140–200 pg/ml of Oms66.

Amino Acid Sequence of Tryptic Fragments Derived from Purified Oms66

Approximately 100 pmoles of purified Oms66 was digested with trypsin, the resulting tryptic peptides purified by reverse-phase high performance liquid chromatography (RP-HPLC), and the peptides sequenced via Edman degradation as previously described {Blanco, D. R., et al., J. Bacteriol., 177:3556–3562 (1995)}. Amino acid sequence of four independently isolated peptides were identical to the deduced amino acid sequence of the p66 protein derived from the nucleotide sequence of the p66 gene {Bunkitis, J., et al., unpublished sequence; GenBank accession number X 87725, NCBI gi: 8607874}. The sequence of the four Oms66 peptides (in order relative to the amino terminus of Oms66/p66) are as follows: (1) LDLTFAIGGTGTGNR (SEQ ID NO:6); (2) YKLGLTK (SEQ ID NO:7); (3) INDKNTYLILQMGTDFGIDPFAS (SEQ ID NO:8); (4) DTGEKESWAIK (SEQ ID NO:9). The second and third peptides listed above are directly adjacent to one another in the deduced amino acid sequence.

Antigenicity of Oms66

We probed purified Oms66 with antiserum from rabbits immune to reinfection with as many as $4 \times 10^7$ *B. burgdorferi* strain B31 passage 4 {Foley, D. M., et al., *J. CLin. Invest.*, 96:965–975 (1995)}. The results indicate that antibody to Oms66 is produced in immune animals; however, since Oms66 is present in both virulent and avirulent isolates of *B. burgdorferi*, Oms66 is not a virulent strain associated, outer membrane-spanning protein or Oms$^{vsa}$ that we described in Example 1, above {Skare, J. T., et al., *J. Clin. Invest.*, 96:2380–2392 (1995)}. Based on the abundance of Oms66 on the surface of *B. burgdorferi* it is tempting to speculate that Oms66 may function as an effective target for borrelicidal antibody binding and, as such, may be an effective vaccine candidate to protect against Lyme borreliosis.

The foregoing is meant to illustrate, but not to limit, the scope of the invention. Indeed, those of ordinary skill in the art can readily envision and produce further embodiments, based on the teachings herein, without undue experimentation.

All publications and patent applications mentioned in this Specification are herein incorporated by reference to the same extent as if each of them had been individually indicated to be incorporated by reference.

We claim:

1. An outer membrane spanning protein isolated from Borrelia outer membrane comprising Oms28.

2. A purified protein consisting essentially of Oms28.

3. An amino acid sequence of Oms28.

4. A pharmaceutical composition comprising an immunogenically effective amount of Oms28.

5. A method of producing antibodies which recognize *Borrelia burgdorferi* comprising administering to a host an immunogenically effective amount of Osm28.

* * * * *